United States Patent [19]

Prendergast

[11] Patent Number: 5,292,725
[45] Date of Patent: Mar. 8, 1994

[54] ADMINISTERING PARTICULAR COMPOUNDS AGAINST VARIOUS PARASITES, MYCOPLASMAS, OTHER INDICATIONS AND OTHER INFECTIONS

[76] Inventor: Patrick T. Prendergast, Baybush, Straffan, County Kildare, Ireland

[21] Appl. No.: 719,017

[22] Filed: Jun. 21, 1991

Related U.S. Application Data

[63] Continuation-in-part of Ser. No. 483,679, Feb. 23, 1990, abandoned, which is a continuation-in-part of Ser. No. 362,820, Jun. 7, 1989, abandoned.

[30] Foreign Application Priority Data

Aug. 25, 1988 [IE] Ireland .................... 2585/88
Jun. 21, 1990 [IE] Ireland .................... 2244/90

[51] Int. Cl.$^5$ ............................ A61K 31/70
[52] U.S. Cl. .................... 514/46; 514/45; 514/895
[58] Field of Search ............ 514/46, 45, 895

[56] References Cited

U.S. PATENT DOCUMENTS

| | | | |
|---|---|---|---|
| 3,666,856 | 5/1972 | Elion et al. | 514/46 |
| 3,758,684 | 9/1973 | Elion et al. | 514/46 |
| 3,851,056 | 11/1974 | Stork et al. | 514/46 |
| 3,966,916 | 6/1976 | Kampe et al. | 514/46 |
| 4,016,262 | 4/1977 | Fauland et al. | 514/46 |
| 4,464,361 | 8/1984 | Ohki et al. | 514/46 |
| 4,657,897 | 4/1987 | Bristol et al. | 514/47 |
| 4,791,103 | 12/1988 | Trivedi et al. | 514/46 |
| 4,843,066 | 6/1989 | Yamada et al. | 514/45 |

*Primary Examiner*—John W. Rollins
*Attorney, Agent, or Firm*—Kevin C. Brown

[57] ABSTRACT

One or more compounds are administered against one or more kinds of parasites and/or one or more diseases caused by such parasites, against one or more kind of Mycoplasma and/or one or more diseases caused by such Mycoplasmas and/or against one or more of the following indications or infections (a) hairy leukoplakia, (b) oral candidosis, (c) mouth ulcerations-aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, and (l) rotaviruses. The present invention furthermore provides specific formulations including such compound(s).

21 Claims, 24 Drawing Sheets

ADMINISTERING PARTICULAR COMPOUNDS AGAINST VARIOUS PARASITES, MYCOPLASMAS, OTHER INDICATIONS AND OTHER INFECTIONS

This is a continuation-in-part of application Ser. No. 07/483,679, filed Feb. 23, 1990, now abandoned, which in turn is a continuation-in-part of application Ser. No. 07/362,820, filed Jun. 7, 1989, now abandoned.

FIELD OF THE INVENTION

This invention relates to administering compounds to beings afflicted with one or more parasites (each believed to be a haemoflagellate parasite of man), and to administering compounds to beings afflicted with disease caused by such parasites. More particularly, but not limited thereto, this aspect of the invention relates to administering compounds to beings afflicted with disease caused by one or more of trypanosomia, leishmania, toxoplasma and/or enterocytozoon bieneusi This invention also relates to specific forms in which said compounds can be provided to facilitate administering them.

This invention further relates to administering compounds to beings infected with Mycoplasma, to administering compounds to beings afflicted with disease caused by Mycoplasma, and to specific forms in which said compounds can be provided to facilitate administering them.

This invention further relates to administering compounds to beings suffering from any one or more of the following indications or infections (a) hairy leukoplakia, (b) oral candidosis, (c) mouth ulcerations aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, and (l) rotaviruses. More particularly, but not limited to, this aspect of the invention relates to administering compounds to HIV infected beings afflicted with oral disease This invention also relates to specific forms in which said compounds can be provided to facilitate administering them.

This invention additionally relates to administering compounds to beings to combat viruses and prions (proteinaceous infectious particles) e.g. CMV, Herpes Simplex, Hepatitis B, Scapie Creutzfeldt-Jakob Disease. Particularly, this aspect of the invention relates to administering compounds to beings suffering from certain retroviral infections, and to beings suffering from infection by retroviruses related to human immuno-deficiency viruses (HIV) and to methods of prophylactic drug treatment of beings who may be suffering from such infections. More particularly, this aspect of the invention relates to administering compounds to beings to reduce levels of HIV virus in blood cells such as the monocyte/macrophage and T lymphocytes of the person being treated. This invention also relates to specific forms in which said compounds can be provided to facilitate administering them.

BACKGROUND OF THE INVENTION

The haemoflagellate parasites of man, despite their close taxonomic relationship within the family Trypanosomatidae, a shared range of morphological types, and common elements of structure and biochemistry, cause a diverse variety of diseases including African and American trypanosomiasis, and leishmaniasis (a person was reportedly exposed to leishmania while in Ireland, an area previously thought to be free of leishmania). This diversity is partially a reflection of the different extracellular and intracellular sites of development adopted by these trypanosomatids. Currently available compounds for use against such parasites suffer from various drawbacks, most notably their unacceptable toxicity.

A considerable effort is currently underway to find more efficacious and less toxic compounds for the clinical treatment of leishmaniasis and trypanosomiasis. A proliferation of studies on the chemotherapy of Leishmania and rational biochemical approaches in studies on Trypanosoma brucei have recently produced promising new leads, but many of the problems associated with the treatment of South American trypanosomiasis (Chagas disease) remain intractable.

Hairy leukoplakia is apparently unique to patients infected with HIV. It consists of white warty like projections occurring particularly on the lateral aspects of the tongue and the cheeks. Its cause is unknown, but electron microscopic studies suggest that a virus (possibly Epstein-Barr or the human papilloma virus) may be implicated. Although it is usually painless, its unsightliness worries many patients.

One of the hardest problems confronting the physician dealing with a patient with HIV antibodies is the difficulty of predicting which patients will progress to AIDS. But there are both clinical features and laboratory markers which may help. Clinical features of a poor prognosis are oral candidosis, herpes, herpes zoster, hairy leukoplakia, and the presence of fever, malaise, diarrhoea, or weight loss.

It is believed that human infection by the family of retroviruses known as HIV is deleterious to the health of infected persons. Examples of viruses which are currently believed to belong to the HIV family are the lymphadenopathy-associated virus (LAV) and the human T-lymphotrophic virus type III (HTLV-III). LAV and HTLV-III, which were discovered independently of each other, are now known to be the same virus and are referred to as HIV-I. Although much is known about modes of transmission of such viruses from person to person, (THE NATURAL HISTORY OF HIV INFECTION IN A COHORT OF HOMOSEXUAL AND BISEXUAL MEN: A DECADE OF FOLLOW UP. Nancy A. Hessol, G. W. Rutherford, A. R. Lifson, P. M. O'Malley, Dept. of Public Health, San Francisco, CA) there is currently controversy regarding particular interactions between the virus and the host cells in which they reside. Generally, a person who is infected by HIV develops antibodies to the virus and at some point, the immune system of the person becomes damaged and becomes ineffective in defending the body from diseases. This condition has come to be known as Acquired Immune Deficiency Syndrome, or AIDS. Eventually, because of the immune deficiency of his or her body, an AIDS patient is overcome by one or more of a group of opportunistic infections, for example, Kaposi's Sarcoma and pneumocystis.

There is evidence that macrophage/monocyte infection is a factor in the progression of HIV infection, in initiating the brain damage that is known to occur in AIDS patients, and in triggering the collapse of the immune system as evidenced by eventual profound depletion of T4 lymphocytes. It has been demonstrated using anti-HIV p24 antibody that monocyte/macrophages can be infected with HIV. Up to 70% of cells from individual donors could be infected (Crowe et al., AIDS Research and Human Retroviruses 3, no. 2, (1987) 135). Nicholson et al. have proposed an HIV-III/LAV-induced effect in monocyte function rather than (or in addition to) an intrinsic defect in surviving T cells to account for observed abnormalities in T cell assays that are monocyte-dependent such as pokeweed mitogen-induced antibody synthesis and proliferative responses to soluble antigens. These T cell assays have previously been reported as abnormal even when assayed as T cell subsets (The Journal of Immunology, 137, No. 1, (1986) 323).

Since it is well established that one of the first events that occurs when a foreign material (for example, a virus) enters the body is its uptake by mononuclear phagocytes, it is conceivable that these cells represent a primary target for HIV. Gartner et al. have shown that virus production by HTLV-III/LAV infected macrophages was high and long-lived, indicating that these cells may play a role in virus dissemination and persistence. They have demonstrated HTLV-III/LAV replication in macrophages was fully productive in the situations they evaluated (Science 233 (1986) 215).

Salahuddin et al. observed that in-vitro pulmonary macrophages can be infected with HTLV-III and appear to be less susceptible to the phytopathic effects of this retrovirus, which suggests that tissue macrophages should be considered as potential reservoirs of HTLV-III in-vitro (Blood 68, No. 1, (1986) 281).

Ho D.D. et al observed normal blood-derived monocytes/macrophages were found to be susceptible to infection in-vitro by HTLV-III. In addition, HTLV-III was recovered from monocytes/macrophages of patients infected with this virus. It was postulated therefore that HTLV-III-infected monocyte/macrophages may serve as a vehicle for the dissemination of virus to target organs and as a reservoir for viral persistence, as has been shown for other lentiviruses, including visna virus and caprine arthritis encephalitis virus (J. Clin Invest. 77, (198) 1712).

Anti-viral agents which inhibit replication of viruses have been known since the mid 1960's. (PROSPECTS FOR THE PREVENTION AND THERAPY OF INFECTIONS WITH THE HUMAN IMMUNODEFICIENCY VIRUS. Markus Vogt, Martin S. Hirsch, Infectious Disease Unit, Massachusetts General Hospital, Harvard Medical School, Boston). Several hundred or more of these agents are now known but azidothymidine (AZT, zidovudine) is the only drug which has received approval from the Federal Drug Administration in the United States for treatment against the virus of people with AIDS. The use of AZT in the treatment of AIDS patients suffers from many deficiencies. AZT is very expensive. Treatment with AZT often causes side effects in persons being treated with it and often the side effects are so severe that treatment with it must be halted altogether. (DEVELOPMENT OF HIV-VARIANTS WITH HIGHER RESISTANCE AGAINST AZT UNDER TREATMENT WITH AZT. F. Zimmermann, L. Biesert, H von Briesen, Klinikum der Universitat, Frankfurt, FRG.) The long term effectiveness of treatment with AZT of AIDS patients is still unknown, although it is believed that AZT treatment will not result in the elimination of the virus from the body of an infected person. There is evidence that AZT-resistant strains of HIV are developing in AIDS patients being treated with AZT (F. Zimmermann and L. Biesert).

As a further background to particular aspects of the present invention, the compound $N^6$- ($\Delta^2$-isopentenyl) adenosine, (IPA), which has formula Ia, illustrated below, has been used previously in clinical trials involving the treatment of cancer. (CYTOKININS AS CHEMOTHERAPEUTIC AGENTS, Annals of the New York Academy of Science, 25, 225–234 Mittleman, Arnold et al. (1975)). IPA is a naturally occurring compound. For example, it has been shown to be an anticodon-adjacent nucleoside in certain t-RNAs ($N^6$- ($\Delta^2$- ISOPENTENYL) ADENOSINE: THE REGULATORY EFFECTS OF A CYTOKININ AND MODIFIED NUCLEOSIDE FROM t-RNA ON HUMAN LYMPHOCYTES. Biochimica et Biophysica Acta, 281:488–500. Gallo, Robert C., et al. (1972)). IPA has been shown to have cytokinin properties, (Mittleman, et al.) to inhibit the growth of human leukemic myeloblasts, to inhibit the growth of cultured lymphocytes stimulated by phytohemagglutinin (PHA) at certain concentrations and to stimulate the growth of cultured lymphocytes stimulated by PHA at lower concentrations (Gallo, et al.). Further, IPA has been used in clinical experiments on humans as a chemotherapeutic agent (Mittleman, et al.).

SUMMARY OF THE INVENTION

According to one aspect of the present invention, one or more compounds according to Formula I (set forth below) is administered to a being (in particular, a human or an animal) afflicted with one or more parasites (e.g., leishmania, trypanosomia, toxoplasma and/or enterocytozoon bieneusi) and/or afflicted with disease caused by such parasites. Such administration of compound(s) is effective against such parasites and diseases, and is of acceptable toxicity.

According to another aspect of the present invention, one or more compounds according to Formula I (set forth below) is administered to a being (in particular, a human or an animal) afflicted with one or more Mycoplasma (in particular, Mycoplasma arthritidis, Mycoplasma fermentans and Mycoplasma incognitus) and/or afflicted with disease caused by such Mycoplasmas.

According to another aspect of the present invention, one or more compound according to Formula I (set forth below) is administered to a being (in particular, a human or an animal) suffering from one or more of the following indications or infections (a) hairy leukoplakia, (b) oral candidosis, (c) mouth ulcerations-aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, and (l) rotaviruses. Such administration of compound(s) is effective against such indications or infections.

According to another aspect of the present invention, one or more compound according to Formula I (set forth below) is administered to a being (in particular, a human or an animal) suffering from viral infection and/or affliction with prions (proteinaceous infectious particles) e.g. CMV, Herpes Simplex, Hepatitis B, Scapie Creutzfeldt-Jakob Disease. Particularly, this aspect of the invention relates to administering compounds to beings suffering from certain retroviral infections, and to beings suffering from infection by retroviruses related to human immuno-deficiency viruses (HIV) and to methods of prophylactic drug treatment of beings who may be suffering from such infection. Such administration of compound(s) is effective against such viral infection and/or prions.

The present invention furthermore provides methods of treatment, therapeutic or prophylactic, against any viral infection and materials which may be used in such methods. Further, the invention provides treatment for an organism infected with (and/or exhibiting abnormal levels of): (a) hairy leukoplakia, (b) oral candidosis, (c) mouth ulcerations-aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, (l) rotaviruses, parasites, diseases caused by such parasites, Mycoplasmas and diseases caused by Mycoplasmas, and HIV. The invention also provideshte pharmaceutical formulations theremselves. Certain embodiments ofhteinventionproide methods of treating blood samples to reduce levels of HIV, parasites, Mycoplasmas or characteristics indicative of (a)–(l) or disease caused by parasites, relative to untreated samples.

Further, the invention provides a process for preventing alteration of morphology or function of a cell latently or actively infected by the HIV virus genome. Such an example would be the ability of IPA to prevent expression of the tat gene product in epidermal Langerhan cells and thus prevent or cause to regress resultant epidermal morphological abnormalities and tumors in patients infected with HIV.

The present invention employs one or more compound according to Formula I:

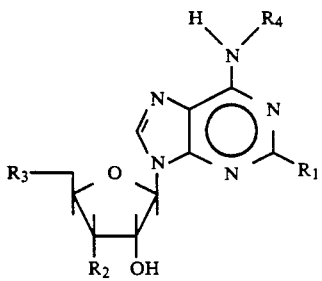

Formula I wherein:
$R_1$=H, $R_2$=CH$_3$, $R_3$=CH$_3$ and $R_4$=H, or
$R_1$=H or CH$_3$S and

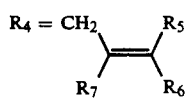

and
$R_5$=CH$_3$, Cl, OH or a monophosphate group
$R_6$=CH$_3$, CH$_2$OH or Cl
$R_7$=H or Br
or $R_1$=H and

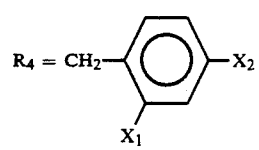

and $X_1$ and $X_2$ are independently selected from H, methyl, ethyl, hydroxyl, the halogens and carboxyl

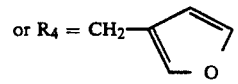

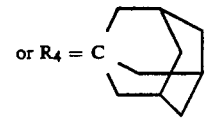

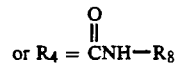

and

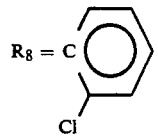

or $R_8$=(CH$_2$)$_7$CH$_3$;
and $R_2$ and $R_3$ are linked to form a 3', 5'-cyclic monophosphate derivative,
or a physiologically acceptable salt of any such compound. "Formula I" is used herein to refer to all of such compounds and salts, as well as (when referring to administration against one or more parasite) polymer of IPA—identified herein as "Poly N6- Isopentenyl Adenosine"—preferably comprising 2-3 monomers.

Listed below are chemical groups $R_1$-$R_4$ for especially preferred compounds Ia–Iu according to this invention.

Ia: $R_1$ = H, $R_2$ = OH, $R_3$ = OH and

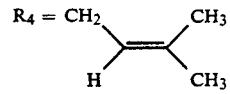

$N^6$—($\Delta^2$-isopentenyl) adenosine

Ib: $R_1$ = H, $R_2$ = OH, $R_3$ = monophosphate, and

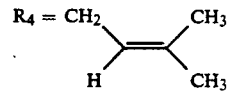

$N^6$—($\Delta^2$-isopentenyl) adenosine-5'-monophosphate

Ic: $R_1$ = H, $R_2$ and $R_3$ are linked to form a 3', 5'-cyclic monophosphate derivative, and

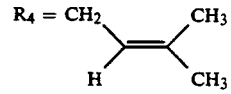

$N^6$-($\Delta^2$-isopentenyl) adenosine-3', 5'cyclic monophosphate

Id: $R_1$ = H, $R_2$ = OH, $R_3$ = OH, and $R_4$ = CH$_2$C$_6$H$_6$ $N^6$-benzyladenosine -continued Ie: $R_1 = H$, $R_2 = OH$ $R_3 = R_3 = $ monophosphate, and $R_4 = CH_2C_6H_6$ $N^6$-benzyladenosine-5'-monophosphate If: $R_1 = H$, $R_2$ and $R_3$ are linked to form a 3', 5'-cyclic monophosphate derivative and $R_4 = CH_2C_6H_6$ $N_6$-benzyladenosine-3', 5'-cyclic monophosphate Ig: $R_1 = H$, $R_2 = OH$, $R_3 = OH$, $R_4 = CH_2$— 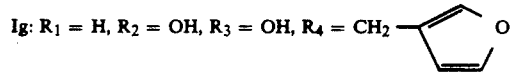

Furfuryladenosine

Ih: $R_1 = H$, $R_2 = OH$, $R_3 = $ monophosphate and $R_4 = CH_2$— 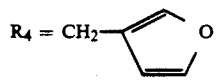

$N^6$-furfuryladenosine-5'-monophosphate

Ii: $R_1 = H$, $R_2$ and $R_3$ are linked to form a

3',5'-cyclic monophosphate derivative, and $R_4 = CH_2$— 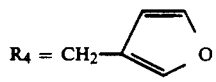

$N^6$-furfuryladenosine-3', 5'-cyclic monophosphate

Ij: $R_1 = H$, $R_2 = OH$, $R_3 = OH$ and

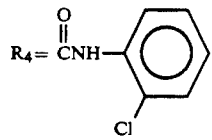

N-(purin-6-ylcarbamoyl)-O-chloroaniline ribonucleoside

Ik: $R_1 = H$, $R_2 = OH$, $R_3 = $ monophosphate and

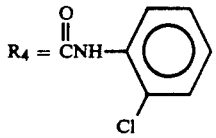

N-(purin-6-ylcarbamoyl)-O-chloroaniline ribonucleoside-5'-monophosphate

Il: $R_1 = H$, $R_2 = OH$, $R_3 = OH$ and

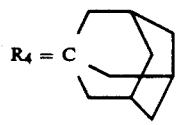

$N^6$-adamantyladenosine

Im: $R_1 = H$, $R_2 = OH$, $R_3 = $ monophosphate and

-continued

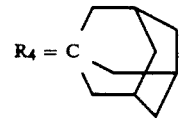

$N^6$-adamantyladenosine-5'-monophosphate

In: $R_1 = H$, $R_2 = OH$, $R_3 = OH$ and

N-(purin-6-ylcarbamoyl)-n-octylamine ribonucleoside

Io: $R_1 = H$, $R_2 = OH$, $R_3 = $ monophosphate and

N-(purin-6-ylcarbamoyl)-n-octylamine ribonucleoside-5'-monophosphate

Ip: $R_1 = H$, $R_2$ and $R_3$ are linked to form a

3'-5'-cyclic monophosphate derivative, and

N-(purin-6-ylcarbamoyl)-n-octylamine ribonucleoside-3', 5'-cyclic monophosphate

Iq: $R_1 = CH_3S$, $R_2 = OH$, $R_3 = OH$ and $R_4 = $ 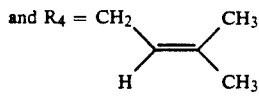

$N^6$-($\Delta^2$-isopentenyl)-2-methylthioadenosine

Ir: $R_1 = H$, $R_2 = OH$, $R_3 = OH$ and $R_4 = $ 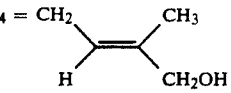

$N^6$-(4-hydroxy-3-methyl-trans-2-butenyl)-adenosine

Is: $R_1 = H$, $R_2 = OH$, $R_3 = OH$, and $R_4 = $ 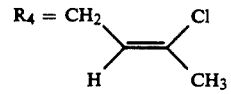

$N^6$-(3-chloro-trans-2-butenyl) adenosine

It: $R_1 = H$, $R_2 = OH$, $R_3 = OH$ and $R_4 = $ 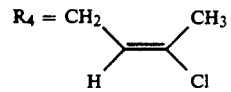

$N^6$-(3-chloro-cis-2-butenyl) adenosine

Iu: $R_1 = H$, $R_2 = CH_3$, $R_3 = CH_3$ and $R_4 = H$

The present invention also employs one or more metabolite of the family of compounds of Formula I. For example, preferred metabolites include:

$N^6$-($\Delta^2$-isopentenyl) adenine;
6-N-(3-methyl-3-hydroxybutylamino) purine;
Adenine;
Hypoxanthine;
Uric Acid; and
Methylated xanthines.

According to another aspect of this invention, there are provided specific forms in which the compounds of Formula I can be administered.

The present invention further provides use of any compound of Formula I in the manufacture or preparation of formulations, and especially pharmaceutical formulations, for use against (a) hairy leukoplakia, (b) oral candidosis, (c) mouth ulcerations-aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, (l) rotaviruses, against parasites and diseases caused by such parasites, against Mycoplasmas and diseases caused by Mycoplasmas, and against HIV. The invention also provides the pharmaceutical formulations themselves.

This invention also relates to establishing improved immuno response in beings in whom immunodeficiency is considered a future risk.

DETAILED DESCRIPTION OF THE INVENTION

Figure 1:
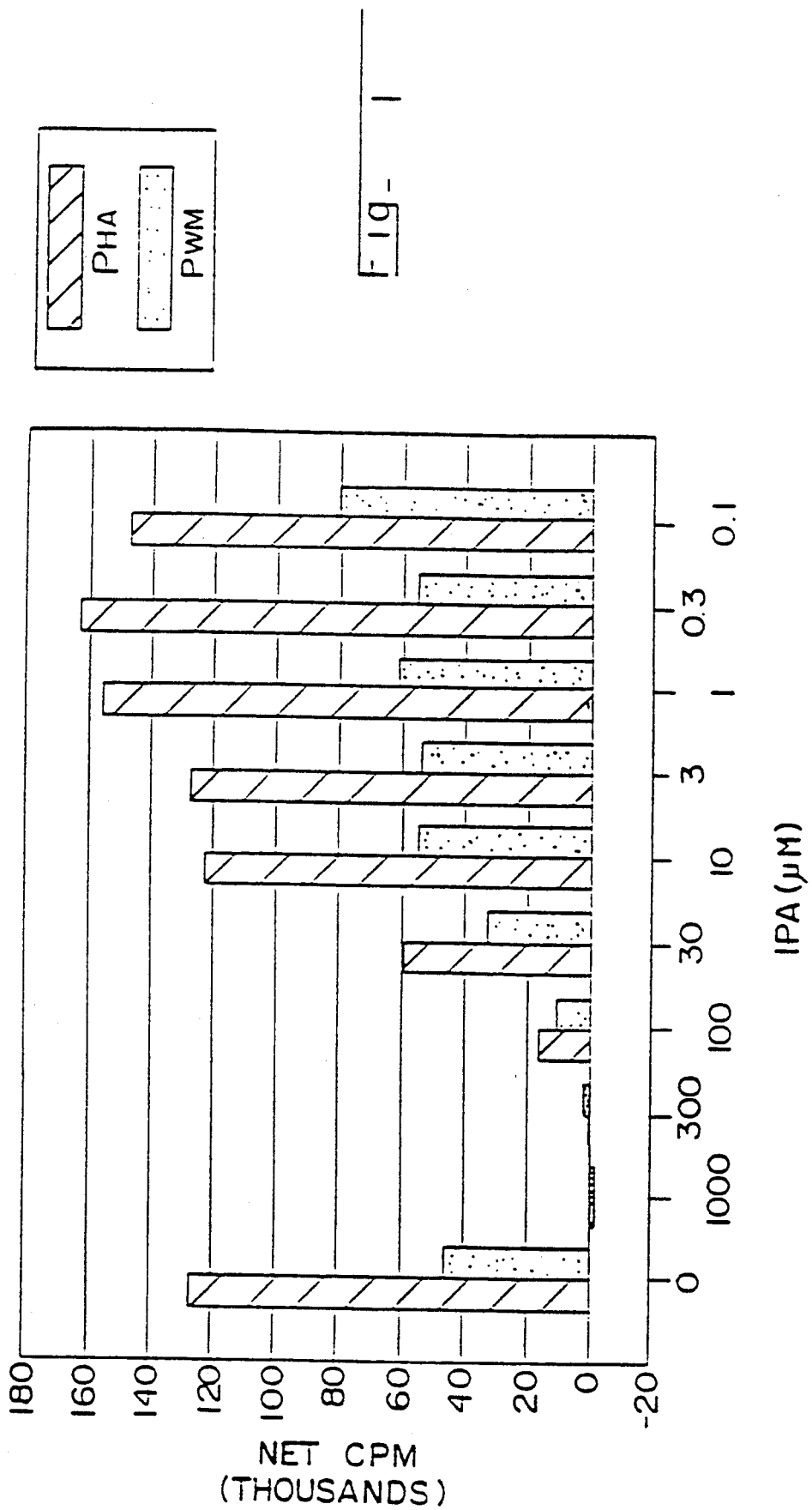
FIG. 1 is a graph of counts per minute versus concentration of IPA in an assay.

Compounds used according to this invention are administered by any suitable route including enteral, parenteral, topical, oral, rectal, nasal or vaginal routes. Parenteral routes include subcutaneous, intramuscular, intravenous and sublingual administration. Topical routes include buccal and sublingual administration.

Pharmaceutical formulations prepared according to the invention include at least one compound of Formula I contained in a macrophage specific liposome micell of suitable size to facilitate phagocytosis, a gelatine capsule, in tablet form, dragee, syrup, suspension, topical cream, suppository, injectable solution (such as a pharmaceutically acceptable solution which may include a carrier), or kits for the preparation of a syrup, suspension, topical cream, suppository or injectable solution just prior to use. Also, compounds of Formula I may be included in a composite which facilitate its slow release into the blood stream, e.g., a silicone disc, polymer beads or a transdermal patch.

Pharmaceutical preparations prepared according to the invention include the employment of compounds of Formula I in admixture with conventional excipients, that is, pharmaceutically acceptable organic or inorganic carrier substances which do not deleteriously react with the compounds. Suitable pharmaceutically acceptable carriers include (but are not limited to) water, salt solutions, alcohols, gum arabic, vegetable oils, gelatine, carbohydrates, magnesium stearate, talc, silicic acid, viscous paraffin, fatty acid mono- and di-glycerides, etc.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

The present invention further provides use of any compound of Formula I combined with an adenosine deaminase inhibitor such as pentostatin to extend the half life of Formula I compounds in the blood stream.

Compounds of Formula Ia (IPA) have especially low toxicity for pediatrics, and acceptable toxicity of adult humans, although it is somewhat higher than for pediatrics. IPA can be stored dry almost indefinitely if protected from light and stored at $-75°$ C. IPA is photosensitive and deteriorates at room temperature, whether in a solid form or in aqueous or ethanolic solutions. It was found in experiments that the breakdown rate of IPA is approximately 3% per month in a dark container at room temperature.

This invention includes the use of physiologically acceptable salts of Formula I, for example, those derived from inorganic acids such as hydrochloric, sulphuric, phosphoric acid, etc., and organic sulphuric acids such as p-toluenesulphonic acid, methanesulphonic acid, etc., and organic carboxylic acids such as acetic, oxalic, succinic, tartaric, citric, malic, maleic acid, etc.

The dosage of any one or more of compounds having Formula I which is effective in treatment against: (a) hairy leukoplakia, (b) oral candidosis, (c) mouth ulcerations-aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, (l) rotaviruses, parasites, diseases caused by such parasites, Mycoplasmas and diseases caused by Mycoplasmas, and HIV will depend on many factors including the specific compound or combination of compounds being utilized, the mode of administration, and the organism being treated. Dosages of a particular compound or combinations of compounds, each belonging to that class defined by Formula I, for a given host can be determined using conventional considerations, for example, by customary comparison of the differential activities of the subject compounds and of a known agent, that is, by means of an appropriate pharmacological protocol.

In one embodiment of the invention, a pharmaceutical formulation comprising a compound having Formula I is administered at the rate of 1 unit dose to 10 unit doses per day, and preferably 1 unit dose to 4 unit doses per day. The doses are given for periods of up to twelve weeks and in certain cases may be given for the life of the patient or, depending on the patient's medical requirements, at less frequent intervals.

In one aspect of the invention, a unit dose comprises 0.01 to 5000 mg of a formulation comprising a compound having Formula I. In one case study, daily dosages in the range of from 250 to 1800 mg of IPA were administered.

In one embodiment of the invention, the pharmaceutical formulation is administered orally in unit doses once per day when the compound is in a slow release form or up to eight unit doses per day when the compound is in its native form. Alternatively or additionally, the pharmaceutical formulation is administered intravenously in unit doses comprising a compound having Formula I in the range of 0.3 mg to 80 mg per Kg of body weight.

In one embodiment of the invention, a pharmaceutical formulation comprising a compound having Formula I is administered by the use of a trans-dermal patch.

In one embodiment of the invention, a pharmaceutical formulation comprising a compound having formula I is administered using an emulsifying or semi-emulsifying formulation to improve absorption from the small intestine. Such an emulsion may be formulated using a derivative of coconut oil, e.g. Miglyol 812.

In accordance with one aspect of this invention, it has been discovered (as confirmed in clinical trials) that formulations comprising one or more compound selected from the group consisting of compounds having Formula I, when administered to beings suffering from one or more of the following indication or infections: (a) hairy leukoplakia, (b) oral candidosis, (c) mouth ulcerations-aphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, (l) rotaviruses, have beneficial effects.

For example, in one particular case study, a patient suffering from AIDS with indications of hairy leukoplakia showed complete relief of hairy leukoplakia upon administration of IPA (compound Ia) administrated in the form of a fluid oral dose or mouth wash with relief of the indication occurring within seven days. When the indication re-appeared, following a period of time (several days), the administration of the compound gave further relief.

In another case study, V.T., a 28 year old homosexual male, was diagnosed HIV positive in June, 1986. V.T. was also diagnosed as having hepatitis at that time. Beginning on May 7, 1990, IPA was administered orally to V.T. On May 7, 1990, V.T. was experiencing (1) weight loss, (2) night sweats, (3) thrush, (4) fungal infections, (5) pneumonia, (6) diarrhea, and (7) hairy leukoplakia.

Prior to treatment with IPA, V.T. had experienced diarrhea and night sweats for the previous six weeks. These symptoms cleared within 48 hours of the beginning of the treatment with IPA. Treatment with IPA resulted in a complete remission of hairy leukoplakia. V.T. experienced a weight gain of about 0.5 lbs per day over the first month of treatment with IPA (on May 7, 1990, V.T. weighed 119 lbs—on Jun. 11, 1990, he weighed 132 lbs). V.T.'s weight stabilized at 133 lbs. V.T.'s energy level and general health greatly improved. V.T.'s T4 count steadily increased creased from 207 (on May 7, 1990) to 330 (on June 21, 1990). V.T.'s helper/suppressor ratio improved from 0.53 (on May 7, 1990) to 0.65 (on Jun. 21, 1990). As of Jul. 26, 1990, V.T.'s helper/suppressor ration was 0.93.

There were observed no permanent toxic side effects from administration of IPA to V.T.

Rotaviruses cause an estimated 140 million cases of gastroenteritis in infants and children and 1 million deaths world-wide each year. They are also the most common cause of hospital-acquired gastroenteritis, infecting 13–27% of children admitted to pediatric hospitals during rotavirus epidemics. Nosocomial rotavirus infections can significantly extend the hospital stay and increase morbidity and financial cost. Rotaviruses belong to the group of virus known as reoviruses, it has no envelope, its shape is icosahedral, its approximate size is 60–80 nm, and it has an RNA nucleic acid structure.

Mycoplasmas are small bacterium-like organisms that normally lead a parasitic existence in close association with animal cells. This invention is directed to administering compound(s) against Mycoplasmas, particularly Mycoplasma Arthritidis, Mycoplasma Fermentans and Mycoplasma incognitus.

In accordance with another aspect of this invention, one or more compound selected from the group of compounds having Formula I is/are administered to a being afflicted with one or more parasites (each believed to be a haemoflagellate parasite of man), e.g., leishmania, trypanosomia, toxoplasma and/or enterocytozoon bieneusi and/or afflicted with disease caused by such parasites.

In accordance with a preferred aspect of this invention, parasites can be targeted by selecting one or more compound(s) which tend to collect in a particular region of the being. For instance, IPA tends to collect in the human liver. This property can be very useful for use against particular parasites which have preferential areas in which to reside. For instance, by using IPA against *T. brucei* (believed to be the cause of sleeping sickness), which preferentially resides in the liver and spleen of a human, lower dosages can be used against the T brucei in the liver.

It is believed that the present invention kills and/or prevents replication and/or causes intracellular digestion of parasites in macrophages. This is especially believed to be true in the case of toxoplasmosis, whose mode of survival is believed to be through macrophages. Thus, this invention further relates to administration to beings afflicted with any parasite whose mode of survival is similar to that of toxoplasmosis.

In-vitro screens in the experimental chemotherapy of leishmaniasis and trypanosomiasis must provide active or dividing populations of the mammalian stages of the parasite. They must provide a measure of drug activity that is readily quantified, and accurately show the activity of standard drugs at concentrations close to those achievable in serum or tissues (over a long time-course if necessary). Inevitably, however, in-vitro screens ignore important host factors involved in absorption, metabolism and pharmacokinetics of drugs, so in assessing different screens one must also bear in mind their accuracy in predicting in-vitro activity of new compounds, and whether or not the system has the facility to examine additional features of interest, such as variation in drug susceptibility between strains and subspecies, drug resistance, and effects of immune or metabolic components.

Leishmaniasis

Following initial infection, the amastigote is the only form present in the mammalian host, surviving and dividing in various macrophage populations. Differences between the promastigote and amastigote in form and habitat are not matched by known biochemical dissimilarities. However, the drug susceptibility of the cultured promastigote, used in many early chemotherapy screens, contrasts markedly with that of the amastigote (see Table 1, below), most importantly to the clinically used pentavalent antimonials—sodium stibogluconate (Pentostam) and meglumine antimoniate (Glucantime).

Amastigotes of Leishmania can be cultivated in a wide range of mammalian cells, some of which may be used in in-vitro screens. These include (1) a Sticker dog sarcoma (fibroblast) cell line, (2) transformed rodent macrophage cell lines, (3) primary isolated mouse peritoneal macrophages (MP mo), and (4) human monocyte-derived macrophages gote or promastigote infected cells are maintained in a medium containing the drug for 4–7 days, at 37° C. for L. donovani and 33–35° C. for L. major and L. mexicana. Drug activity is then assessed by counting (I) the number of infected host cells and/or (II) the number of amastigotes/100 host cells. For some compounds, the method of counting can influence the measure of activity; for example, pentamidine was found to be inactive against *L. donovani* in MP mos by method (I) but active by method (II).

South American Trypanosomiasis

The chemotherapeutic targets in Chagas disease are the non-dividing, tissue invading, bloodstream trypomastigotes, and the dividing intracellular amastigotes, often sequestered within the muscle and difficult to eliminate. In Table 2 (below), the activities of selected drugs, including clinically used compounds nifurtimox (Lampit) and benznidazole (Rochagan), are shown to indicate differences observed between in-vitro systems and between strains of *T. cruzi*. In-vitro chemotherapy screens have for many years used models involving three stages of the *T. cruzi* life cycle:

(1) Epimastigote. Dividing populations are easily cultivated in a range of defined and semi-defined media, but are equivalent to a vector stage of the life cycle.

(2) Trypomastigote. These are isolated from a rodent host and can be maintained as a non-dividing population for 24–48 h in media.

(3) Amastigote. Dividing populations can be cultivated in muscle cells, fibroblasts and macrophages, following infection with trypomastigotes. After the initial infection, there is normally a period of 4–5 days during which the amastigotes divide before transforming, via the epimastigote stage, back to trypomastigotes which escape from the cell. Drug activity is measured during this 4–5 day period. A dividing host cell population, low infection rate, and the presence of trypomastigotes in the overlay can complicate the interpretation of results.

Intracellular amastigote models can use a range of muscle (skeletal and cardiac) and fibroblast (e.g. HeLa, HePa) cell lines, macrophages, and chick embryo cells. The choice of host cell may be relevant to the assessment of drug activity; some drugs, such as puromycin amino-nucleoside and ketoconazole may be metabolized prior to fixation by the amastigote. Compounds that act on *T. bruzi* through the generation of free radical metabolites also interact with host cells, particularly macrophages. To overcome the problems of overgrowth of the monolayer and a low percentage of infected cells, often associated with the use of cell lines, irradiated rat L6 myoblasts are used.

African Trypanosomiasis

A compound for treating African trypanosomiasis must be active against the trypomastigotes of T. brucei gambiense and *T. brucei* rhodesiense in the blood and cerebro-spinal fluid (CSF), and against extravascular forms present in the brain, particularly the choroid plexus region. Although considerable progress has been made with the in-vitro cultivation of blood stream trypomastigotes for use in drug screens, the ability of compounds to pass through the blood-CSF barriers, as already demonstrated for IPA, and their activity against extravascular brain forms continue to be examined in rodents and primates.

Primary screening for new trypanocides has made extensive use of rodent systems, in which host survival time is a simple indicator of drug activity. In-vitro screens have used a variety of trypomastigote types (see Table 3, below). The procyclic trypomastigote of *T. brucei*, a form equivalent to that found in the tsetse midgut, is easy to culture but possesses many different biochemical and structural characteristics to the bloodstream trypomastigote and is therefore of limited use. Most early in-vitro screens employed a short test in which bloodstream trypomastigotes were isolated from an infected rodent and maintained for up to 24 h in a simple drug-containing media. Two significant modifications of this technique include maintaining isolated bloodstream trypomastigotes in drug-containing media for 3–4 hours at 37° C. in micro-titer plates and their subsequent viability assessed by the uptake of radiolabelled precursors or motility and infectivity to mice.

Culture systems developed in the last decade have used mammalian cell feeder layers to support the growth of dividing populations of bloodstream trypomastigotes of T. brucei spp. Some of these systems have been used in chemotherapy studies, including; (1) bovine fibroblast culture—T. brucei models to test some standard and experimental compounds, (2) murine bone marrow culture T.b. gambiense model to screen inosine analogues and platinum and hypolipidemic compounds, and (3) Microtus embryonic fibroblast culture (MEF-)—T.b. rhodesiense model to test standard and experimental drugs. These systems give a good indication of in-vivo activity (see Table 3). They measure activity against dividing cells rather than specific macromolecular synthesis pathways and can be readily established in micro-titer plates. The MEF and bone marrow cell feeder layers can be used to grow a range of strains of T. brucei spp., offering the possibility of examining variations in drug susceptibility and resistance between strains. The presence of a feeder layer, however, limits the opportunities for the automation of these systems.

In-vitro studies on isolated bloodstream trypomastigotes were also used in the rational biochemical approaches towards the chemotherapy of T. brucei infections involving inhibitors of carbohydrate catabolism salicyl hydroxamic acid plus glycerol), of polyamine synthesis (methylgyoxal bis-guanylhydrazone and -DFMO), and of surface coat glycoprotein synthesis (Tunicamycin). In these studies, activity of the compounds are shown in-vitro and in-vivo, whereas the sensitivity of isolated bloodstream trypomastigotes to toxic oxygen radicals generated by naphthoquinones was not shown by the parasites in mice. The activity of the standard anti-trypanosomals melarsoprol, pentamidine and suramin and tested compounds according to the present invention in in-vitro systems is shown in Table 3.

Toxoplasmosis

Toxoplasma gondii:-protozoon is the etiologic agent of toxoplasmosis. This sporozoa is an intracellular parasite Toxoplasma gondii that lives inside macrophages and has evolved a mechanism to avoid being killed by intracellular oxygen, metabolites and lysosomal enzymes.

The live parasite Toxoplasma gondii when ingested by the macrophage forms a membrane bound vesicle called a phagosome. This phagosome containing Toxoplasma parasite can inhibit the fusion to the phagosome of lysosomes which would cause its digestion and elimination. However, if dead Toxoplasma parasites are ingested by macrophages, the phagosome thus resulting cannot prevent lysosome fusion, and parasite digestion. If the macrophage is treated with IPA, it reduces RNA and protein synthesis both in the macrophage and in the parasite, but this imbalance in biosynthetic ability favours the macrophage as opposed to the Toxoplasma parasite since the intracellular macrophage lysosomes are already in position with specific receptors for their attachment to certain markers on the phagosome containing the Toxoplasma parasite. It is the function of the biosynthetic machinery of the parasite to synthesize molecules which block the ability of the lysosome to fuse with the Toxoplasma phagosome, thus IPA's ability to reduce RNA and de novo protein synthesis alters this dynamic synthetic balance and allows lysosomal fusion and digestion of the Toxoplasma Phagosome.

Figure 24:
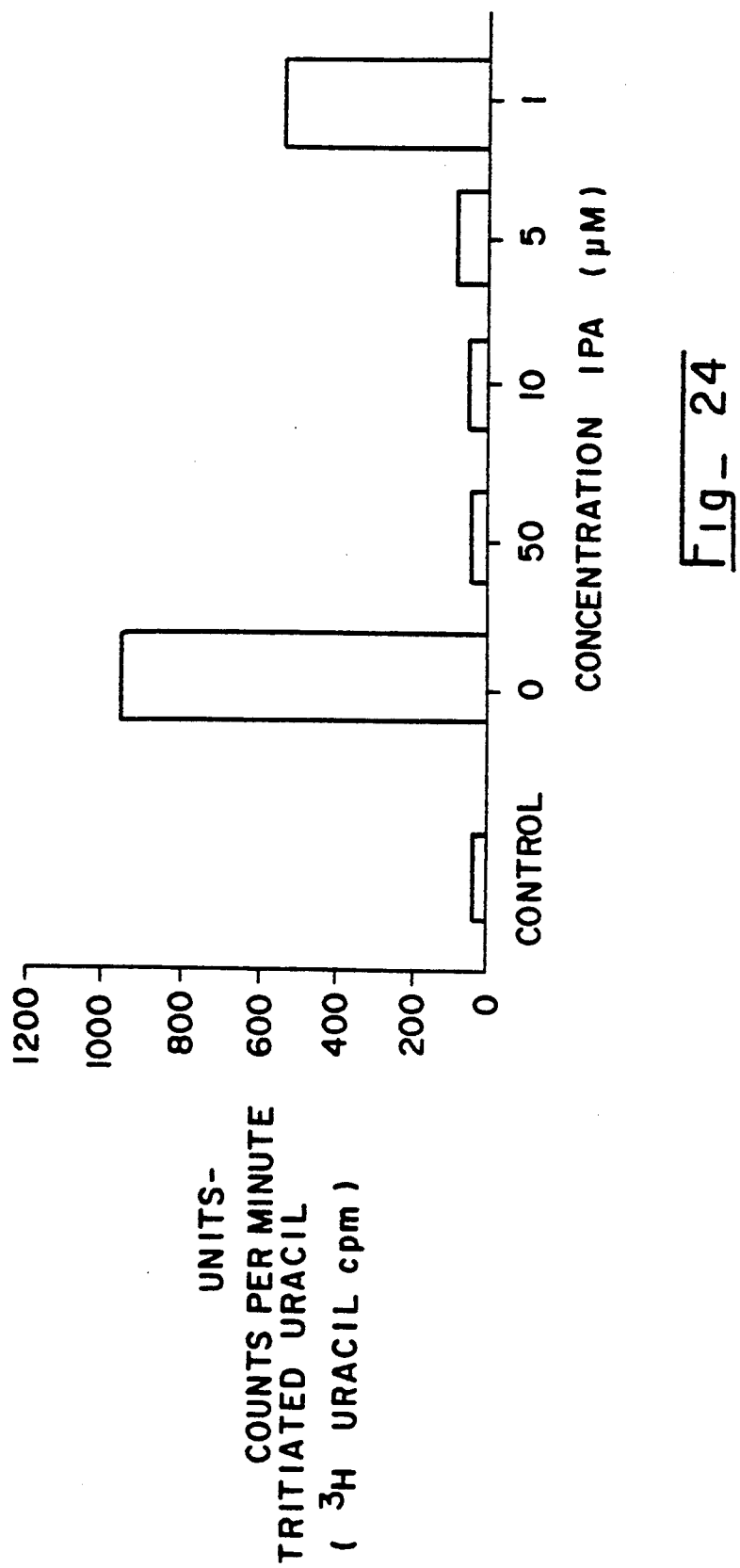
FIG. 24 is a graph of the effect of various concentrations of IPA on the growth of Toxoplasma gondii in human fibroblasts.

An experiment was conducted to evaluate the invitro effects of IPA on Toxoplasma gondii by infecting human foreskin fibroblast monolayers (four replicates per condition) with RH strain T. gondii in the presence of various concentrations of IPA dissolved in Eagle's minimum essential medium without fetal bovine serum. After an initial four hour period of infection, the media and any T. gondii which had not entered the host cells were removed and replaced by media containing 1 μM tritiated uracil per milliter, and incubated overnight. The monolayers were lysed, nucleic acids precipitated by trichloroacetic acid, and the precipitates recovered on glass fiber filters. Radioactivity on the filters was measured in a Beckman scintillation spectrometer. Controls included fibroblast monolayers without T. gondii (cell control) and fibroblast monolayers infected by the same inoculum of T. gondii as the IPA treated monolayers (Tg control). The results of our experiment are shown in FIG. 24. The units of uracil incorporation are somewhat lower here because of the lower inoculum of T. gondii. Host cells have been tested and were free of mycoplasma—these experiments provide strong evidence of an inhibitory effect of IPA on the growth of T. gondii.

Enterocytozoon Bieneusi Microsporidiosis

Chronic diarrhoea accompanied by wasting is one of the most frequent problems associated with HIV infection. Clinical evaluation of patients, treated with IPA including stool examinations and endoscopic biopsies, fails to identify any pathogen. A new genera and species of microspora, Enterocytozoon bieneusi, was identified in ultrastructural studies of intestinal biopsies from AIDS patients with unexplained chronic diarrhoea prior to treatment with IPA.

E. bieneusi microsporidiosis (intestinal microsporidiosis) is diagnosed with increasing frequency in AIDS patients with chronic diarrhoea of unknown origin. Forty-seven cases have been reported in the United States, Africa and Europe. Reporting an incidence of 30% in a homosexual group, these findings suggested that E. bieneusi is an important cause of diarrhoea in AIDS patients. Until now, diagnosis depended upon light and electron microscopy studies of small bowel biopsies, particularly of the doudenum. Diagnosis is suspected on histological findings either on Giemsa-stained smears and/or hematoxylin-eosin or Giemsa-stained paraffin sections: identification of oval parasites measuring 2–9 μm and clusters of refractile spores (1–1.5 μm) in villous enterocytes from just above the mouth of the crypts to the tips of the villi. These organisms are located in the supranuclear position of the cytoplasm. Identification of E. bieneusi is confirmed by electron microscopy which reveals the following characteristic features: multinucleated proliferative and sporogonial plasmodia, measuring 4–6 μm without parasitophorus vacuole and mitochondria; presence of numerous electron-dense precursors spores measuring 1.5×0.5 μm with a poorly differentiated endospore, coiled polar filament (5–7 coils) and electron lucent vacuole. Recently reported recovery of spores from faeces, would simplify diagnosis. Unlike other species of microspora, *E. bieneusi* has not been identified from different organs such as brain and kidney. A proportion of transient diarrhoeas of unknown etiology in AIDS patients may be related to *E. bieneusi*. Contamination of water with faeces and/or close human contact are involved in transmission. No treatment was known to be efficacious prior to this study using Isopentenyl Adenosine.

Compounds Ia and Ib are particularly preferred for use against *Enterocytozoon bieneusi*.

In-vitro and in-vivo models were used to test activities of a selection of many compounds. Those activities are summarized in Tables 1-3, showing variation between systems and species. Activities measured in the MP mo and HM mo models have shown the best correlation with results obtained in hamster and mouse models.

| | in-vitro | | | in-vivo |
|---|---|---|---|---|
| Compounds and Leishmania spp. | PRO | AM-PRO transform- ation | AM in cell lines | AM in mouse or human mos | mouse/ hamster models |
| Sodium stibogluconate | | | | | |
| Ld. | − | − | − | ++ | ++ |
| Lm. | − | ++ | − | ++ | + |
| Pentamidine | | | | | |
| Ld. | ++ | ++ | − | + | + |
| Lm. | ++ | ++ | + | ++ | − |
| N6-Isopentenyl Adenosine | | | | | |
| Ld. | ++ | ++ | − | ++ | + |
| Lm. | + | ++ | + | ++ | − |
| Furfuryladenosine | | | | | |
| Ld. | ++ | ++ | − | + | + |
| Lm. | ++ | ++ | + | ++ | + |
| N6-Benzyladenosine | | | | | |
| Ld. | ++ | ++ | − | + | − |
| Lm. | ++ | ++ | + | + | − |
| N6-Isopentenyl Adenosine-5'monophosphate | | | | | |
| Ld. | ++ | + | − | + | + |
| Lm. | − | ++ | + | ++ | − |
| Poly N6-Isopentenyl Adenosine | | | | | |
| Ld. | ++ | ++ | − | ++ | + |
| Lm. | ++ | − | − | ++ | + |

Activity
− no/poor activity,
+ fair/moderate activity,
++ good/excellent activity
Ld. — L donovani.
Lm. — L major/L mexicana
PRO — Promastigote
AM — Amastigote

TABLE 2

Activity of compounds against *T. cruzi* strains in in-vitro and in-vivo systems

| | in-vitro | | | in-vivo |
|---|---|---|---|---|
| Compound | EPI | TRY | intracellular AM | mouse model |
| Nifurtimox | ++(Y,WBH, Sonyla)+(MR) | ++(WBH,Sonya) +(Tu) | ++(Y,WBH Sonya) | ++(Y,WBH,CL) +(Y,CL,Tu Sonya) |
| Benznidazole | ++(Y,MR, Sonya) | ++(Y,Sonya) | ++(Y,Sonya) | ++(Y)+(Sonya) Sonya) |
| N6-Isopentenyl Adenosine | ++(Y,MR, Sonya) | +(Y,Sonya) | ++(Y,Sonya) | ++(Y)+(Sonya) |
| Furfuryladenosine | ++(Y,MR, Sonya) | +(Y,Sonya) | +(Y,Sonya) | Sonya) ++(Y)+(Sonya) |
| N6-Benzyladenosine | +(Y,MR, Sonya) | +(Y,Sonya) | +(Y,Sonya) | +(Y)+(Sonya) |
| N6-Isopentenyl Adenosine-5'-Monophosphate | +(Y,MR, Sonya) | ++(Y,Sonya) | ++(Y,Sonya) | ++(Y)+(Sonya) |
| Poly N6-Isopentenyl Adenosine | ++(Y,MR, Sonya) | +(Y,Sonya) | ++(Y,Sonya) | +(Y)+(Sonya) | activity:
− no/poor activity,
+ fair/moderate activity,
++ good/excellent activity
*T. cruzi* strains in parenthesis
EPI — Epimastigote
TRY — Trypomastigote
AM — Amastigote

TABLE 3

Activity of compounds against T.b. brucei, T.b. gambiense and T.b. rhodesiense in in-vitro and in-vivo systems

| Compound | in-vitro | | | in-vivo mouse model |
|---|---|---|---|---|
| | procyclic TRY | isolated bloodstream TRY | cultivated bloodstream TRY | |
| Melarsoprol | | ++ | ++ | ++ |
| Pentamidine | | ++ | ++ | ++ |
| Suramin | − | −,+ | + | ++ |
| N6-Isopentenyl Adenosine | + | + | ++ | ++ |
| Furfuryladenosine | + | ++ | + | + |
| N6-Benzyladenosine | ++ | | ++ | ++ |
| N6-Isopentenyl Adenosine-5′-Monophosphate | ++ | + | + | + |
| Poly N6-Isopentenyl Adenosine | + | + | ++ | ++ | activity:
− no/poor activity,
+ fair/moderate activity,
++ good/excellent activity Compounds of Formula I have been found to have valuable pharmaceutical properties as anti-viral agents.

A case study of an AIDS patient, T. W., was conducted. Patient T.W. began treatment with IPA in February 1989, while in a nearly moribund condition, suffering from depression, exhaustion, bronchial infection, severe diarrhoea, severe weight loss (weight in February was 98 lbs.), complete loss of appetite and spiked fever. The case study reveals a major rapid recovery of T and B lymphocyte competence. By Mar. 21, 1989, patient T.W. stated that he felt cured and abruptly (unilaterally) stopped taking IPA, resulting in dramatic deterioration of his condition. In May, 1989, patient T.W. resumed IPA therapy, and experienced dramatic recovery. At the end of May, 1989, patient T.W. again stopped taking IPA, and his condition again deteriorated. Again IPA treatment was re-started, and patient T.W.'s condition improved. In early June, 1989, patient T.W. again stopped IPA therapy and died several weeks later.

The study concluded that patient T.W. would have apparently enjoyed appreciable therapeutic benefits from IPA if he had conscientiously and continuously received IPA medication.

Also, compound Ia, IPA, has been found through in-vitro experiments to inhibit the replication of HIV-1 in monocyte/macrophage cells and in T4 lymphocytes as well as Langerhan cells at levels which are non-toxic to the cells themselves.

Studies have been carried out which show that IPA reduces levels of HIV in HIV-infected macrophage cells treated with IPA relative to infected macrophage cells not treated with IPA. Toxicological studies have been carried out using uninfected cells (T and B lymphocytes and monocytes) which show that such cells can tolerate exposure in-vitro to IPA at levels which reduce levels of HIV in HIV-infected macrophage cells.

Studies have been carried out which indicate that IPA reduces in-vitro levels of HIV in HIV-infected H9, 81-66-45, and monocyte/macrophage cells relative to similar cells HIV-infected not treated with IPA.

Experiments to show the in-vitro effect of IPA on human leukocyte viability have been carried out.

Studies have been carried out that indicate that IPA, in in-vitro experiments, reduces levels of caprine arthritis encephalitis virus (CAEV) in Himalayan Tahr ovary cells.

Studies have been carried out which show that IPA reduces in-vitro levels of herpes simplex type 1 (HSV 1) in an M413 cell line of human fibroblasts.

Studies have been carried out which show that IPA reduces levels of cytomegilovirus in cells in-vitro.

Studies have been carried out which show that IPA reduces levels of Epstern-Barr Virus (EBV) in P₃HR1 cells in-vitro.

The effectiveness of a particular regimen (of administration of a compound of Formula I) can be monitored by following over time the presences of parasites, Mycoplasma, HIV or characteristics indicative of: (a) hairy leukoplakia, (b) oral candidosis, (c) mouth ulceration-saphthous/herpetic/bacterial, (d) fungal candida, (e) human papilloma virus, (f) molluscum contagiosum, (g) squamous oral carcinoma, (h) Kaposi's sarcoma oral lesions, (i) periodontitis, (j) necrotizing gingivitis, (k) orofacial herpes zoster, (l) rotaviruses, or diseases caused by parasites or Mycoplasma in blood samples of an organism being treated. There are available commercially kits for the detection of HIV antigens. The use of one such kit for detecting the antigen of HIV-1 was used as described in Example Ia of this invention. It will be possible to cause a reduction, over a period of about two months, in the level of detectable antigen in the blood serum of a patient by means of administration of compounds of Formula I. A better measure of the progression of the level of infection would be the percentage infected macrophage population. Monocytes/macrophage cells obtained from either the blood or the lung during a course of treatment with compounds of Formula I will show a reduction in recoverable HIV antigen as the therapy progresses.

In another embodiment of the invention, the method of the invention comprises the step of treating a patient with known immune system booster or immune system modulator to enhance the production of T-cells by the bone marrow. The patient is treated with the immune system booster prior to administration of a pharmaceutical formulation comprising a compound having Formula I. In another case, the patient is treated with the immune system booster until the level of production of T-cells by the bone marrow (having been reduced by the infection) is stabilized or begins to increase. In particular, the immune system booster is administered until the level of T-4 cells is stabilized or begins to increase.

In another embodiment of the invention, the method includes the step of treating a patient with an immune system booster both prior to and simultaneously while a pharmaceutical formulation comprising a compound having Formula I is being administered.

Tests were carried out to determine the effectiveness of IPA at reducing the levels of HIV-I in infected macrophages. Tests were also carried out to determine the toxicological effect of IPA on uninfected T lymphocytes, B lymphocytes and monocytes.

Experiments, described in the examples below, were carried out which show the effectiveness of IPA at reducing the levels of HIV-I in HIV-I-infected macrophage cells in-vitro. Experiments performed also show the relative effectiveness of AZT and dideoxycytidine (ddC) at reducing the levels of HIV-I in infected macrophage cells. Further experiments were carried out which show that human T and B lymphocytes and monocytes have a high tolerance for IPA in-vitro.

Generally, in experiments to test the ability of IPA to reduce the concentration of viral antigen, IPA was initially made into a 10 millimolar (mM) stock solution in sterile saline. This was used to produce final concentrations from 1 mM to 1 μM. Because IPA does not readily dissolve in water and is photosensitive, it was, in some case, dissolved at 2 mM directly into the growth medium, and this was used to make solutions of the desired concentrations

EXPERIMENT Ia(a)

Macrophage Cells, HIV-I, Antibody Assay

Fresh macrophage cultures were obtained by incubation of mononuclear cells obtained from a leukopak directly in the wells of a microtiter plate having 6 wells per row. After removal of non-adherent cells, each row of the adherent macrophages was infected with 10-fold serial dilutions of HIV-I, with the use of polybrene to enhance uptake of the virus. After one to two hours, the virus inoculum was removed and replaced with fresh normal growth medium. The fresh medium for each row contained a particular concentration of AZT, dideoxy cytidine (ddC), or compound Ia, as indicated by the left-hand column of Table Ia(a). The first row of wells acted as a control, and to it was added fresh medium containing none of the three drugs. Medium levels were maintained for two to four weeks to allow replication of the virus to take place, with at least one complete fluid change to remove residual virus inoculum. The contents of each well were then tested for the level of HIV p24 antigen present using a commercially available antigen capture kit employing a radio-immunoassay which can detect as little as $10^{-9}$ gm of p24 present in a sample. The above procedure was done in duplicate runs.

The results were interpreted as follows: 2/2, for example, means that both the corresponding wells of both runs were positive for HIV-I p24, while 0/2 means that neither well was positive. The titers are given in the next to last column; where 1/2 wells was positive, an intermediate value was given to the titer that is half way between the two dilutions when calculated on a logarithmic scale. 3 μM IPA was positive in both wells at a dilution of 1/10,000 and in neither well at 1/100,000. Thus, one half log interval between $10^4$ and $10^5$ is $10^{4.5}$, or 30,000.

TABLE Ia(a)

| DRUG | | LOG VIRUS DILUTION | | | | | | TITER | PERCENT OF CONTROL |
|---|---|---|---|---|---|---|---|---|---|
| | | −1 | −2 | −3 | −4 | −5 | −6 | | |
| None | (control) | 2/2 | 2/2 | 2/2 | 2/2 | 1/2 | 0/2 | 100000 | 100 |
| ddC | 100 μM | 2/2 | 2/2 | 2/2 | 0/2 | 0/2 | 0/2 | 3000 | 3 |
| ddC | 10 μM | 2/2 | 2/2 | 2/2 | 1/2 | 0/2 | 0/2 | 10000 | 10 |
| IPA | 1000 μM | 0/2 | 0/2 | 0/2 | 0/2 | 0/2 | 0/2 | 10 | 0 |
| IPA | 300 μM | 0/2 | 0/2 | 0/2 | 0/2 | 0/2 | 0/2 | 10 | 0 |
| IPA | 100 μM | 2/2 | 2/2 | 0/2 | 0/2 | 0/2 | 0/2 | 300 | 0.3 |
| IPA | 30 μM | 2/2 | 2/2 | 1/2 | 0/2 | 0/2 | 0/2 | 1000 | 1 |
| IPA | 10 μM | 2/2 | 2/2 | 2/2 | 1/2 | 0/2 | 0/2 | 10000 | 10 |
| IPA | 3 μM | 2/2 | 2/2 | 2/2 | 2/2 | 0/2 | 0/2 | 30000 | 30 |

It was observed during these experiments that, although the monocyte-macrophage cultures appeared to be healthy at all concentrations of IPA used, the differentiation of small immature monocytes into large adherent macrophage cells did not take place in the presence of IPA.

EXPERIMENT Ia(b)

H9 Cells, HIV-1, Antibody Assay

A procedure similar to that followed in Experiment Ia(a) was followed using infected H9 cells, H9 cells being a permanent human T-cell line. The results are listed in Table Ia(b).

TABLE Ia(b)

| DRUG | CONCENTRATION | TITER | PERCENT INHIBITION |
|---|---|---|---|
| None | — | $1 \times 10^4$ | — |
| IPA | 1000 μM | <10 | >99.9 |
| IPA | 300 μM | <10 | >99.9 |
| IPA | 100 μM | 10 | 99.9 |
| IPA | 30 μM | $1 \times 10^2$ | 99 |
| IPA | 10 μM | $1 \times 10^3$ | 90 |
| IPA | 3 μM | $1 \times 10^3$ | 90 |
| IPA | 1 μM | $1 \times 10^4$ | 0 |
| ddC | 100 μM | 10 | 99.9 |
| ddC | 10 μM | $1 \times 10$ | 99 |

EXPERIMENT 1a(b)

H9 cells, HIV-I, Antibody Assay

A procedure similar to that followed in Experiment Ia(a) was followed using infected H9 cells, being a permanent human T-cell line. The results are listed in Table 1a(b) (i).

TABLE Ia(b) (i)

| DRUG | CONCENTRATION | TITER | PERCENT INHIBITION |
|---|---|---|---|
| None | — | $1 \times 10^4$ | — |
| IPA | 1000 μM | <10 | >99.9 |
| IPA | 300 μM | <10 | >99.9 |
| IPA | 100 μM | 10 | 99.9 |
| IPA | 30 μM | $1 \times 10^2$ | 99 |
| IPA | 10 μM | $3 \times 10^3$ | 90 |
| IPA | 3 μM | $1 \times 10^3$ | 90 |
| IPA | 1 μM | $1 \times 10^4$ | 0 |
| ddC | 100 μM | 10 | 99.9 |

TABLE Ia(b) (i)-continued

| DRUG | CONCENTRATION | TITER | PERCENT INHIBITION |
|------|---------------|-------|--------------------|
| ddC | 10 μM | 1 × 10^11 | 99 |

These experiments were repeated and the results are listed in Table Ia(b) (ii).

TABLE Ia(b) (ii)

| DRUG | CONCENTRATION | TITER | PERCENT INHIBITION |
|------|---------------|-------|--------------------|
| None | — | 1 × 10$^4$ | — |
| IPA | 1000 μM | <10 | >99.9 |
| IPA | 300 μM | <10 | >99.9 |
| IPA | 100 μM | <10 | >99.9 |
| IPA | 30 μM | <10 | >99.9 |
| IPA | 10 μM | 3 × 10$^2$ | 97 |
| IPA | 3 μM | 1 × 10$^4$ | 0 |
| IPA | 1 μM | 1 × 10$^4$ | 0 |
| AZT | 100 μM | <10 | >99.9 |
| AZT | 10 μM | <10 | >99.9 |
| ddC | 100 μM | <10 | >99.9 |
| ddC | 10 μM | <10 | >99.9 |

EXPERIMENT Ia(c)

Himalayan Tahr Ovary Cells, CAEV, Antibody Assay

A procedure similar to that followed in Experiment Ia (a) was followed using Himalayan Tahr ovary cells exposed to caprine arthritis encephalitis virus (CAEV), a lentivirus related to HIV-1 which causes leukoencephalitis and arthritis in goats. A radioimmunoassay to detect CAEV p28 was used to determine the presence of the virus. Results are listed in Table Ia (c).

TABLE 1a(c)

| DRUG | | | LOG VIRUS DILUTION | | | | | TITER | PERCENT INHIBITION |
|------|---|---|---|---|---|---|---|-------|--------------------|
| | | | −1 | −2 | −3 | −4 | −5 | −6 | | |
| None | | | 2/2 | 2/2 | 2/2 | 1/2 | 0/2 | 0/2 | 3 × 10$^8$ | 0 |
| IPA | 300 | μM | 2/2 | 2/2 | 2/2 | 2/2 | 1/2 | 0/2 | 3 × 10$^6$ | 99 |
| IPA | 100 | μM | 2/2 | 2/2 | 2/2 | 2/2 | 1/2 | 0/2 | 3 × 10$^6$ | 99 |
| IPA | 30 | μM | 2/2 | 2/2 | 2/2 | 2/2 | 1/2 | 0/2 | 3 × 10$^7$ | 90 |
| IPA | 10 | μM | 2/2 | 2/2 | 2/2 | 0/2 | 0/2 | 0/2 | 1 × 10$^8$ | 67 |
| IPA | 3 | μM | 2/2 | 2/2 | 2/2 | 1/2 | 0/2 | 0/2 | 3 × 10$^8$ | 0 |
| IPA | 1 | μM | 2/2 | 2/2 | 2/2 | 1/2 | 0/2 | 0/2 | 3 × 10$^8$ | 0 |
| AZT | 100 | μM | 0/2 | 0/2 | 0/2 | 0/2 | 0/2 | 0/2 | 1 × 10$^8$ | 67 |
| AZT | 10 | μM | 0/2 | 0/2 | 0/2 | 0/2 | 0/2 | 0/2 | 3 × 10$^8$ | 0 |
| ddC | 100 | μM | 2/2 | 2/2 | 0/2 | 0/2 | 0/2 | 0/2 | <1 × 10 | 99.99 |
| ddC | 10 | μM | 2/2 | 2/2 | 1/2 | 0/2 | 0/2 | 0/2 | 3 × 10$^4$ | 99.99 |

EXPERIMENT Ia(d)

Effects of IPA, AZT and ddC on Human Cell Viability

Human peripheral blood mononuclear cells were incubated for 18 hours in the presence of various concentrations of IPA and azidothymidine (AZT) at 37° C. after which time cell viability was determined by visual counts of cells in the presence of trypan blue. The results are tabulated in Table Ia(d) (i). Two controls were run, one with each series of experiments. No toxicity was observed for AZT concentrations between 0.1 μM and 6 mM. There was a slight reduction in cell viability in the presence of 6 mM IPA, but no toxic effect was observed using concentrations of from 0.1 μM to 3 μM.

TABLE Ia(d) (i)

| Concentration (μM) | AZT 18 hours | | IPA 18 hours | |
|---|---|---|---|---|
| | Cells/ml (× 10$^5$) | Viability (%) | Cells/ml (× 10$^5$) | Viability (%) |
| 6000 | 3.8 | 95 | 2.4 | 75 |
| 3000 | 3.0 | 88 | 2.2 | 92 |
| 1000 | 2.2 | 100 | 2.8 | 82 |
| 300 | 2.4 | 92 | 2.2 | 79 |
| 100 | 2.0 | 91 | 3.8 | 90 |
| 30 | 3.0 | 100 | 3.8 | 95 |
| 10 | 1.8 | 90 | 3.0 | 94 |
| 3 | 2.0 | 100 | 2.6 | 87 |
| 1 | 1.8 | 90 | 2.8 | 100 |
| 0.3 | 2.0 | 91 | 1.8 | 82 |
| 0.1 | 3.4 | 100 | 2.4 | 86 |
| control | 3.2 | 94 | 2.6 | 87 |

Experiments were also performed to determine the toxic effect of IPA, AZT and ddC on other cell lines. The results are tabulated in Tables Ia(d) (ii) to Ia(d) (v).

Two lots of IPA (Sample 1 and Sample 2) were tested. Tests of Sample 1 over four months indicated there was no change in the compound.

TABLE Ia(d) (ii)

CELL LINE: H9, Continuous Exposure for 10 days

| DRUG | CONCENTRATION (μM) | PERCENT VIABLE CELLS |
|------|---------------------|----------------------|
| AZT | 100 | 61 |
| AZT | 10 | 77 |
| AZT | 1 | 83 |
| ddc | 100 | 68 |
| ddC | 10 | 79 |
| ddC | 1 | 93 |
| Sample 1 | | |
| IPA | 1000 | 12 |
| IPA | 300 | 18 |
| IPA | 100 | 20 |
| IPA | 30 | 56 |
| IPA | 10 | 73 |
| IPA | 3 | 84 |
| IPA | 1 | 86 |
| Sample 2 | | |
| IPA | 1000 | 7 |
| IPA | 300 | 21 |
| IPA | 100 | 23 |
| IPA | 30 | 61 |
| IPA | 10 | 78 |
| IPA | 3 | 81 |
| IPA | 1 | 84 |
| CONTROL | 1 | 87 |

TABLE Ia(d) (iii)

| | CELL LINE: H9, HIV Chronically Infected, Continuous Exposure for 4 days | |
|---|---|---|
| DRUG | CONCENTRATION (µM) | PERCENT VIABLE CELLS |
| AZT | 100 | 76 |
| AZT | 10 | 81 |
| AZT | 1 | 88 |
| ddC | 100 | 68 |
| ddC | 10 | 79 |
| ddC | 1 | 91 |
| Sample 1 | | |
| IPA | 1000 | 51 |
| IPA | 300 | 48 |
| IPA | 100 | 60 |
| IPA | 30 | 73 |
| IPA | 10 | 85 |
| IPA | 3 | 89 |
| IPA | 1 | 93 |
| Sample 2 | | |
| IPA | 1000 | 57 |
| IPA | 300 | 53 |
| IPA | 100 | 66 |
| IPA | 30 | 78 |
| IPA | 10 | 86 |
| IPA | 3 | 89 |
| IPA | 1 | 92 |
| CONTROL | | 91 |

TABLE Ia(d) (iv)

| | | CELL LINE DAYS EXPOSED TO DRUG (PERCENT VIABLE CELLS) | | | | |
|---|---|---|---|---|---|---|
| DRUG TYPE OR EXPOSURE | CONC (µM) | 1 DAY | 4 DAYS, CONT. | 10 DAYS, CONT. | 4 DAYS, 1 DAY EXP | 10 DAYS, 1 DAY EXP |
| AZT | 100 | 95 | 78 | 56 | 76 | 64 |
| AZT | 10 | 95 | 74 | 68 | 85 | 70 |
| AZT | 1 | 93 | 80 | 75 | 85 | 79 |
| ddc | 100 | 92 | 66 | 53 | 93 | 58 |
| ddC | 10 | 90 | 78 | 71 | 85 | 75 |
| ddC | 1 | 95 | 63 | 82 | 77 | 79 |
| IPA | 1000 | 58 | 52 | 18 | 73 | 38 |
| IPA | 300 | 74 | 65 | 26 | 72 | 51 |
| IPA | 100 | 66 | 60 | 34 | 84 | 59 |
| IPA | 30 | 62 | 56 | 44 | 92 | 68 |
| IPA | 10 | 81 | 85 | 70 | 84 | 79 |
| IPA | 3 | 75 | 85 | 78 | 90 | 88 |
| IPA | 1 | 80 | 84 | 81 | 89 | 81 |
| IPA | 1000 | 63 | 51 | 15 | 65 | 42 |
| IPA | 300 | 77 | 40 | 22 | 70 | 50 |
| IPA | 100 | 71 | 47 | 26 | 82 | 61 |
| IPA | 30 | 75 | 65 | 43 | 80 | 77 |
| IPA | 10 | 78 | 88 | 66 | 89 | 83 |
| IPA | 3 | 79 | 84 | 79 | 80 | 88 |
| IPA | 1 | 91 | 78 | 72 | 80 | 92 |
| CONTROL | N/A | 95 | 75 | 84 | 95 | 90 |

TABLE Ia(d) (v)

| | | MONOCYTE/MACROPHAGE CELLS | | | | |
|---|---|---|---|---|---|---|
| TYPE OR EXPOSURE DRUG | CONC. (µM) | 1 DAY | 4 DAYS, CONT. | 10 DAYS, CONT. | 4 DAYS, 1 DAY EXP | 10 DAYS, 1 DAY EXP |
| AZT | 100 | ++++ | ++++ | +++ | ++++ | +++ |
| AZT | 10 | ++++ | ++++ | ++++ | ++++ | ++++ |
| AZT | 1 | +++ | ++++ | ++++ | ++++ | ++++ |
| ddc | 100 | ++++ | ++++ | +++ | ++++ | +++ |
| ddC | 10 | ++++ | ++++ | ++++ | ++++ | ++++ |
| ddC | 1 | ++++ | ++++ | ++++ | ++++ | ++++ |
| IPA, OLD | 1000 | ++ | 0 | 0 | + | ++ |
| IPA, OLD | 300 | ++ | ++ | + | ++ | ++ |
| IPA, OLD | 100 | ++ | ++ | ++ | +++ | +++ |
| IPA, OLD | 30 | +++ | ++ | ++ | +++ | +++ |
| IPA, OLD | 10 | +++ | +++ | +++ | ++++ | ++++ |
| IPA, OLD | 3 | ++++ | +++ | +++ | ++++ | ++++ |
| IPA, OLD | 1 | ++++ | ++++ | ++++ | ++++ | ++++ |
| IPA, NEW | 1000 | ++ | 0 | 0 | + | ++ |
| IPA, NEW | 300 | ++ | ++ | + | ++ | ++ |
| IPA, NEW | 100 | ++ | ++ | ++ | +++ | +++ |
| IPA, NEW | 30 | +++ | ++ | ++ | +++ | +++ |
| IPA, NEW | 10 | +++ | +++ | +++ | ++++ | ++++ |
| IPA, NEW | 3 | ++++ | +++ | +++ | ++++ | ++++ |
| IPA, NEW | 1 | ++++ | ++++ | ++++ | ++++ | ++++ |
| CONTROL | N/A | ++++ | ++++ | ++++ | ++++ | ++++ |

Note: since monocyte/macrophage cells are tightly adherent to the wells, they cannot be trypsinized to stain and count. We were also unable to effectively observe dye uptake directly in the well, so the observations made above represent qualitative indications of the apparent health of the cells as well as the cell numbers.

Nevertheless, it is important to note that these monocyte/macrophage cells appear to be far more resistant to the toxic effect of IPA than the T cell lines, for example. Since the tahr cells used for CAEV testing were also relatively resistant to IPA, it may be that the most rapidly growing cells are most vulnerable.

Experiment 1a(e)

Effects of Drugs on Human T and B Lymphocyte Function

Tests were carried out to determine the effect of compound Ia on normal human T and B lymphocyte functions.

T and B lymphocytes from normal human donors were incubated for 30 minutes at various dose levels of the compounds indicated. The lymphocytes were added in triplicate wells in gentamicin and phytohemagglutinin (PHA) (a T cell mitogen), pokeweed mitogen (PWM) (a B cell mitogen) and allogeneic mononuclear cells (mixed leukocyte cultures; MLC) or media containing the above additives. The lymphocyte blastogenesis assay is described in detail below.

The results of the various assays are summarized in Charts Ia(e) (i)–Ia(e) (xii) (FIGS. 1-12). Enhanced blastogenesis of cells was interpreted to indicate stimulation of cell activity.

Figure 2:
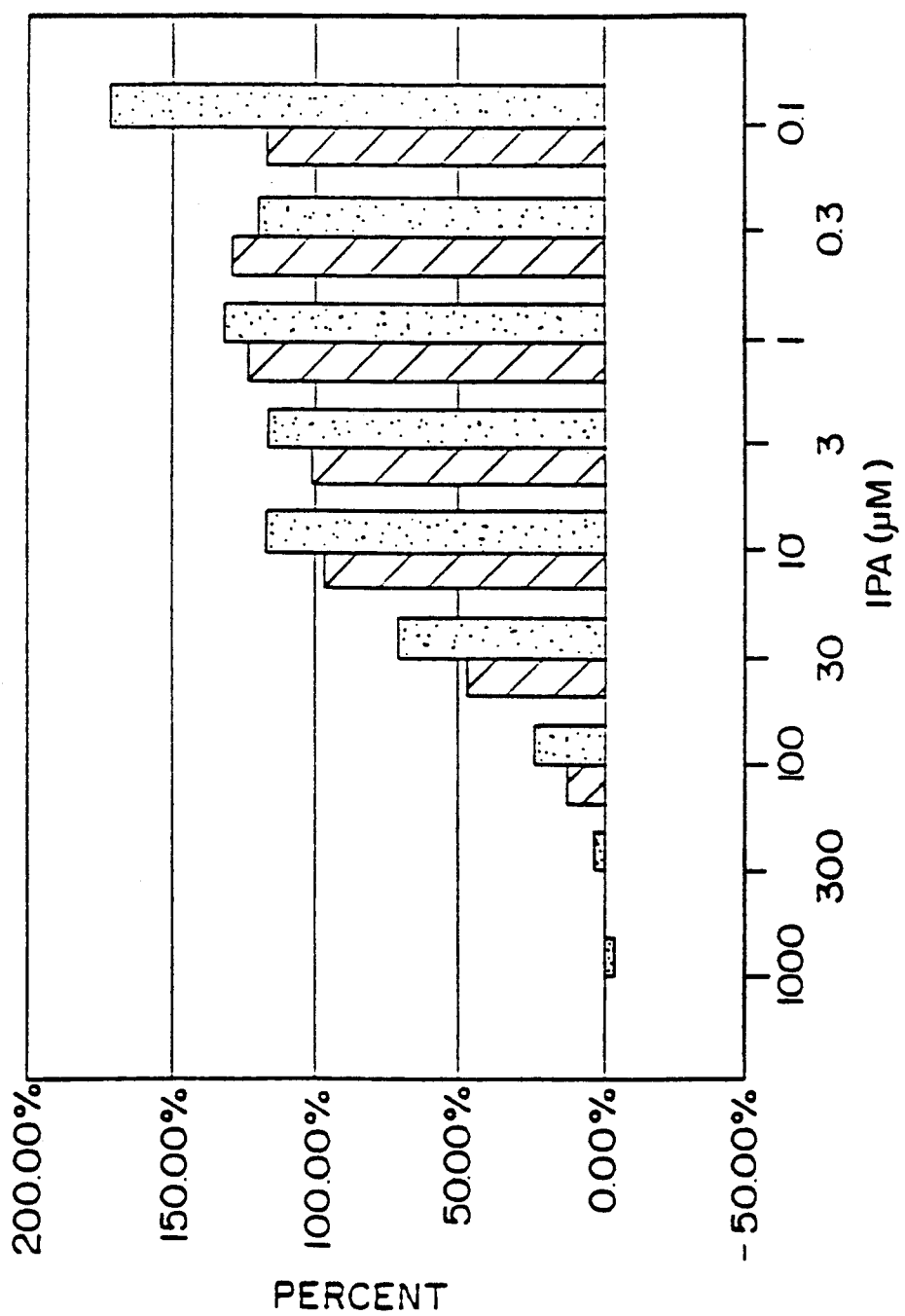
FIG. 2 is a graph of percentage increase or decrease in proliferation capability versus concentration of IPA in an assay.

The data are represented as the mean of the three replicates. The results are presented in Charts Ia(e) (i) and Ia(e) (ii) (FIGS. 1 and 2). Chart Ia(e) (i) (FIG. 1) presents the data as net counts per minute (CPM) (mean CPM in mitogen containing wells) and Chart Ia(e) (ii) (FIG. 2) shows a percentage increase or decrease (% change=(net CPM of wells with IPA/net CPM of wells with media)×100) in proliferation capability in cell cultures in which IPA was added as compared to cell cultures without IPA. A reduction of both T lymphocytes' abilities to proliferate was obtained when 100 $\mu$M or greater concentrations of IPA was added to the cell cultures. Proliferative activity of T lymphocytes by 25% at the 30 $\mu$M concentration of IPA in the experiment. No effect or an increase in T and B lymphocyte proliferation was observed when 0.1-10 $\mu$M concentrations of IPA were added to the cell cultures.

Figure 3:
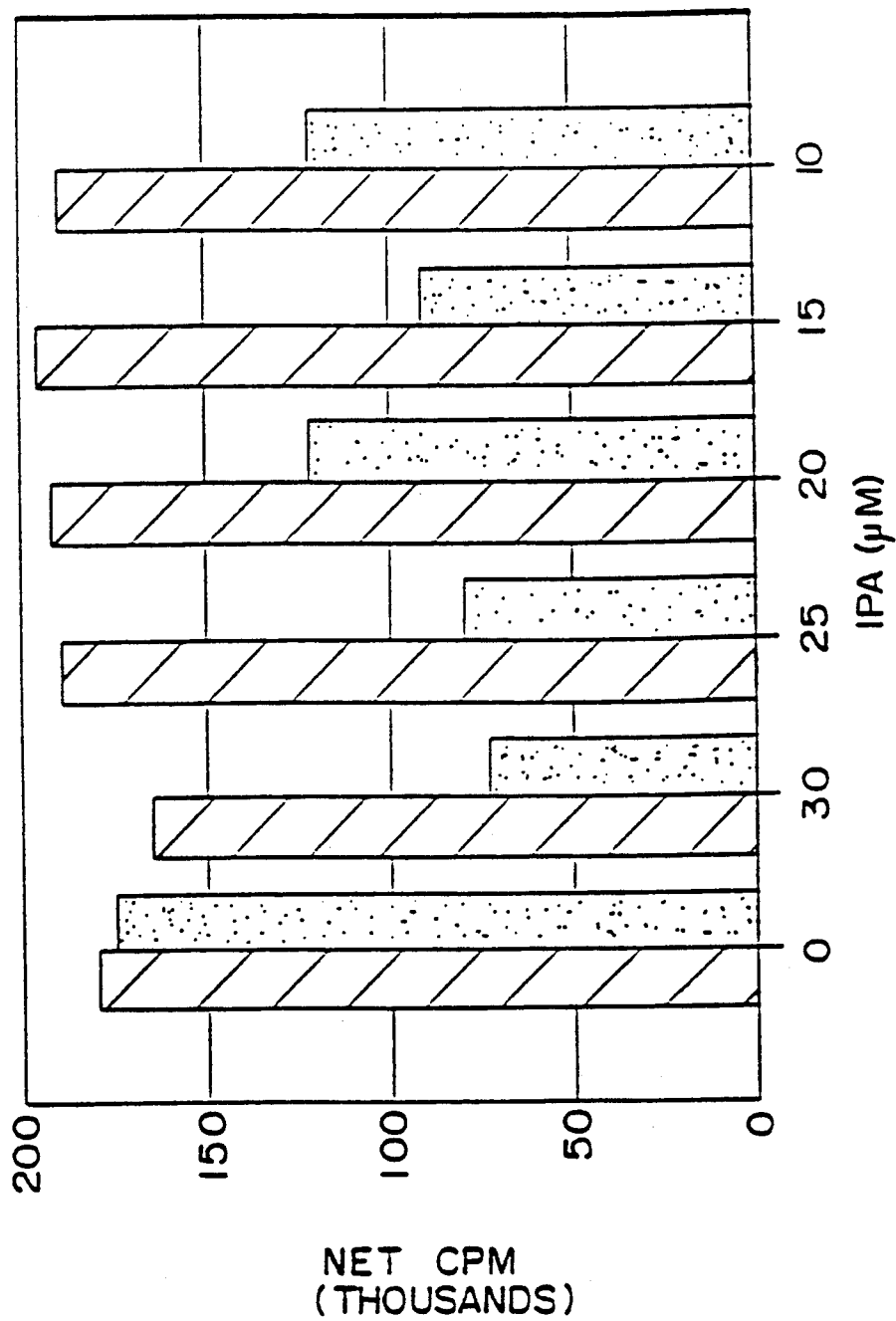
FIG. 3 is a graph of counts per minute versus concentration of IPA in an assay.
Figure 4:
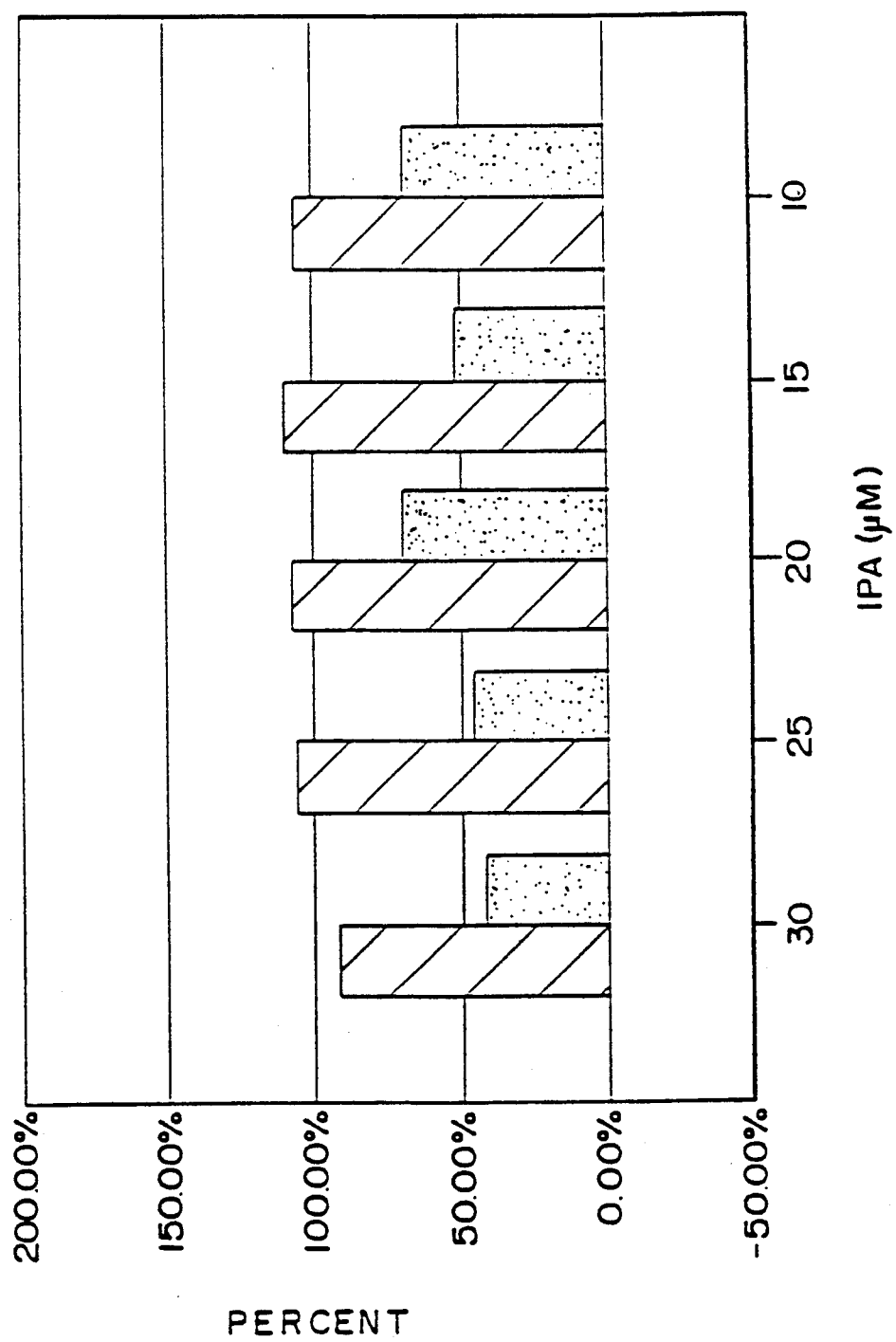
FIG. 4 is a graph of percentage increase or decrease of T and B lymphocyte proliferation versus concentration of IPA in an assay.

A second experiment was conducted where a more narrow dose level range of IPA was added to cell cultures and T and B lymphocyte proliferation was measured (Charts Ia(e) (iii) and Ia(e) (iv)—FIGS. 3 and 4). No appreciable reduction in T lymphocyte proliferation was observed with dose levels of IPA ranging from 30 down to 10 $\mu$M. An approximate reduction of B lymphocyte proliferation of 30-50% was observed between the 30-10 $\mu$M concentration levels. The degree of variation observed between experiments is common in these tests. (Luster, et al. Development of a Testing Battery to Assess Chemical-Induced Immunotoxicity: National Toxicology Program's Guidelines for Immunotoxicity Evaluation in Mice).

Figure 5:
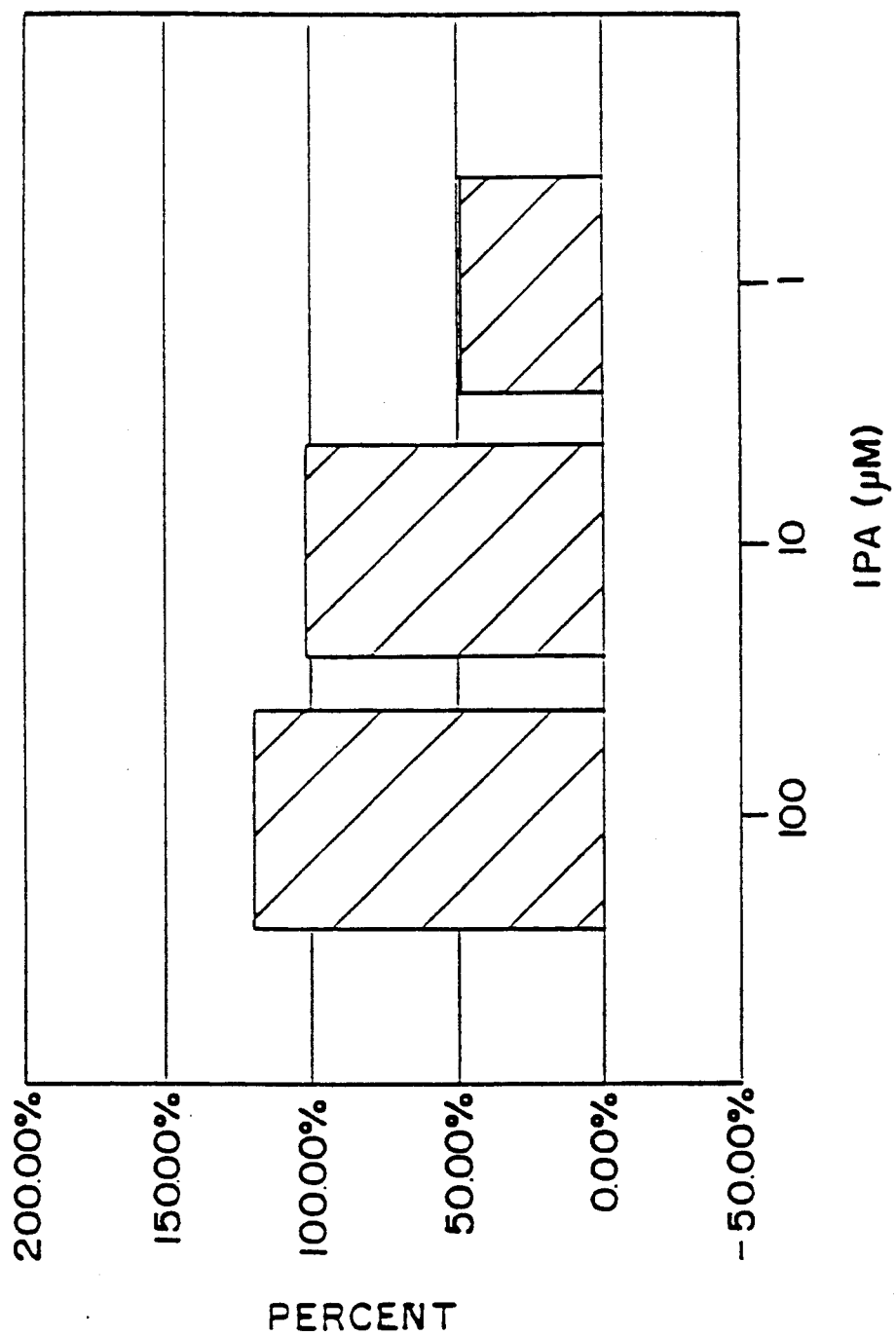
FIG. 5 is a graph of percentage increase or decrease of MLC reactivity versus concentration of IPA in an assay.
Figure 6:
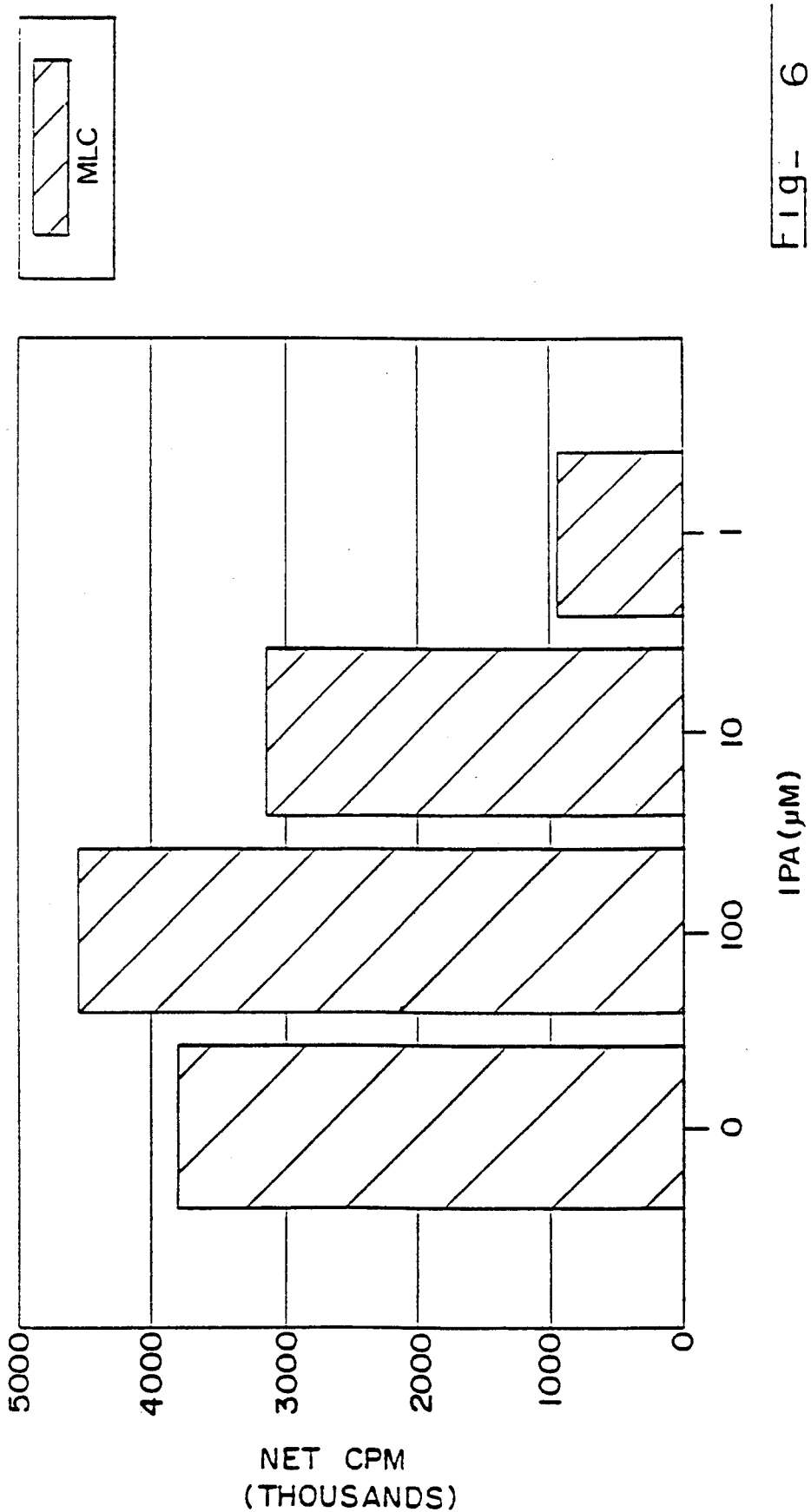
FIG. 6 is a graph of counts per minute versus concentration of IPA in an assay.
Figure 7:
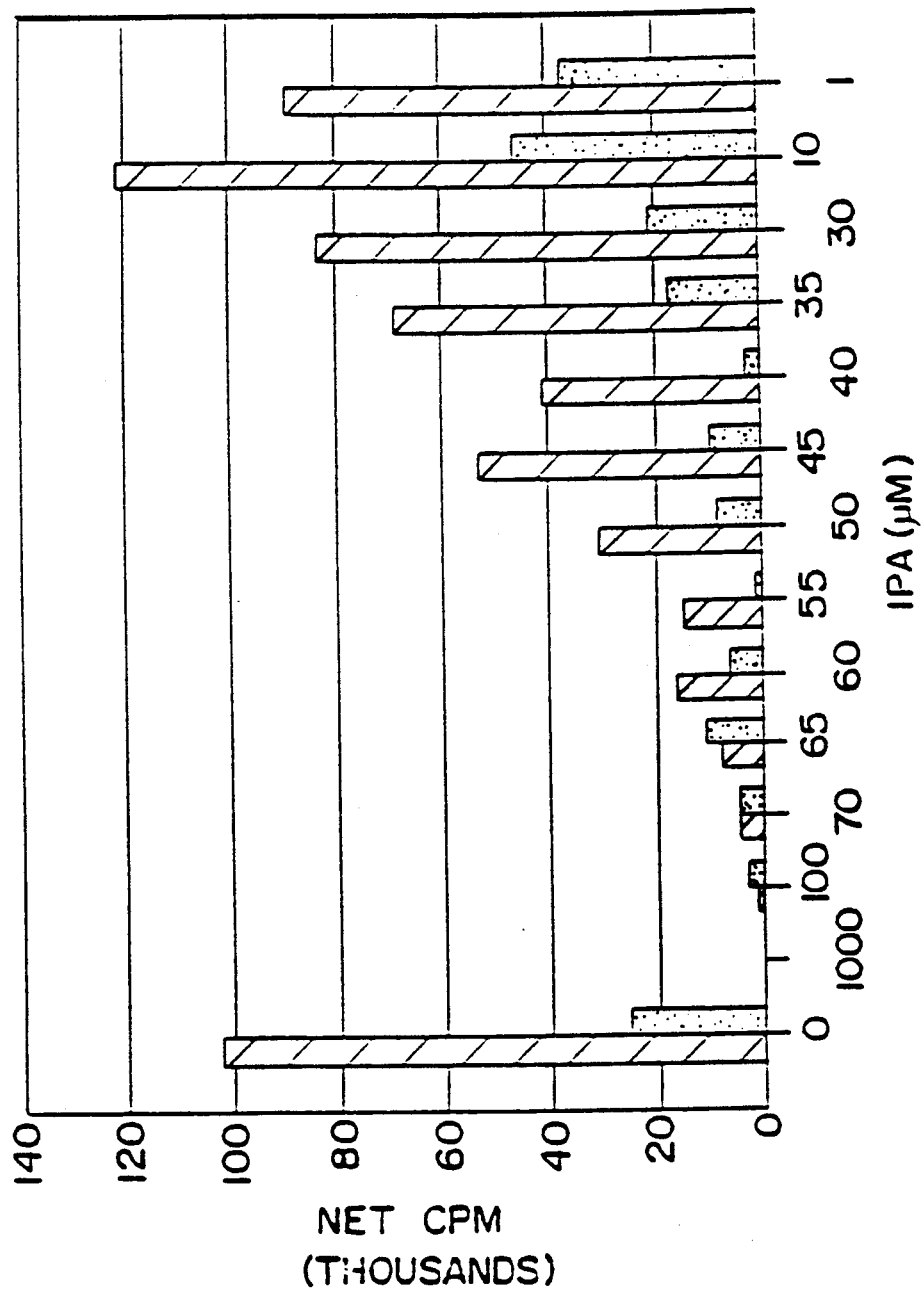
FIG. 7 is a graph of counts per minute versus concentration of IPA in an assay.
Figure 8:
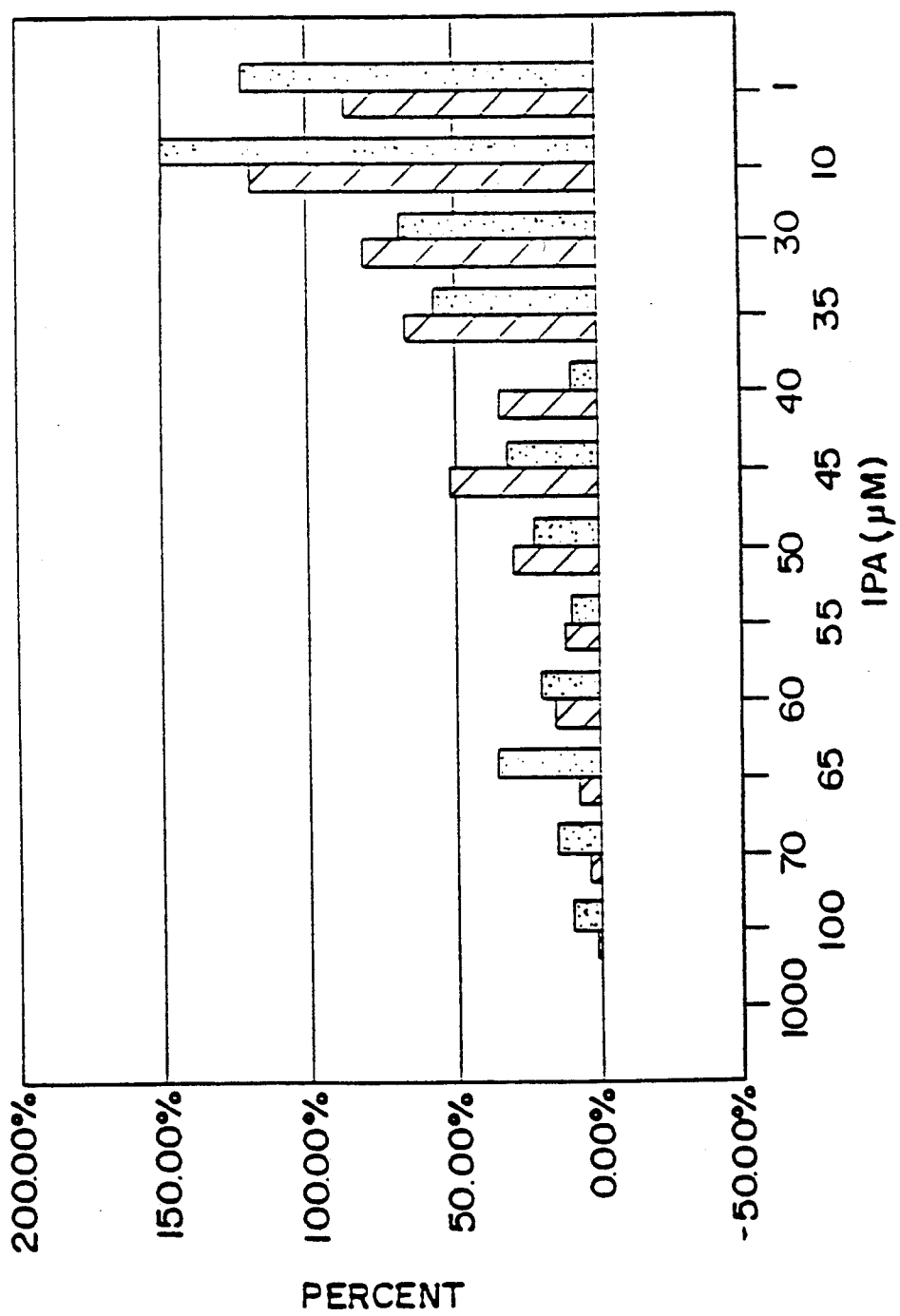
FIG. 8 is a graph of percentage increase or descrease of T and B lymphocyte function versus concentration of IPA in an assay

Mixed leukocyte culture (MLC) reactions may be used to evaluate the ability of human mononuclear cells to recognize and immunologically react to human histocompatibility antigen (measurement of the ability of the cells to mount a primary immune response to an antigen). Cultures of one set of human mononuclear cells were reacted with mononuclear cells from an unrelated donor in lymphocyte blastogenesis assays and the proliferation of the first set of cells was quantitated. The results are presented in Charts Ia(e) (v) and Ia(e) (vi) (FIGS. 5 and 6). Again, as with lymphocyte blastogenesis with mitogens, the MLC was run in replicates of three and a mean value obtained. A slight increase in MLC reactivity was seen when 100 $\mu$M of IPA were added to the cultures. No effect on MLC reactivity was seen with 10 $\mu$M of IPA and a 50% reduction in MLC reactivity was obtained at the 1 $\mu$M concentration.

To more closely observe the "no effect" dose level of IPA on T and B lymphocyte function, an experiment was conducted where very close dose level intervals were run in lymphocyte blastogenesis assays. Within this experiment, the comparative effects of wide dose levels (1000-1 $\mu$M of AZT and ddC were also evaluated on T and B lymphocyte function. The results are shown in Charts Ia(e) (vii)–Ia(e) (xii) (FIGS. 7-12). Again, reductions in T and B lymphocyte function were obtained with IPA at dose levels ranging from 1000 $\mu$M down to 10 $\mu$M. An approximate 25% reduction in both T and B lymphocyte function was seen at the 30-35 $\mu$M concentration of IPA (Charts Ia(e) (vii) and Ia(e) (viii)—FIGS. 7 and 8). Increased T and B lymphocyte responsiveness was observed at the 10 $\mu$M dose level.

Figure 9:
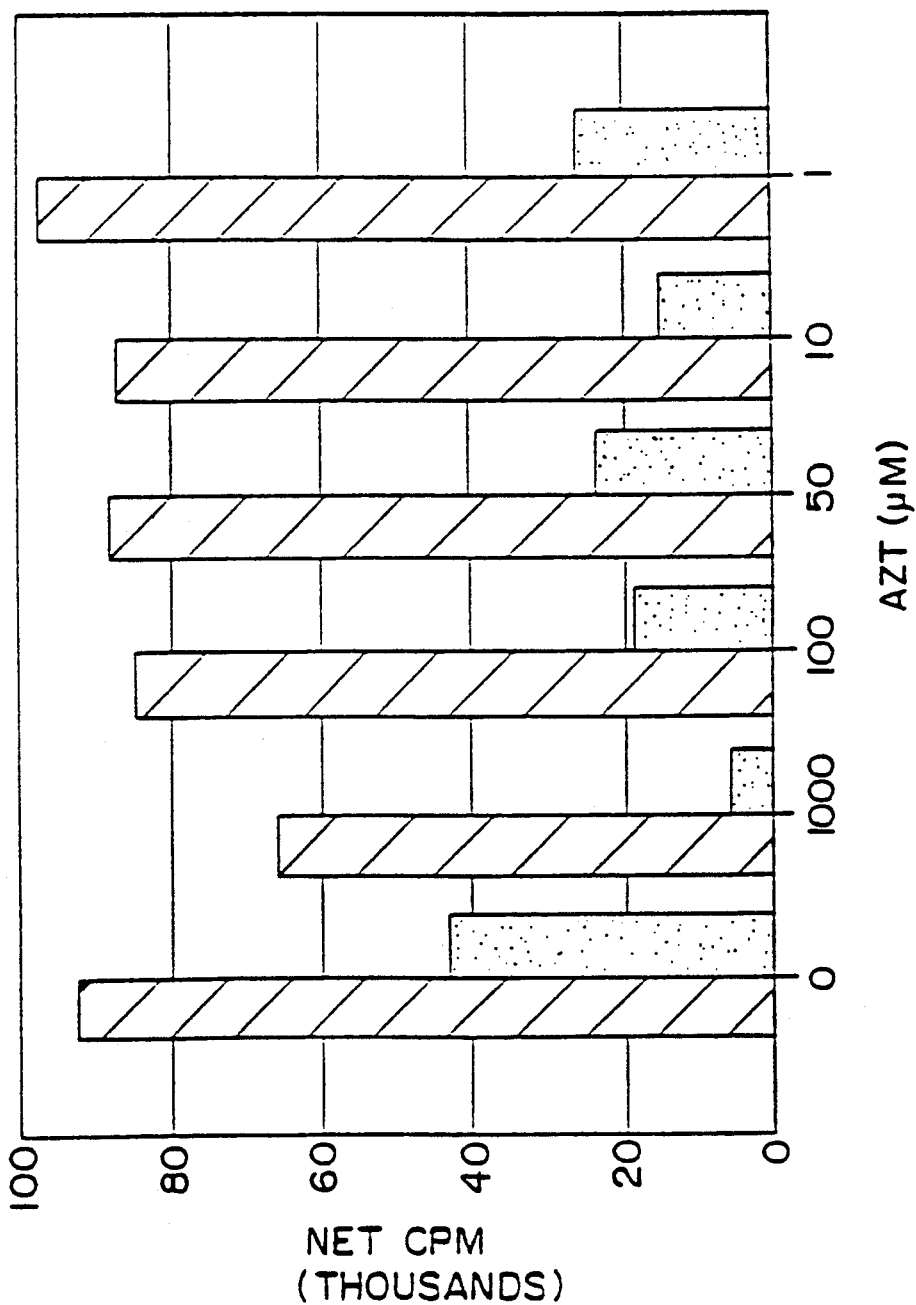
FIGS. 9 and 10 are graphs of T lymphocyte proliferation versus concentration of AZT in an assay.
Figure 10:
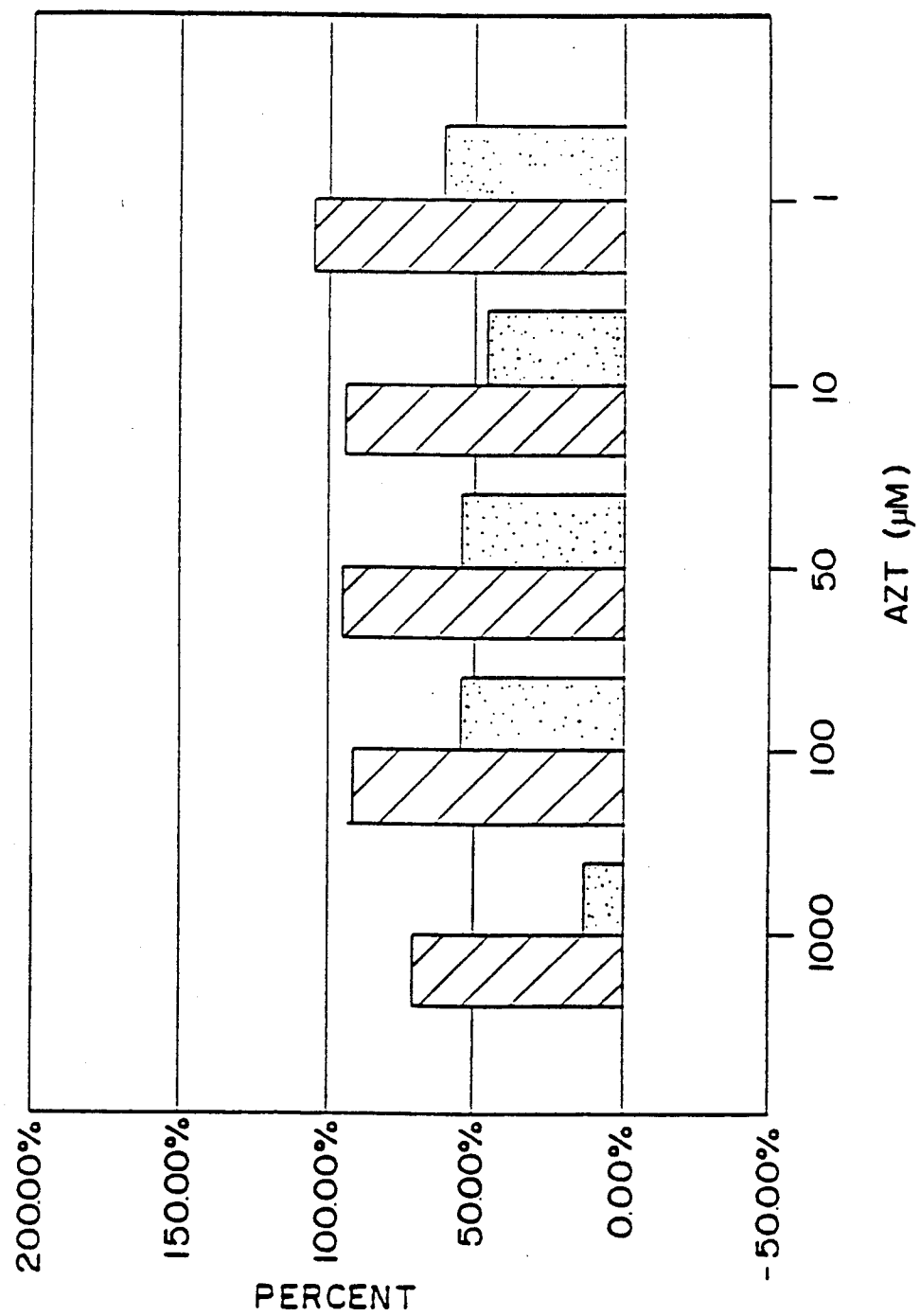
Figure 11:
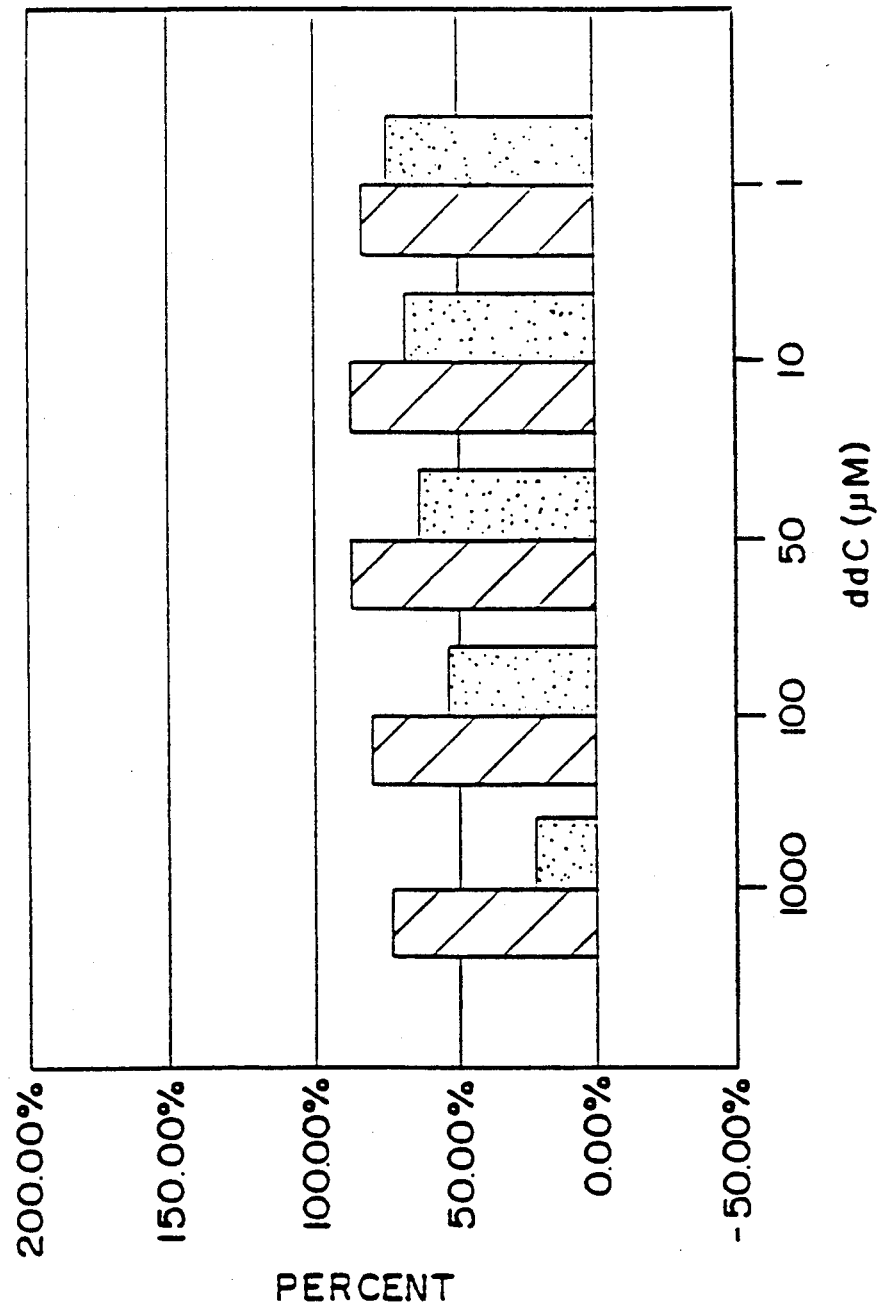
FIGS. 11 and 12 are graphs of T lymphocyte function versus concentration of ddC in an assay.
Figure 12:
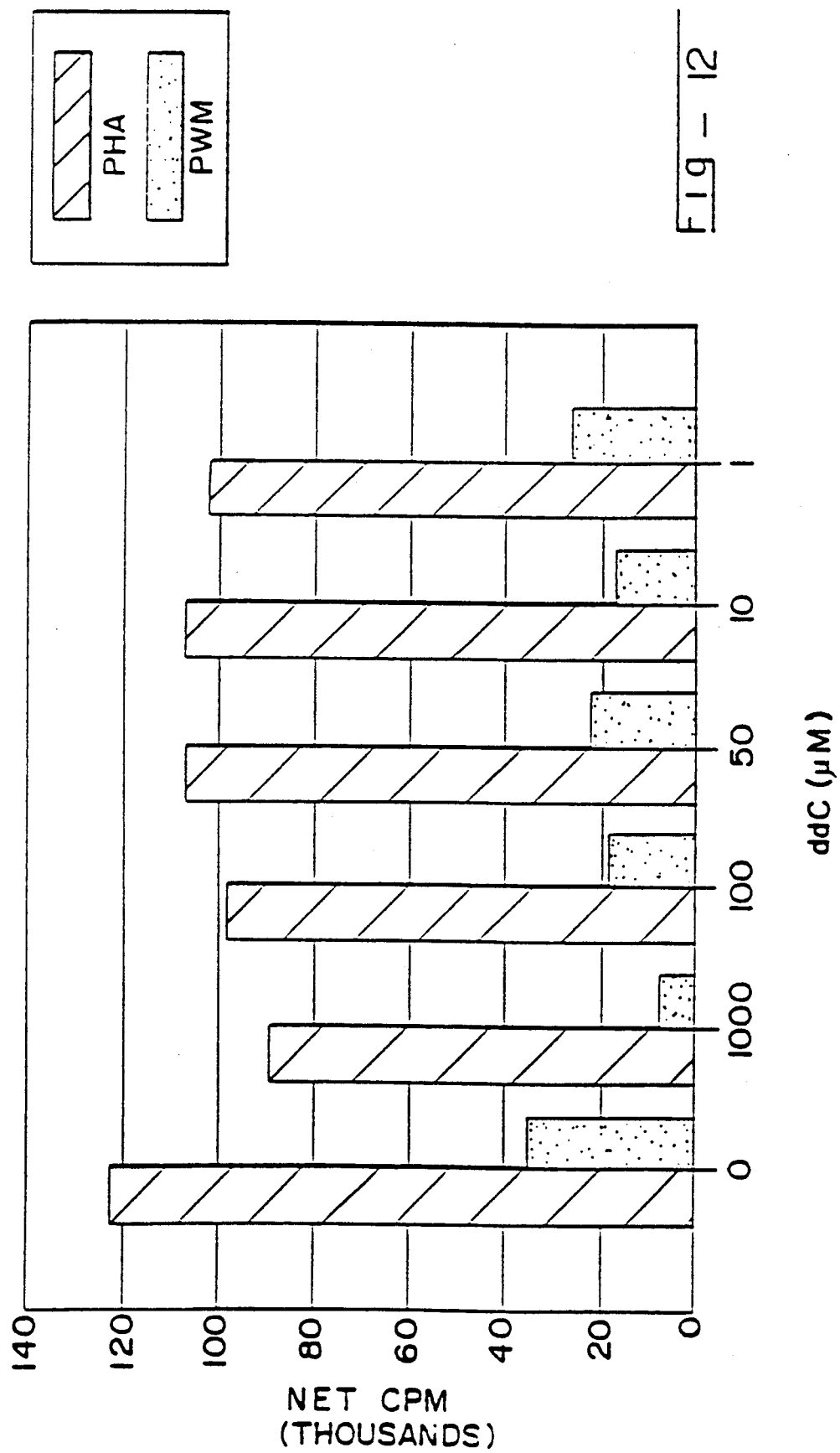

No appreciable decrease in T lymphocyte proliferation was obtained at 100-1 $\mu$M concentrations of AZT (Charts Ia(e) (ix) and Ia(e) (x)—FIGS. 9 and 10); an approximate 25% reduction was seen at the 1000 $\mu$M dose level of AZT on T cells. AZT at all dose levels, 1000-1 $\mu$M, caused decreases in B lymphocyte proliferation (50-90%) reduction.

A reduction of 10-25% in T lymphocyte function was seen with a wide range (100-1 $\mu$M) of dose levels of ddC. As with AZT, larger reductions in B lymphocyte proliferative responses were observed with ddC. At the 1000 $\mu$M concentration, an 80 to 85% reduction was seen, and a 20-35% reduction was obtained at the 1 $\mu$M dose level of ddC (Charts Ia(e) (xi) and Ia(e) (xii)—FIGS. 11 and 12).

EXPERIMENT Ia(f)

Effects of Drugs on Human Monocyte Function

Monocytes from each human donor were incubated for 30 minutes with three different dose levels of compound Ia in triplicate. These cells were added to agarose and droplets of agarose containing cells were added to small chambers. A chemotaxis agent was added to induce enhanced migration of the mononuclear cells. The detailed assay procedures are described below.

Cell migration patterns of triplicates within 30% of each other were generally accepted. Results are listed in Table Ia(f)(i).

TABLE Ia(f) (i)

| Concentration of IPA ($\mu$M) | Spontaneous Migration % Change in Migration Versus Media Control (+ or −) | Chemotactic Migration (Response to f-met-lue-phe) % Change in Migration Versus Media Control with f-met-leu-phe (+ or −) |
|---|---|---|
| 1000 | −29% | — |
| 300 | −22% | — |
| 100 | −37% | −71% |
| 30 | −15% | −65% |
| 10 | −2% | −55% |
| 3 | +14% | −45% |
| media | — | — |
| 1 | −73% | −16% |
| 0.3 | −51% | +12% |

TABLE Ia(f) (i)-continued

| Spontaneous Migration | | Chemotactic Migration (Response to f-met-lue-phe) |
| --- | --- | --- |
| Concentration of IPA (μM) | % Change in Migration Versus Media Control (+ or −) | % Change in Migration Versus Media Control with f-met-leu-phe (+ or −) |
| 0.1 | −31% | — |
| media | — | — |

+ = Increased
− = Decreased

There was a 22-37% reduction in the ability of the monocytes to spontaneously migrate using 100-1000 μM concentrations of IPA. There was a smaller 15% reduction in spontaneous migration at the 30 μM concentration of IPA. Enhanced spontaneous migration was observed using 0.1-0.3 μM of IPA.

The effect of IPA was studied using concentrations of IPA surrounding the initially observed transition level of from 3-30 μM. The results are tabulated in Table Ia(f)(ii).

TABLE Ia(f) (ii)

| Concentration of IPA (μM) Control | Total Area (mm²) Migration | % Change in Migration with IPA Versus Media |
| --- | --- | --- |
| 30 | 5795 | −34% |
| 25 | 6435 | −26% |
| 20 | 6804 | −22% |
| media | 8732 | — |
| 15 | 6300 | −31% |
| 10 | 6846 | −25% |
| 5 | 7952 | −12% |
| media | 9085 | — |

+ = Increased
− = Decreased

As can be seen from Tables Ia(f) (i) and Ia(f) (ii), the degree of decrease in spontaneous migration of cells in the presence of IPA varies somewhat between the two sets of experiments. For example, a 15% decrease was observed in the migration of cells at 30 μM IPA (Table Ia(f) (ii) and a 34% decrease is shown in Table Ia(f) (ii). This size of variation is normal for this type of assay. (Luster, et al, ibid).

The relative effects of AZT and ddC were also studied. The results are tabulated in Table Ia(f) (iii).

TABLE Ia(f) (iii)

COMPARATIVE ABILITIES OF HUMAN MONOCYTES TO FUNCTION (SPONTANEOUSLY MIGRATE) FOLLOWING TREATMENT WITH IPA, AZT, AND ddC

| | % Change in Migration Versus Media Control | | |
| --- | --- | --- | --- |
| Concentration | IPA | AZT | ddC |
| 1000 | −52% | −58% | −44% |
| 100 | −36% | −59% | −22% |
| 70 | −41% | — | — |
| 65 | −41% | — | — |
| 60 | −36% | — | — |
| 55 | −41% | — | — |
| 50 | −45% | −57% | −41% |
| 45 | −49% | — | — |
| 40 | −51% | — | — |
| 35 | −52% | — | — |
| 30 | −40% | — | — |
| 10 | +8% | −31% | −45% |
| 1 | +14% | −28% | −36% |

+ = Increased
− = Decreased

DETAILED DESCRIPTION OF HUMAN LYMPHOCYTE BLASTOGENESIS ASSAY

1. Mononuclear cells are separated from whole blood by differential centrifugation using a synthetic separation medium, or are thawed from a cryopreserved preparation. The cells are washed and resuspended in media (RPMI - 1640, L-Glutamine 2 mM, Herpes Buffer 25 mM, Gentamicin 50 ug/ml, Human AB Serum-heat inactivated (56°, 30°) 20%).
2. A viable cell count is determined.
3. Cell concentration is adjusted to $2 \times 10^6$/ml in media.
4. The cell suspension is added to wells of a 96-well flat bottom plate in 0.1 ml aliquots ($2 \times 10^5$ cells).
5. The selected mitogens and/or antigens (in media without serum) are added to the cells in the wells also in 0.1 ml aliquots.
6. The cultures are incubated for 3-7 days (depending upon the mitogen or antigen) at 37° C. in a humidified 5% $CO_2$ atmosphere.
7. Six to eight hours before termination of cultures 0.05 ml (1 μCi) of $^3$HTdR sp. act 6.7 Ci/mM (20 μCi/ml stock) is added to each well.
8. At termination of cultures the cells are harvested onto strips of scintillation-grade fiberglass paper using a multiple sample harvester.
9. Perforated disks from the fiberglass paper of the harvested cultures are placed each into scintillation vials to which is then added 5 ml of toluene based scintillation cocktail.
10. The vials are counted in a liquid scintillation counter for one minute where the amount of incorporated $^3$HTdR is determined.

CALCULATION OF RESULTS net CPM = xCPM of mitogen/antigen cultures - xCPM of media cultures.

$$\% \text{ change} = \frac{\text{net } CPM \text{ of test individual}}{\text{net } CPM \text{ of normal individual}} \times 100$$

ISOLATION OF MONOCYTES USING PERCOLL GRADIENT SEPARATION

1. Add 6 ml Phosphate Buffered Saline (PBS) 2X to 7 ml of Percoll.
2. Add mixture to 15 ml polycarbonate centrifuge tubes (Sorvall *03243, 18×100 mm, pt. *00770 50/box, w/caps).
3. Centrifuge tubes at 21,000×g for 45 minutes (Sorvall, RC2-B centrifuge w/SS-34 rotor, 34 fixed angle, −15,000 rpm w/brake off @4° C.). Percoll gradient is good for two weeks.
4. Mononuclear cells are separated from whole blood by differential centrifugation using a synthetic separation medium.
5. Cells are washed 2× with Basal Salt Solution (BSS).
6. Resuspend cells in BSS +10% BCS, then add mixture to 50 ml centrifuge tubes containing 30-40 ml of Bovine Calf Serum (BCS) and centrifuge at 400×g for 10 minutes.
7. Resuspend cells in BSS without BCS.
8. Determine viable cell number.
9. Adjust concentration of cells to $2.0-2.5 \times 10^4$/ml.
10. Carefully layer 2 ml of cells on top of Percoll gradient. Centrifuge tubes at 100×g for 20 minutes at 4° C. with brake off.

11. Monocyte layer is harvested with a pasteur pipet and aliquoted into a 50 ml centrifuge tube. Dead cells are in the top band. Monocytes are about 5 ml above middle gradient. Lymphocytes are about 5 ml below middle gradient. Do not aliquot more than 6 Percoll gradient tubes of moncytes into one 50 ml centrifuge tube.
12. Wash cells 3× in BSS without BCS.
13. Resuspend cells in desired media.
14. Perform esterase stain on monocyte cell suspension to determine ratio of monocytes. Ratio ranges from 50–80%.

CHEMOTAXIS ASSAY

1. A 0.4% solution of Agarose (Seakem HE) and distilled $H_2O$ is prepared, aliquoted into 1 dram vials, autoclaved and stored at 4° C. until used.
2. A suspension of $3 \times 10^2$/ml cells in Media 199 2× containing glutamine 2 mM, gentamicin 50 g/ml and bovine calf serum-heat inactivated (56° C., 30° C.) 20%, is combined with an equal amount of 0.4% Agarose.
3. A 5 μl droplet of cell/agarose mixture is added to the center of a Sterilin plate (Surrey, England).
4. A 2 μl droplet of agarose/media mixture is added 3–5 mm to one side of the cell/agarose droplet and a 2 μl droplet of agarose/chemo-attractant (N-formyl-L-methionyl-L-Leucyl-L-Phenylalanine $10^{-4}$ M(F-Met-Leu-Phe)) is added 3–5 mm to the other side of the cell/agarose droplet.
5. The droplets are allowed to solidify, after which 0.5 ml of RPMI-1640 containing glutamine 2 mM, gentamicin 50, μg/ml and bovine calf serum 10% is added to the well. A cover slip is then placed over the well.
6. The plate is incubated at 37° C., 5% $CO_2$/air humidified for approximately 18 hours.
7. The plate is removed from the incubator and the distance the cells have moved towards the media control and the chemoattractant droplets is traced and measured.

EXPERIMENT Ia(g)

M413 Cells, CMV, Visual Method

Confluent monolayers of M413 cells (a type of dipliod human fibroblast cells) in 48 well microtiter plates were used. They were grown in Dulbecco's MEM (minimum essential medium) supplemented with 10% fetal bovine serum and 50 μg/ml gentamicin.

Stock cytomegalovirus (CMV) was diluted in a series of 10-fold dilutions in the above medium, and 0.1 millimolar amounts were added to the wells of the microtiter plates and allowed to absorb virus for 90 minutes at 37° C.

Unabsorbed virus was removed by aspiration and 0.5 ml of medium containing dilutions of drug was added to duplicate wells at each concentration of virus.

After incubating for 5 days, fresh medium was added to each well, no additional drug being included, and the plates were scored for cytopathic effects the next day. The viruses produce characteristic enlarged rounded cells in a cellular background that is completely devoid of such cells.

The data were expressed as the reciprocal of the greatest dilution producing any of the characteristic rounded cells (the "titer"), and the percent inhibition was calculated by comparing the experimental titer with the control titer, with intermediate results interpreted as those of Experiment Ia(a). The results are summarised in Table Ia(g).

Experiments were carried out to determine the viability of uninfected cells under the conditions of these experiments.

Uninfected cells were exposed to different concentrations of IPA and their viability was determined 24 hours later, relative to control cells, by trypan blue exclusion.

TABLE Ia(g)

| Concentration of IPA | Titer | Percent Inhibition | Percent Viable Cells |
|---|---|---|---|
| 0 | $3 \times 10^3$ | | 94 |
| 1000 μM | <10 | >99.7 | 23 |
| 300 μM | $3 \times 10$ | 99 | 50 |
| 100 μM | $3 \times 10^2$ | 90 | 75 |
| 30 μM | $3 \times 10^3$ | 0 | 90 |
| 10 μM | $3 \times 10^3$ | 0 | 95 |

EXPERIMENT Ia(h)

M413 Cells, HSV-I, Visual Method

A procedure similar to that described for Experiment Ia(g) was followed except herpes simplex virus-type I (HSV-I) was used. The results are given in Table Ia(h).

Experiments to determine the viability of uninfected cells under these conditions were carried out and are listed in Table Ia(g).

TABLE Ia(h)

| Concentration of IPA | Titer | Percent Inhibition (HERPES SIMPLEX TYPE-1) |
|---|---|---|
| 0 | $3 \times 10^4$ | |
| 1000 μM | <10 | >99.97 |
| 300 μM | <10 | >99.97 |
| 100 μM | $3 \times 10$ | 99.9 |
| 30 μM | $3 \times 10^4$ | 0 |
| 10 μM | $3 \times 10^4$ | 0 |

EXPERIMENT Ia(i)

P₃HR1 Cells acutely infected with EBV, Immunofluorescence

Experiments were carried out using concentrated P₃HR1 Cells. The virus was titered by superinfection of the Raji cell line which contains EBV genomes but which does not express any EBV proteins except the nuclear antigen (EBNA). Infection of Raji cells by infectious EBV induces early antigen (EA) in the cells in proportion to the titer of infectious virus. EA was detected using a monoclonal antibody.

The assay was set up with Raji cells exposed for 2 hours to serial 10 fold dilutions of the P₃HR1 virus. Excess virus was separated by centrifugation and removed. Aliquots of cells infected at each dilution were distributed into 12 well trays (0.5 ml/well), and 0.5 ml of medium containing twice the desired final medium concentration was add to each well.

At 24 and 72 hours, aliquots of each well were washed, added to Teflon ® outlined wells on a glass slide, air dried to attach them to the glass, and then fixed with acetone-methanol (50:50). Standard immunofluorescence procedures were followed to quantify the percent of cells containing virus at each time, virus dilution and drug concentration. The results are presented in Table Ia(i).

TABLE Ia(i)

| Concentration of IPA | Virus Dilution | Percent Positive 24 Hours | Cells 72 hours | Titer at 72 Hours |
|---|---|---|---|---|
| 0 | $10^{-1}$ | 50* | 65 | $10^6$ |
|  | $10^{-2}$ | 13 | 25 |  |
|  | $10^{-3}$ | 3 | 10 |  |
|  | $10^{-4}$ | 1 | 5 |  |
|  | $10^{-5}$ | 0 | 1 |  |
|  | $10^{-6}$ | 0 | <1 |  |
| 1000 μM | $10^{-1}$ | 0 | <1 |  |
|  | $10^{-2}$ | 0 | <1 |  |
|  | $10^{-3}$ | 0 | <1 |  |
|  | $10^{-4}$ | 0 | <1 |  |
|  | $10^{-5}$ | 0 | 0 |  |
|  | $10^{-6}$ | 0 | 0 |  |
| 300 μM | $10^{-1}$ | 2 | 7 | $10^5$ |
|  | $10^{-2}$ | 1 | 7 |  |
|  | $10^{-3}$ | <1 | 3 |  |
|  | $10^{-4}$ | 0 | <1 |  |
|  | $10^{-5}$ | 0 | <<1 |  |
|  | $10^{-6}$ | 0 | 0 |  |
| 100 μM | $10^{-1}$ | 6 | 15 | $10^6$ |
|  | $10^{-2}$ | 3 | 10 |  |
|  | $10^{-3}$ | <1 | 2 |  |
|  | $10^{-4}$ | 0 | 1 |  |
|  | $10^{-5}$ | 0 | <1 |  |
|  | $10^{-6}$ | 0 | <1 |  |
| 30 μM | $10^{-1}$ | 10 | 20 | $10^6$ |
|  | $10^{-2}$ | 3 | 10 |  |
|  | $10^{-3}$ | 1 | 7 |  |
|  | $10^{-4}$ | <1 | 4 |  |
|  | $10^{-5}$ | 0 | <1 |  |
|  | $10^{-6}$ | 0 | <1 |  |
| 10 μM | $10^{-1}$ | 17 | 28 | $10^6$ |
|  | $10^{-2}$ | 8 | 15 |  |
|  | $10^{-3}$ | 2 | 8 |  |
|  | $10^{-4}$ | <1 | 5 |  |
|  | $10^{-5}$ | 0 | <1 |  |
|  | $10^{-6}$ | 0 | <1 |  |

These percentage values were obtained by counting about 200 cells at each point and calculating the percentage of cells that are antigen positive.

EXPERIMENT Ia(i)

M413 Cells, HSV-1, Immunofluorescence Assay

The experiments were performed in duplicate M413 cells which were set up in Titer-Tek slides (4 well, glass) and those that were confluent within one day were used in experiments. Within 24-48 hours, cell densities were checked to ensure sufficiency to proceed with infection. Stock HSV-1 was serially diluted in 10-fold steps (1, $10^{-1}$, $10^{31\ 2}$, $10^{-3}$, $10^{-4}$) to provide 2 ml of each dilution: 0.2/1.8 ml diluent to finally yield overall dilutions of approximately $10^{-1}$, $10^{-2}$, $10^{-3}$, $10^{-4}$, $10^{-5}$. Virus absorption was allowed for 90 minutes at 37° C., after which time the inoculum was removed and replaced with solutions containing IPA at the concentrations as indicated in Table Ia(j). The slide was incubated for 3 days and stained with the following antisera: monoclonal antibody (MAB) to HSV-1 virus capsid antigen (VCA) at 1:20; control mores IgG at 1:20. The results are reported in Table Ia(j).

TABLE Ia(j)

| Concentration | Log Virus Dilution | | | | |
|---|---|---|---|---|---|
|  | −1 | −2 | −3 | −4 | −5 |
| Controls (no IPA): |  |  |  |  |  |
| MAB-VCA | 2.5 | 2 | 2 | 2 | 0.5 |
| Normal Mouse IgG | 0 | 0 | 0 | 0 | 0 |
| Unifected MAB-VCA | 0 |  |  |  |  |
| 1000 μM | 0 | 0 | 0 | 0 | 0 |
| 300 μM | 0 | 0 | 0 | 0 | 0 |
| 100 μM | 0 | 0 | 0 | 0 | 0 |
| 30 μM | 0 | 0 | 0 | 0 | 0 |
| 10 μM | 0 | 0 | 0 | 0 | 0 |
| 3 μM | 0 | 0 | 0 | 0 | 0 |
| 1 μM | 0.25 | 0.25 | 0.25 | 0.25 | 0.25 |

A similar series of tests were performed using acycloguanosine (Acyclovir) for comparison purposes. These results are shown in Table Ia(jb).

TABLE Ia(jb)

Immunofluorescence measurment of HSV-1 grown on human fibroblasts and exposed to Acyclovir.

| CONC. | IMMUNOFLUORESCENCE AT A VIRUS DILUTION OF: | | | | | TITER |
|---|---|---|---|---|---|---|
|  | −3 | −4 | −5 | −6 | −7 |  |
| NONE | 4+/4+ | 4+/4+ | 4+/4+ | 4+/4+ | 4/4 | $>10^8$ |
| 1000 | 0/0 | 0/0 | 0/0 | 0/0 | 0/0 | $<10^3$ |
| 300 | 0/0 | 0/0 | 0/0 | 0/0 | 0/0 | $<10^3$ |
| 100 | 0/0 | 0/± | 0/0 | 0/0 | 0/0 | $<10^3$ |
| 30 | 0/± | 0/0 | 0/0 | 0/0 | 0/0 | $<10^3$ |
| 10 | 1/1 | 0/1 | 0/1 | 0/3 | 0/1 | $10^7$ |
| 3 | 2/2 | 2/3 | 2/2 | 3/3 | 1/3 | $>10^7$ |
| 1 | 3/3 | 3/3 | 2/3 | 2/2 | 2/2 | $>10^7$ |

LEGEND:
1 = LESS THAN 10 POSITIVE CELLS PER SLIDE
2 = GREATER THAN 10 CELLS, OR SMALL CLUSTERS OF + CELLS.
3 = LARGE FOCI OF FLUORESCENT CELLS, EVIDENT CPE.
4 = WIDESPREAD FLUORESCENCE, MANY FOCI.

EXPERIMENT Ia(k)

M413 Cells, CMV, Immunofluorescence Assay

The procedure described for Experiment Ia(j) was followed with cytomegalovirus (CMV) substituted for MAB to HSV-1.

TABLE Ia(k)

| Concentration | Log Virus Dilution | | | | |
|---|---|---|---|---|---|
|  | −1 | −2 | −3 | −4 | −5 |
| Controls (no IPA): |  |  |  |  |  |
| MAB-VCA | 4 | 3.5 | 3 | 2.5 | 2 |
| Normal Mouse IgG | 0 | 0 | 0 | 0 | 0 |
| Uninfected MAB-VCA | 0 |  |  |  |  |
| 1000 μM | 0.5 | 0.5 | 0.25 | 0 | 0 |
| 300 μM | 2 | 1.5 | 1 | 0.5 | 0.25 |
| 100 μM | 2 | 1.5 | 1 | 0.5 | 0.5 |
| 30 μM | 2 | 2 | 1.5 | 1 | 1 |
| 10 μM | 3 | 3 | 3 | 2 | 2 |
| 3 μM | 3.5 | 3 | 3 | 2 | 2 |
| 1 μM | 4 | 3.5 | 3 | 2.5 | 2 |

EXPERIMENT Ia(l)

Test of IPA on HIV-1 infected 81-66-45 cells

The 81-66-45 cell line is an HTLV-1 transformed non-producer. The procedure of Experiment 1a(a) was followed. The results are summarized in Table Ia(1).

TABLE Ia(l)

| Drug | | Titer | Percent Inhibition |
|---|---|---|---|
| None | | $1 \times 10^4$ | |
| AZT | 100 μM | <10 | >99.9 |
| AZT | 30 μM | <10 | >99.9 |
| ddC | 100 μM | <10 | >99.9 |
| ddC | 30 μM | <10 | >99.9 |
| IPA | 1000 μM | <10 | >99.9 |
| IPA | 300 μM | <10 | >99.9 |
| IPA | 100 μM | <10 | >99.9 |
| IPA | 30 μM | <10 | >99.9 |
| IPA | 10 μM | $1 \times 10$ | 90 |
| IPA | 3 μM | $1 \times 10$ | 0 |
| IPA | 1 μM | $1 \times 10$ | 0 |

EXPERIMENT Ia(m)

Stability Tests of IPA

Infrared spectra of IPA, taken from time to time, as described below, were used to monitor changes which may have occurred in the IPA over time. The compound was generally stored at $-10°$ C. FT-IR data of fresh IPA are listed in the first column of Table Ia(m). A second FT-IR spectrum of the same compound, after storage at $-10°$ C. for 110 days, was taken ad the data are listed in the second column of Tale Ia(m). The melting point of the compound was taken at the same time. The original melting point was 128-130° C., and the second melting point, 110 days later, was 129-132° C.

As can be seen from Table Ia(m), there was little change in the FT-IR spectrum of the compound and no significant change in the melting point of the compound. The observed melting points compare favorably with literature melting points ranging from 126° C. to 138° C.

*TABLE Ia(m)

| FT-IR Peak Wavelengths in μM for Samples of IPA | |
|---|---|
| Fresh IPA | After Storage for 110 days at $-10°$ C. |
| 1626 | 1626 |
| 1537 | 1537 |
| 1475 | 1475 |
| 1420 | 1419 |
| 1381 | 1381 |
| 1337 | 1338 |
| 1295 | 1294 |
| 1270 | 1270 |
| 1221 | 1221 |
| 1184 | 1184 |
| 1098 | 1099 |
| 1079 | 1079 |
| 1057 | 1057 |
| 1031 | 1032 |
| 986 | 986 |
| 961 | 961 |
| 865 | 866 |
| 823 | 824 |
| 794 | 793 |
| 763 | 763 |
| 713 | 714 |
| 668 | 668 |
| 641 | 639 |
| 555 | 555 |
| 434 | 434 |

ADDITIONAL IN-VITRO TESTS ON IPA.

The effect of the drug IPA on HIV-1 replication was examined in vitro in acutely and persistently infected cells. Production of HIV-1 in culture supernatant was determined by the presence of HIV P24. Methods In vitro infection of H9 cells was carried out as described previously. Briefly, $5 \times 10^6$ H9 cells were treated with DEAE-dextran (25 μg/ml) for 20 min. Cells were then infected with 1 ml of cell free HIV-1 ($1 \times 10^5$ RT unit) for 1 hr at 37° C. Cells were then washed and incubated for 12 days in the absence or presence of various concentrations of IPA. Every 3-4 days, the medium was replaced with fresh medium containing appropriate concentrations of drug. At various days following infection, the presence of HIV-1 in the supernatant was monitored by measuring HIV-1 P24 using the antigen capture test (DuPont ®, Wilmington, DE).

HIV-1 production from an AIDS patients' lymphocytes was carried out as described previously. Briefly, $10 \times 10^6$ patients' lymphocytes were cocultured with $5 \times 10^6$ PHA-stimulated normal PBL in RPMI 1640 medium containing 20% FBS, 5% interleukin 2 (Cellular Products, Buffalo, NY) and various concentrations of IPA. The culture was continued for 4 weeks. The culture was fed twice a week with $2-3 \times 10^6$ PHA-stimulated normal PBL. Culture medium was withdrawn twice a week and tested for the presence of HIV by the antigen capture test. Culture medium was replaced with new medium with or without drug at 3-4 days intervals.

To examine the effect of IPA on the production of HIV-1 in H9 cells persistently infected with HIV-1, $5 \times 10^6$ HIV-1-infected H9 cells were incubated in the absence or presence of IPA. Every 4-5 days, two thirds of the total cells were removed and medium was changed. New medium with or without drug was added to bring up to the original volume. At days indicated, culture supernatant was withdrawn and tested for the production of HIV-1 by the RT activity. A 20,000 cpm or more TCA insoluble radioactivity per milliliter of supernatant was considered positive in the RT assay.

Results

Figure 13:
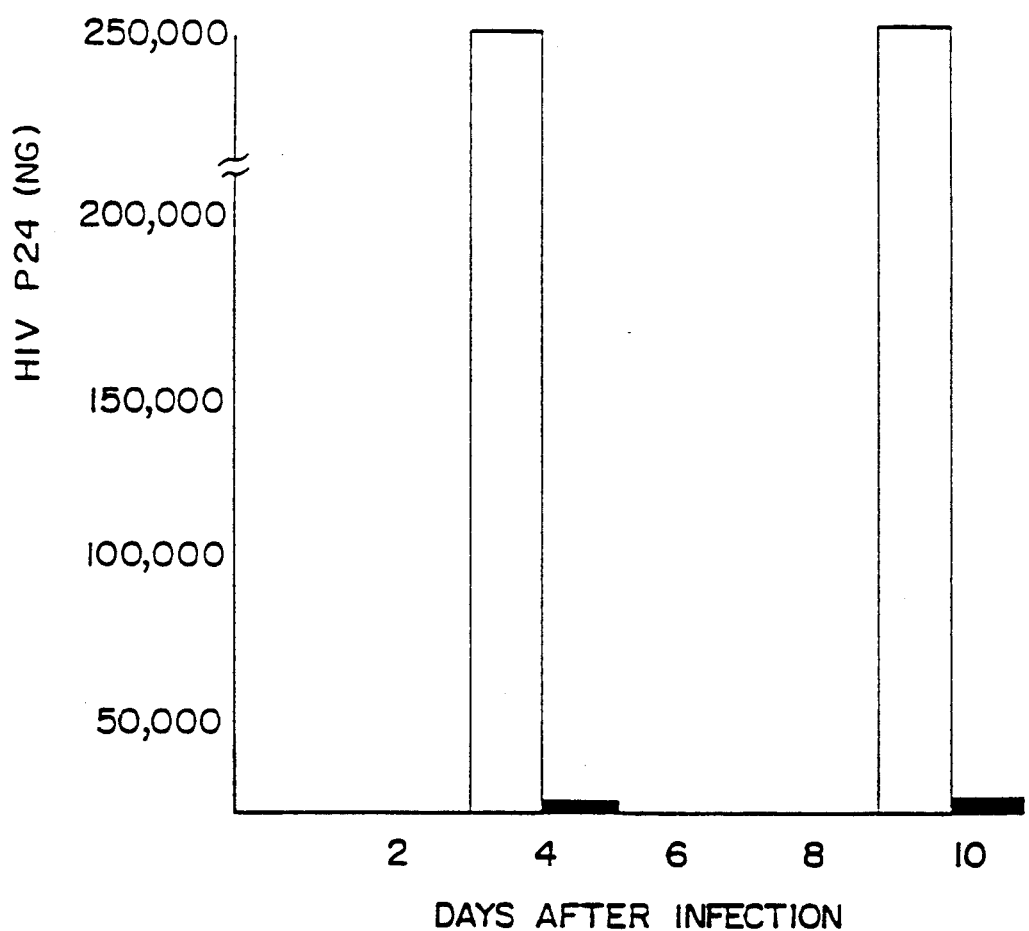
FIG. 13 is a graph of effects of IPA on in-vitro HIV infection of H9 cells.

An investigation of the effect of IPA on invitro HIV-1 infection of H9 cells, a T cell line, was performed. The drug was added following 1 hr adsorption of the virus, and was maintained in the culture medium throughout the incubation period. As shown in FIG. 13, IPA inhibited in vitro HIV-1 infection in a dose dependent manner. A more than five log inhibition of HIV-1 production was obtained at doses of 3.75 μM or higher.

IPA at concentrations of 30 μM or lower did not have any significant cytotoxic effect on the growth of viable PHA stimulated PBL up to 10 days in culture (Table G1).

Figure 14:
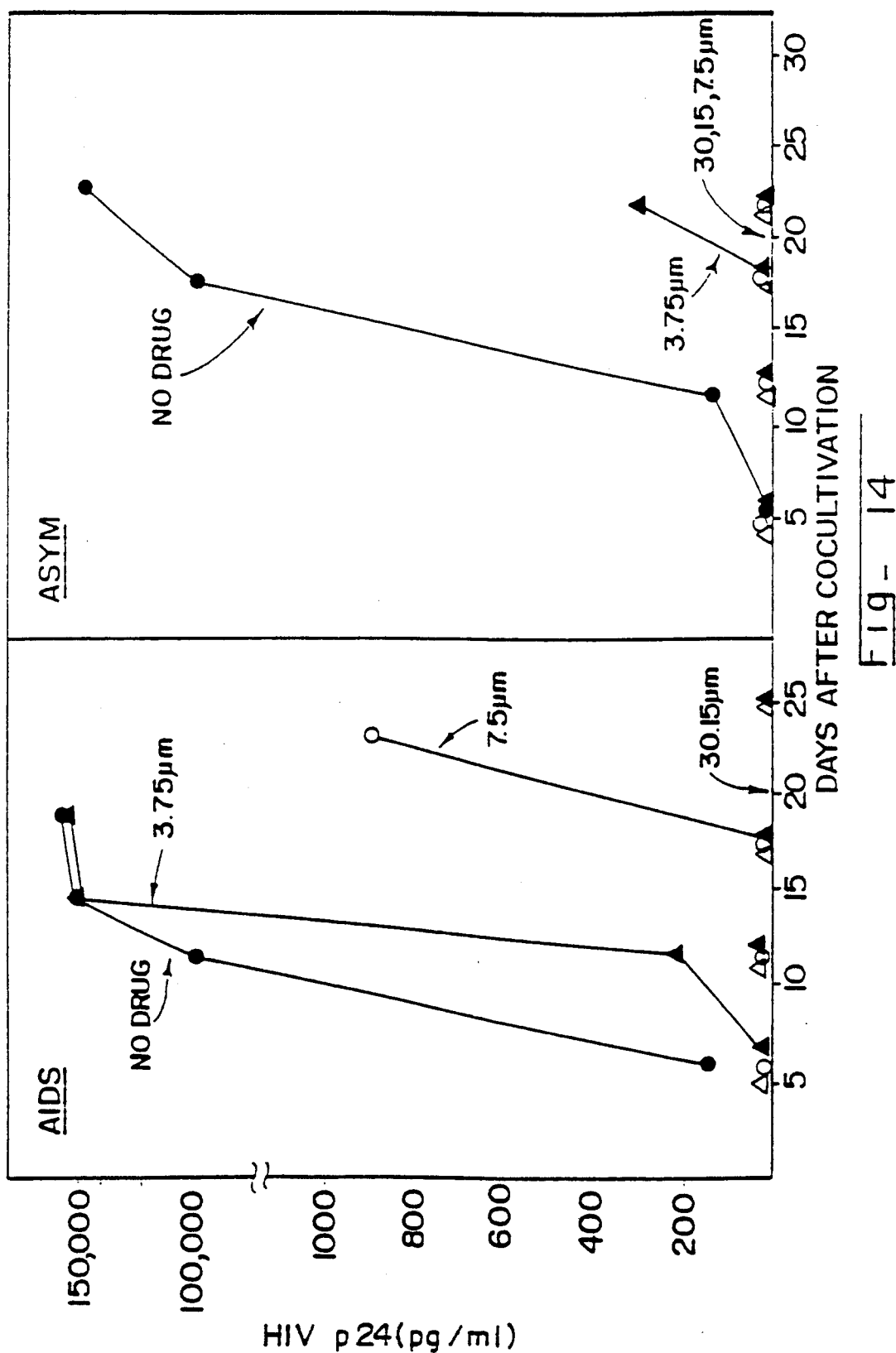
FIG. 14 is a graph of effects of IPA on HIV production.

A study of IPA inhibition of HIV-1 production from lymphocytes of a HIV-1 seropositive patient was carried out. For this purpose, lymphocytes from an AIDS patient and an asymtomatic patient were cocultured with PHA stimulated PBL in the presence or absence of IPA. Results shown in FIG. 14 indicate that IPA inhibited HIV-1 production in a dose dependent manner. Virus production, as determined by the HIV-1 p24 antigen capture assay, was completely blocked by IPA at concentrations of 3.75 μM or higher. In contrast, HIV-1 was detected in untreated cultures as early as 7 days following cocultivation.

The effect of IPA on replication of HIV-1 was also examined in H9 cells that were persistently infected with HIV-1 (H9-HIV-1). No cytotoxicity was observed up to 30 days in H9-HIV-1 cells incubated with IPA at concentrations of 30 μM and lower, as judged by the measurement of viable cell number.

These results demonstrate IPA to be an active anti HIV-1 agent, capable of suppressing in vitro infection by extracellular virus as well as HIV-1 production from lymphocytes of seropositive men. It has recently been shown that during cocultivation of lymphocytes from HIV-1-infected patients with normal mitogen stimulated PBL, spread of HIV-1 from infected cells to uninfected cells occurs by cell-to-cell transmission, as well as by infection through extracellular virus. AZT inhibits HIV-1 infection by extracellular virus, but has no effect on virus growth following cell-to-cell transmission of HIV-1. The fact that IPA inhibits HIV-1 production from infected patient' lymphocytes indicates that the drug not only inhibits infection by extracellular virus but also blocks virus production resulting from cell-to-cell transmission of HIV-1.

TABLE G1
EFFECT OF IPA ON THE GROWTH OF PBL AND H9 CELLS

| IPA Conc. (μM) | Following in-vitro* Following in-vitro infection of H9 | Following coculti-** vation of patients PBL with PHA-PBL |
| --- | --- | --- |
| 0 | $3.4 \times 10^6$ | $2.9 \times 10^6$ |
| 3.75 | $3.4 \times 10^6$ | $2.9 \times 10^6$ |
| 7.5 | $3.5 \times 10^6$ | $2.8 \times 10^6$ |
| 15 | $3.3 \times 10^6$ | $2.8 \times 10^6$ |
| 30 | $2.7 \times 10^6$ | $2.7 \times 10^6$ |

*Number of viable cells were measured by trypan blue exclusion method, following in-vitro infection of H9 cells from FIG. 13. Number of cells recovered after 10 days.
**Number of cells recovered at 10 days following cocultivation of lymphocytes of an AIDS patient with PHA-stimulated normal PBL from FIG. 14.

TABLE G2
EFFECT OF IPA ON HIV PRODUCTION FROM H9 CELLS PERSISTENTLY INFECTED WITH HIV

| DRUG CONCENTRATION | HIV PRODUCTION RT ACTIVITY cpm/ml | |
| --- | --- | --- |
| | 15 DAYS p.d. | 25 DAYS p.d. |
| 0 | $3 \times 10^5$ | $1.1 \times 10^6$ |
| 3.75 | $2.3 \times 10^5$ | $1.2 \times 10^5$ |
| 7.5 | $2.9 \times 10^5$ | $3.2 \times 10^5$ |
| 15 | $2.3 \times 10^5$ | $3.6 \times 10^5$ |
| 30 | $2.9 \times 10^5$ | $2.5 \times 10^5$ | p.d. = POST DRUG TREATMENT

SUMMARY OF RESULTS AND DATA MANIPULATION

Figure 15:
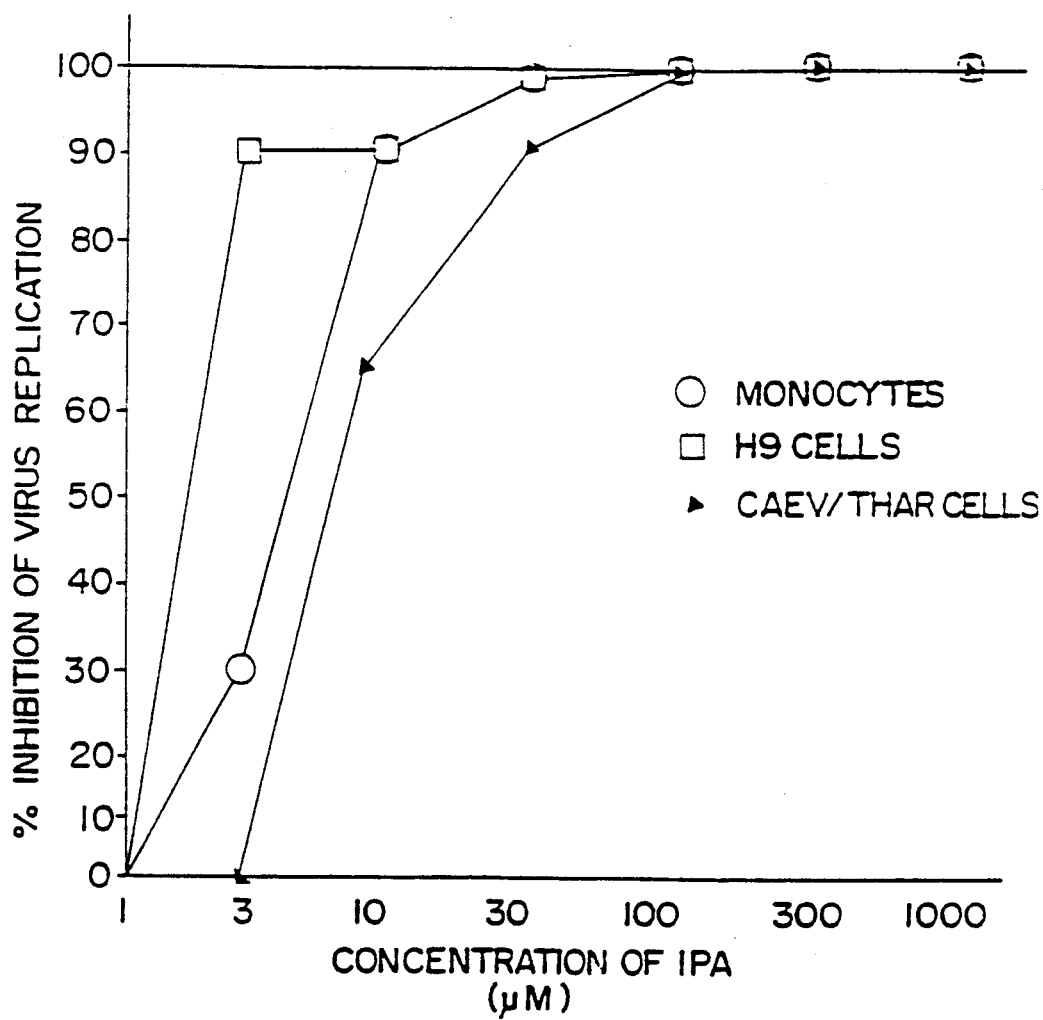
FIG. 15 is a graph of inhibition of virus replication versus concentration of IPA in an assay.

Selected results presented in Tables Ia(a), Ia(b) and Ia(c) are plotted in FIG. 15. These results do not take into account any possible toxic effects of IPA. Reading from FIG. 1, $IC_{50}$ and $IC_{90}$ values can be determined and are listed in Table A.

TABLE A

| Cell Line | $IC_{50}$ and $IC_{90}$ Values for IPA as read from FIG. 15 | | |
| --- | --- | --- | --- |
| | Virus | $IC_{50}$ | $IC_{90}$ |
| Monocytes | HIV-1 | 6 μM | 10 μM |
| H9 | HIV-1 | 2 μM | 3 μM |
| Himalayan | | | |

TABLE A-continued

| Cell Line | $IC_{50}$ and $IC_{90}$ Values for IPA as read from FIG. 15 | | |
| --- | --- | --- | --- |
| | Virus | $IC_{50}$ | $IC_{90}$ |
| Tahr Ovary | CAEV | 8 μM | 30 μM |

It is apparent from FIG. 15 that IPA appear as to inhibit the replication of HIV-1 and CAEV at concentrations ranging from 3 to 30 μM and above. Without appropriate toxicity data it is not possible to calculate the therapeutic index at the various drug concentrations. Nevertheless, the $IC_{50}$ can be seen to vary between approximately 2-6 μM, depending upon the virus and cell line, and the $IC_{90}$ varies between 3-30 μM in these experiments.

Results from Experiment Ia(b) (Table Ia(b) (ii)) and Experiment Ia(I) (Table Ia(i)) are summarised in Summary Table 1.

The "Percent Dead Cells" are taken from Tables Ia(d) (iii) and Ia(d) (v) using the 10-day value, and the therapeutic index have been calculated for each drug concentration. The results of IPA are also graphed in FIGS. 16 and 17. Cytotoxicity (the dashed line) is calculated as the percent live cells.

Figure 16:
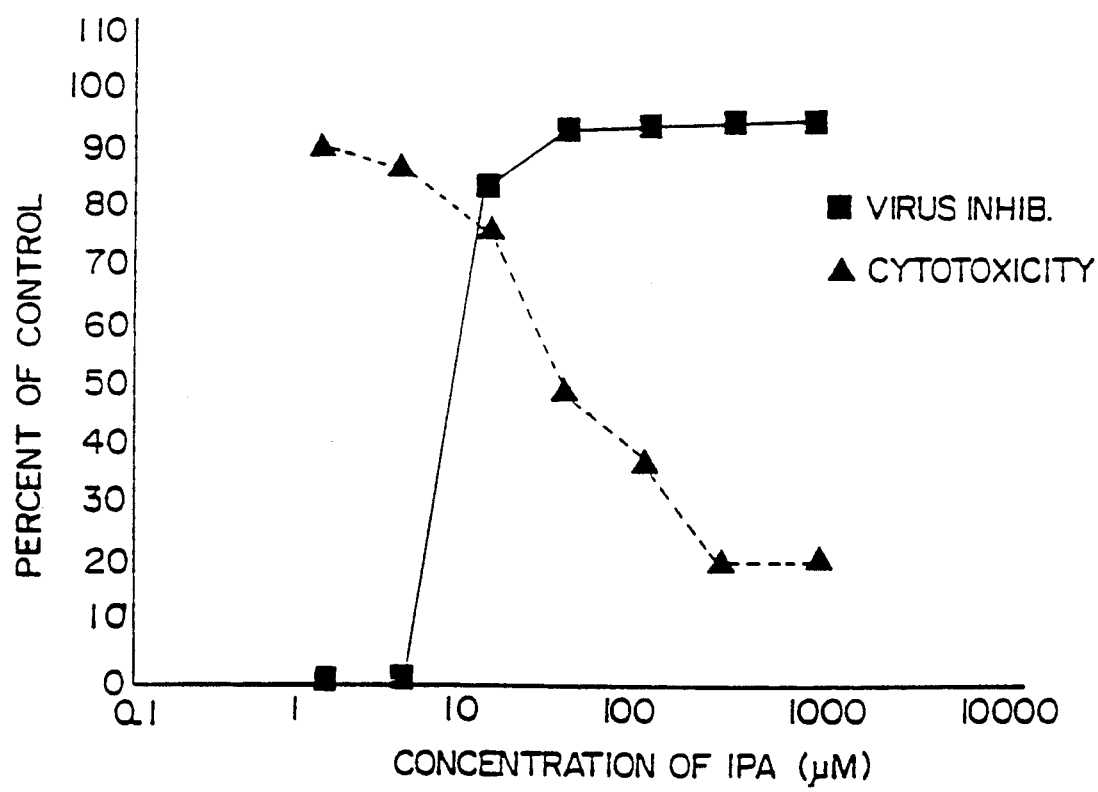
FIGS. 16 and 17 are graphs of cYtotoxicitY and virus inhibition versus concentration of IPA in an assaY.
Figure 17:
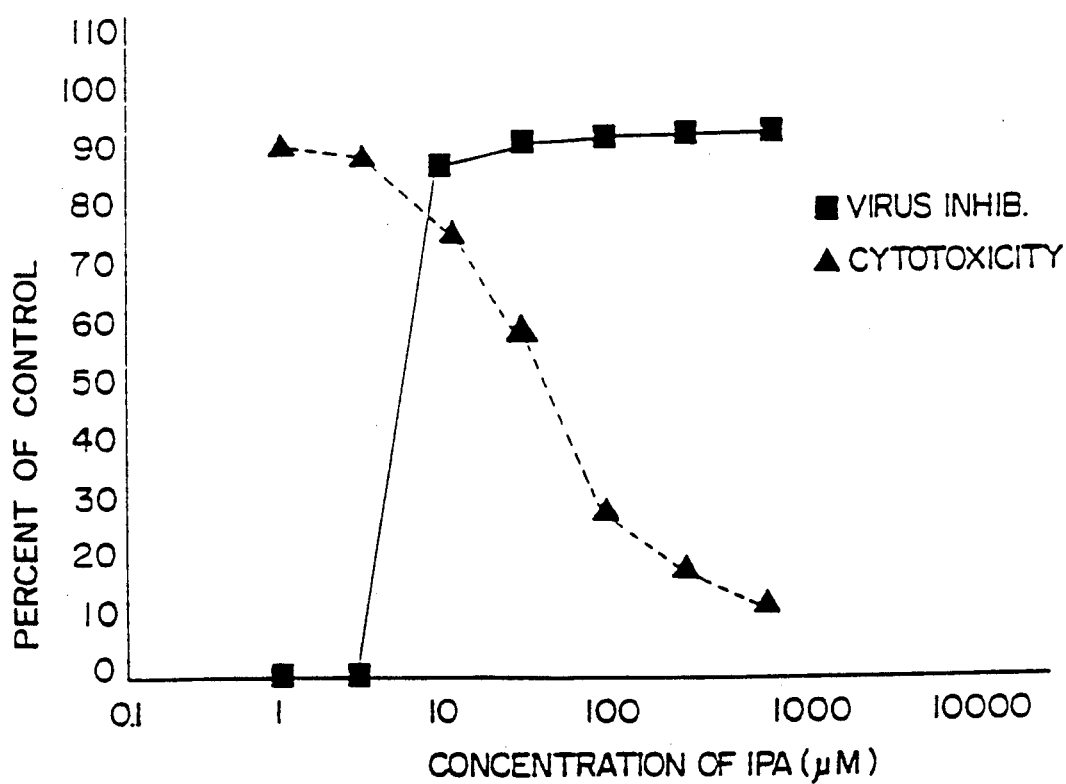
Figure 18:
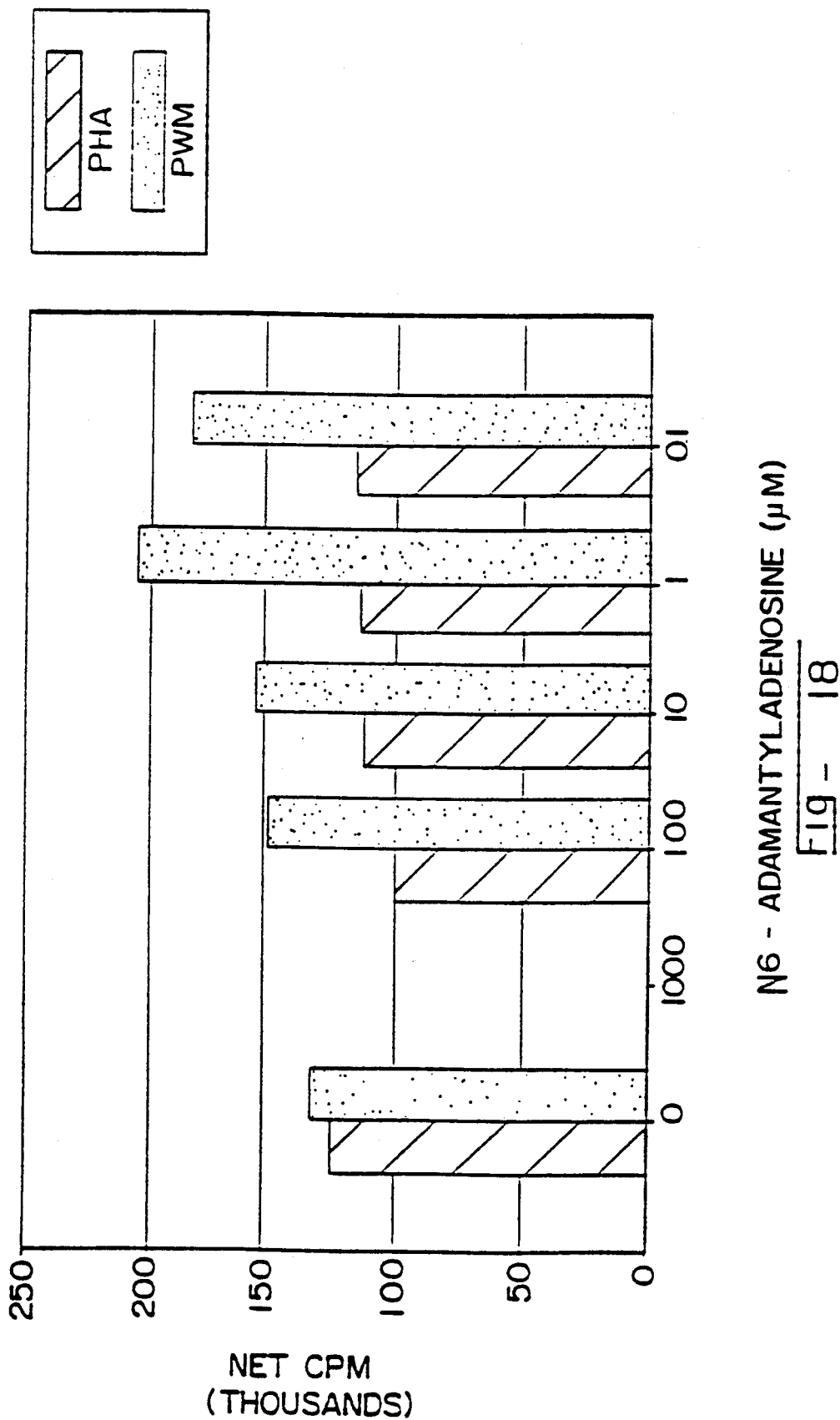
FIG. 18 is a graph of human T and B lymphocyte function versus concentration of $N^6$-adamantyladenosine in an assay.
Figure 19:
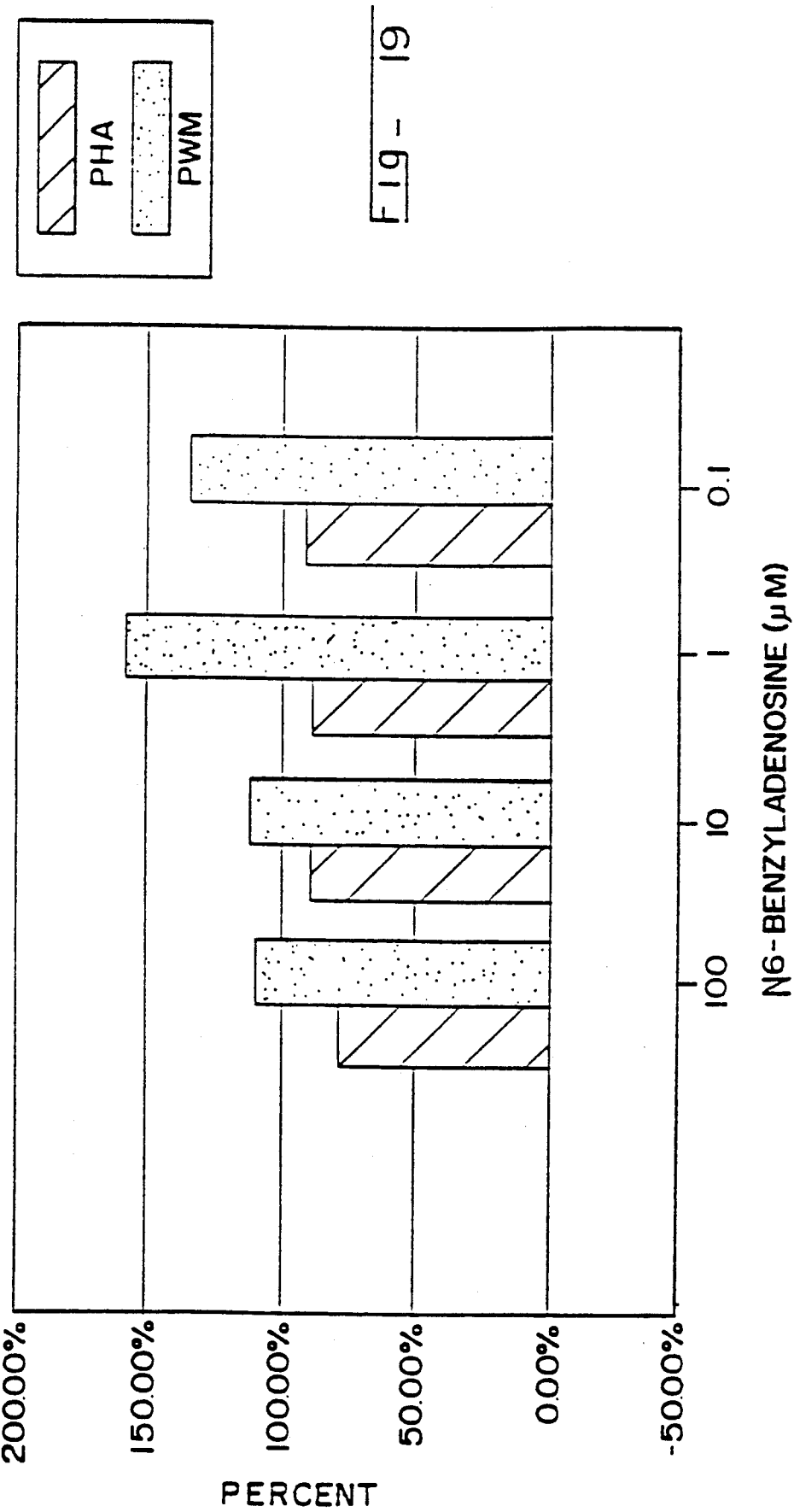
FIG. 19 is a graph of human T and B lymphocyte function versus concentration of $N^6$-benzyladenosine in an assay.
Figure 20:
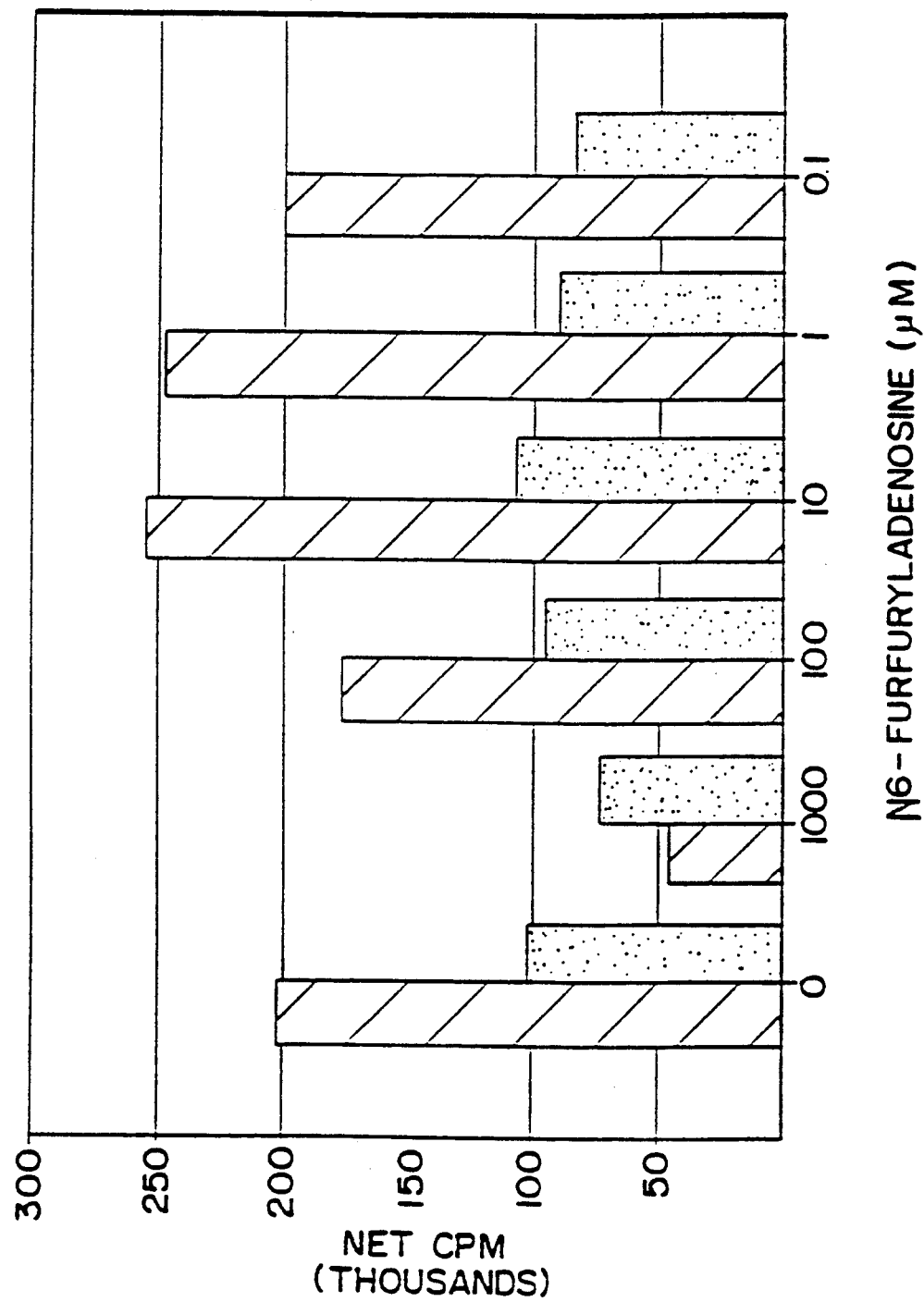
FIG. 20 is a graph of human T and B lymphocyte function versus concentration of $N^6$-furfuryladenosine in an assay.
Figure 21:
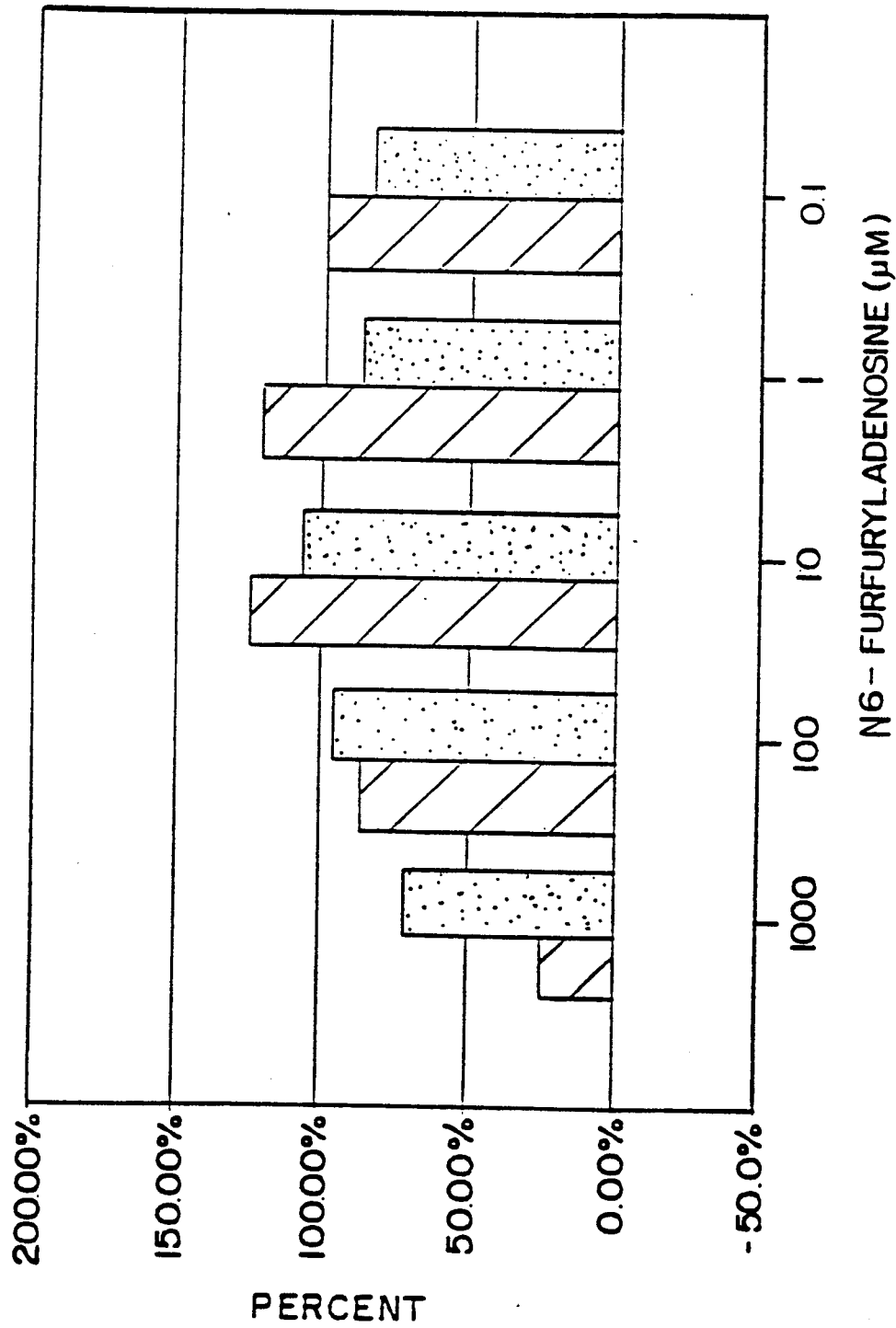
FIG. 21 is a graph of human T and B lymphocyte function versus concentration of $N^6$-furfuryladenosine in an assay.
Figure 22:
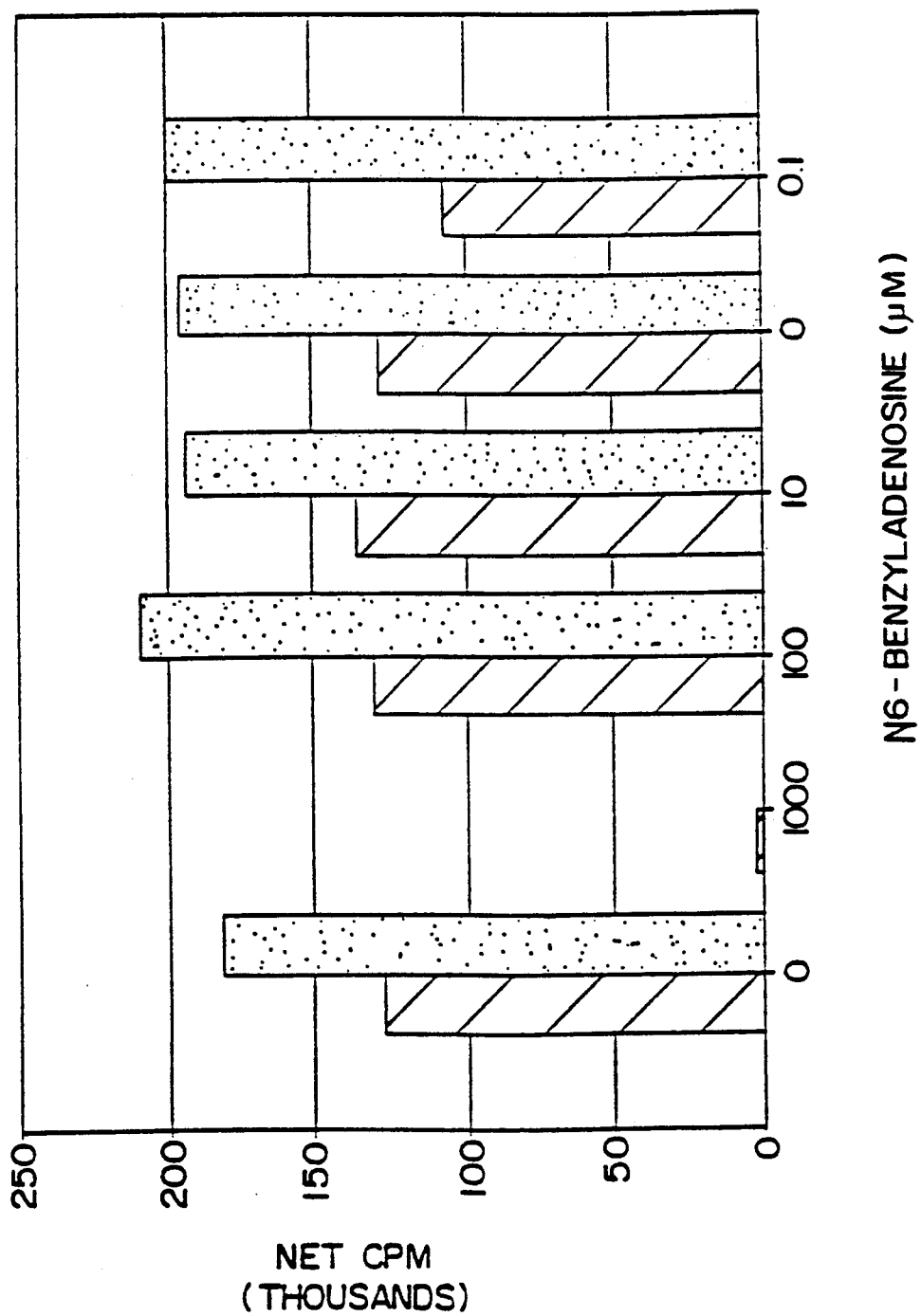
FIG. 22 is a graph of human T and B lymphocyte function versus concentration of $N^6$-benzyladenosine in an assay.
Figure 23:
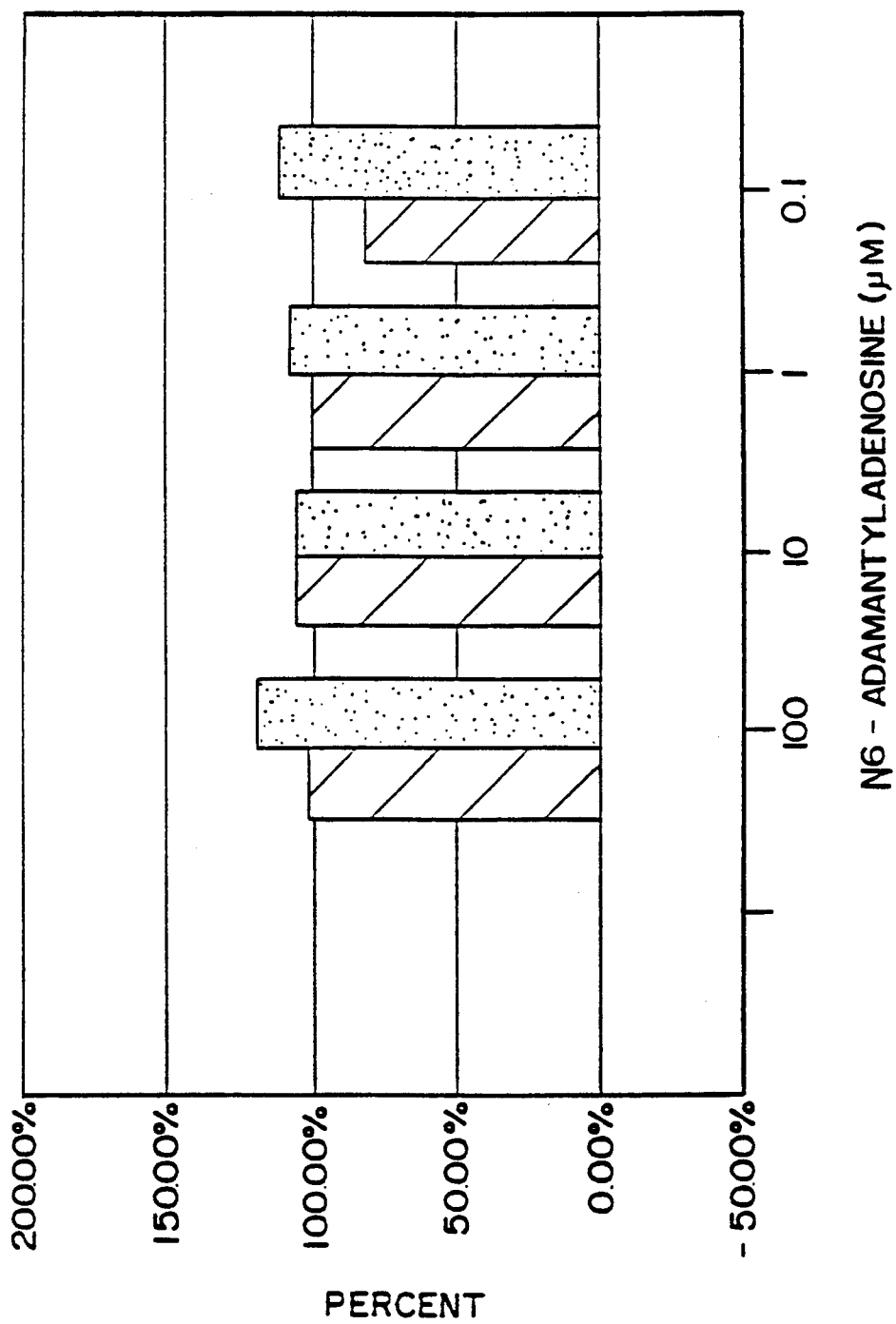
FIG. 23 is a graph of human T and B lymphocyte function versus concentration of $N^6$-adamantyladenosine in an assay.

The availability of toxicity data collected in the same time frame as required for determination of antiviral effectiveness allowed determination of values for two different cell lines. FIGS. 16 and 17 illustrate the curves obtained by plotting the cytotoxicity of IPA (as a percent of the control cell viability) versus the percent of inhibition of HIV-1 replication (as a percent of the control titer) when H9 and 81-66-45 cells were tested. The cytotoxicity data obtained with 10 days continuous exposure, using uninfected cells, were used since 10 days was the length of time required to carry out the infectivity test. As is apparent from Tables Ia(d) (ii)-Ia(d) (v), toxicity is much lower when the drug is added to cells for one day and then removed, or when cells are exposed for only 1 or 4 days. It is difficult to mimic in-vivo exposure times, particularly if metabolites are more toxic than the parent compound and are readily cleared in-vivo but not in-vitro.

Analysis of FIGS. 16 and 17 permit a list of the inhibition values for the two cell lines to be calculated as follows:

| | H9 Cells | 81-66-45 Cells |
| --- | --- | --- |
| $IC_{50}$* | 6 μM | 6 μM |
| $IC_{90}$** | 10 μM | 10 μM |
| $ID_{50}$*** | 50 μM | 40 μM |
| $IC_{50}/ID_{50}$ | 0.12 | 0.20 |

*$IC_{50}$ - The concentration of IPA which inhibits the replication of HIV-1 by 50%.
**$IC_{90}$ - The concentration of IPA which inhibits the replication of HIV-1 by 90%.
***$ID_{50}$ - The concentration of IPA which kills 50% of the cells.

EXPERIMENTS INVOLVING COMPOUNDS Id, Ig, Ih, AND Ii

About 100 ml of solution containing bout $5 \times 10^7$ 81-66-45 cells were pelleted by centrifugation, resuspended in 35 ml and divided into 5 ml aliquots. Six of the seven 5 ml aliquots were centrifuged again and the pellets which formed were each suspended in 5 ml of HIV-1, serially diluted in 10fold steps starting with undiluted virus. Serial dilutions of he virus were made using complete medium containing 10 g/ml of polybrene. The cells were then incubated at 37° C. for 1.5 hour, with occasional shaking. The aliquots were centrifuged again and the pellets which formed were each suspended 35 ml of fresh medium, RPMI 1640 and 10% FBS. These stock dilutions were then used with each of the compounds being tested, being distributed onto a 24 well tray with 0.25 ml per well.

To each well was added 0.25 ml of drug solution prepared as described below at concentration. In the preparation of stock drug solutions, water soluble compounds were dissolved to make solutions of 10 $\mu$M. If necessary, ethanol dimethyl sulfoxide (DMSO) were used to dissolve a compound. Stock drug solutions were serially diluted in 10 fold concentration steps as indicated in the Tables below. A two fold dilution of the drug takes place on addition of 0.25 ml of each solution to each well, which already contains 0.25 ml of virus solution.

The seventh aliquot of cell suspension, uninfected by virus was used to determine drug effects on uninfected cells. To each well in a row of wells, each well containing 0.25 ml of cell suspension, was added 0.25 ml of drug solution, serially diluted.

The titer of HIV-1 at each level was determined using radio immunofluorescence (RIA) after 10 days and the viability of uninfected cells in the presence of each drug was determined.

Results of the above experiments are tabulated in Tables Id(i), Ig(i), Ih(i) and Il(i) below.

TABLE Id(i)

Benzyladenosine

| CONCENTRATION $\mu$M | TITER | PERCENT INHIBITION | VIABILITY |
|---|---|---|---|
| 1000 | $10^3$ | 90-99 | 80 |
| 100 | $10^4$ | 0-90 | 89 |
| 10 | $10^4$ | 0-90 | — |
| 1 | $10^4$ | 0-90 | — |
| 0.1 | $10^5$ | 0 | — |

TABLE Iq(i)

Furfuryladenosine

| CONCENTRATION $\mu$M | TITER | PERCENT INHIBITION | VIABILITY |
|---|---|---|---|
| 100 | <10 | — | 0 |
| 10 | $10^3$ | 90-99 | 71 |
| 1 | $10^4$ | 0-90 | 71 |
| 0.1 | $10^3$ | 90-99 | 88 |

TABLE Ih(i)

$N^6$-Furfuryladenosine-5'-Monophosphate

| CONCENTRATION $\mu$M | TITER | PERCENT INHIBITION | VIABILITY |
|---|---|---|---|
| 1000 | 10 | 90-99 | <50 |
| 100 | $10^3$ | 0-90 | 90 |
| 10 | $10^4$ | 0-90 | — |
| 1 | $10^4$ | 0-90 | — |
| 0.1 | $10^4$ | 0-90 | — |

TABLE Il(i)

$N^6$-Adamantyladenosine

| CONCENTRATION $\mu$M | TITER | PERCENT INHIBITION | VIABILITY |
|---|---|---|---|
| 1000 | <10 | 99.9-99.99 | 87 |
| 100 | $10^4$ | 0-90 | — |
| 10 | $10^4$ | 0-90 | — |
| 1 | $10^4$ | 0-90 | — |
| 0.1 | $10^4$ | 0-90 | — |

A series of experiments, following the procedure outlined in Experiment 1a(I), were carried out to study the effects of compounds Id, Ig and Il analogues and metabolites on human T and B lymphocyte function. The results are presented in Charts Id(i), Id(ii), Ig(i), Ig(ii), Il(i), Il(ii) (FIGS. 18–23).

Although the present invention has been described in connection with preferred embodiments, it will be appreciated by those skilled in the art that additions, modifications, substitutions and deletions not specifically described may be made without departing from the spirit and scope of the invention defined in the appended claims.

I claim:

1. A method of treating a human or animal suffering from a haemoflagellate parasitic infection comprising administering to a human or animal who has been infected with a haemoflagellate parasite an effective amount of a pharmaceutical formulation comprising a compound, or a physiologically acceptable salt thereof, selected from the group having the formula:

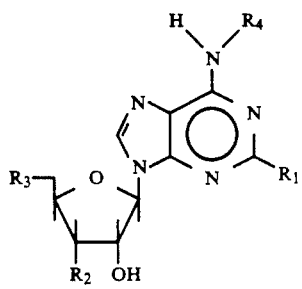

wherein:
$R_1$=H, $R_2$=$CH_3$, $R_3$=$CH_3$ and $R_4$=H, or
$R_1$=H or $CH_3S$ and

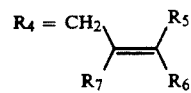

and
$R_5$=$CH_3$, Cl, OH or a monophosphate group
$R_5$=$CH_3$, $CH_2OH$ or Cl
$R_7$=H or Br
or $R_1$=H and

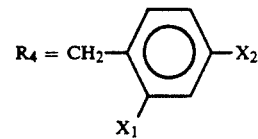

and $X_1$ and $X_2$ are independently selected from H, methyl, ethyl, hydroxyl, the halogens and carboxyl

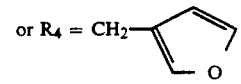

-continued or $R_4 = $ 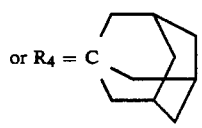

or $R_4 = \overset{O}{\underset{\|}{C}}NH-R_8$ and $R_8 = C$ 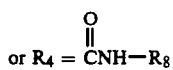

or $R_8=(CH_2)_7CH_3$;
and $R_2=OH$ and $R_3=OH$, monophosphate, diphosphate or triphosphate group
or $R_2$ and $R_3$ are linked to form a 3', 5'-(cyclic monophosphate derivative,
or a metabolite of said compound, said metabolite being a member of the group consisting of:
$N^6$-($\Delta^2$-isopentenyl) adenine;
6-N-(3-methyl-3-hydroxybutylamino) purine;
Adenine;
Hypoxanthine;
Uric Acid; and
Methylated xanthines.

2. The method of recited in claim 1, wherein said at least one compound is Poly N6 Isopentenyl Adenosine.

3. The method recited in claim 1, wherein said parasite has a mode of survival similar to that of Toxoplasma.

4. The method recited in claim 1, wherein said compound is effective to kill said haemoflagellate parasite in macrophages.

5. The method recited in claim 1, wherein said compound is effective to prevent replication of said haemoflagellate parasite in macrophages.

6. The method recited in claim 1, wherein said compound is effective in cause intracellular digestion of said haemoflagellate parasite in macrophages.

7. A method of treating a human or animal suffering from a haemoflagellate parasitic infection comprising administering to a human or animal who has hd an abnormal level of a haemoflagellate parasite an effective amount of a pharmaceutical formulation comprising a compound, or a physiologically acceptable salt thereof, selected from the group having the formula:

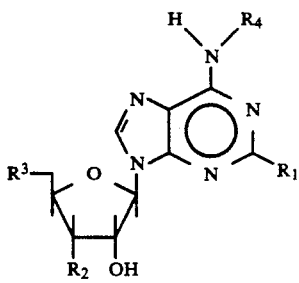

wherein:
$R_1=H$, $R_2=CH_3$, $R_3=CH_3$ and $R_4=H$, or
$R_1=H$ or $CH_3S$ and $R_4 = $ 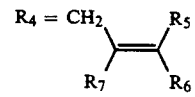

and
$R_5=CH_3$, Cl, OH or a monophosphate group
$R_6=CH_3$, $CH_2OH$ or Cl
$R_7=H$ or Br
or $R_1=H$ and $R_4 = CH_2-$ 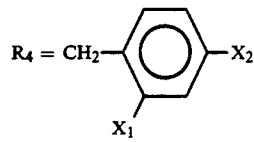

and $X_1$ and $X_2$ are independently selected from H, methyl, ethyl, hydroxyl, the halogens and carboxyl or $R_4 = CH_2-$ 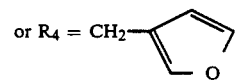

or $R_4 = C$ 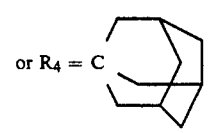

or $R_4 = \overset{O}{\underset{\|}{C}}HN-R_8$ and $R_8 = C$ 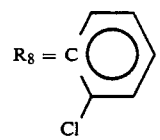

or $R_8=(CH_2)_7CH_3$
and $R_2=OH$ and $R_3=OH$, monophosphate, diphosphate or triphosphate group
or $R_2$ and $R_3$ are linked to form a 3', 5'-cyclic monophosphate derivative,
or a metabolite of said compound, said metabolite being a member of the group consisting of:
$N^6$-($\Delta^2$-isopentenyl) adenine;
6-N-(3-methyl-3-hydroxybutylamino) purine;
Adenine;
Hypoxanthine;
Uric Acid; and
Methylated xanthines.

8. The method recited in claim 7, wherein said one or more kind of parasite is one or more kind of microsporidiosis.

9. A method of treating a human or animal suffering from a Mycoplasma infection comprising administering to a human or animal who has been infected with Mycoplasma an effective amount of a pharmaceutical formulation comprising a compound, or a physiologically acceptable salt thereof, selected from the group having the formula:

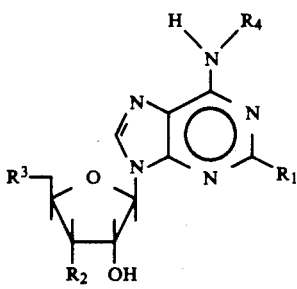

wherein:
$R_1$=H, $R_2$ CH$_3$, $R_3$=CH$_3$ and $R_4$=H, or
$R_1$=H or CH$_3$S and

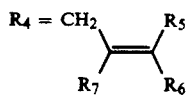

and
$R_5$=CH$_3$, Cl, OH or a monophosphate group
$R_6$=CH$_3$, CH$_2$OH or Cl
$R_7$=H or Br
or $R_1$=H and

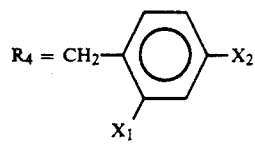

and $X_1$ and $X_2$ are independently selected from H, methyl, ethyl, hydroxyl, the halogens and carboxyl

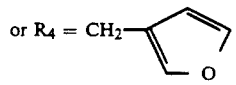

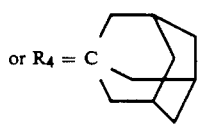

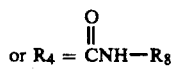

and

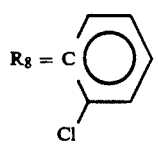

or $R_8$=(CH$_2$)$_7$CH$_3$;
and $R_2$=OH and $R_3$=OH, monophosphate, diphosphate or triphosphate group
or $R_2$ and $R_3$ are linked to form a 3', 5'-cyclic monophosphate derivative or a metabolite of said compound, said metabolite being a member of he group consisting of:
N$^6$-($\Delta^2$-isopentenyl) adenine;
6-N-(3-methyl-3-hydroxybutylamino) purine;
Adenine;
Hypoxanthine;
Uric Acid; and
Methylated xanthines.

10. The method recited in claim 10, wherein said Mycoplasma is selected from the group consisting of Mycoplasma athritidis, Mycoplasma fermentans and Mycoplasma incognitus.

11. A method comprising administering to a blood sample containing parasite an effective amount of a pharmaceutical formulation comprising a compound, or a physiologically acceptable salt thereof, selected from the group having the formula:

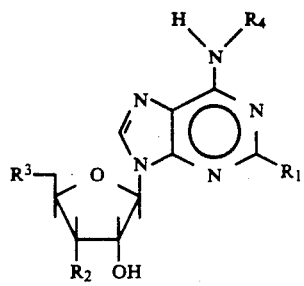

wherein:
$R_1$=H, $R_2$=CH$_3$, $R_3$=CH$_3$ and $R_4$=H, or
$R_1$=H or CH$_3$S and

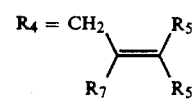

and
$R_5$=CH$_3$, Cl, OH or a monophosphate group
$R_6$=CH$_3$, CH$_2$OH or Cl
$R_7$=H or Br
or $R_1$=H and

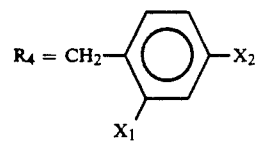

and $X_1$ and $X_2$ are independently selected from H, methyl, ethyl, hydroxyl, the halogens and carboxyl

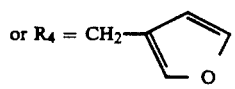

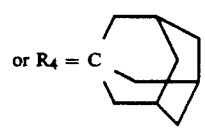

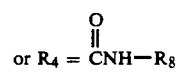

and

-continued $R_8 = $ 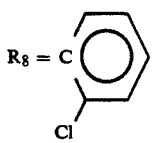

or $R_8=(CH_2)_7CH_3$;

and $R_2=OH$ and $R_3=OH$, monophosphate, diphosphate or triphosphate group or $R_2$ and $R_3$ are linked to form a 3', 5'-cyclic monophosphate derivative, or a metabolite of said compound, said metabolite being a member of the group consisting of:
$N^6$-($\Delta^2$-isopentenyl) adenine;
6-N-(3-methyl-3-hydroxybutylamino) purine;
Adenine;
Hypoxanthine;
Uric Acid; and
Methylated xanthines.

12. The method recited in claim 1, 7 or 11, wherein said parasite is selected from the group consisting of *Entercytozoon bieneusi, T. brucei, T. cruzi,* EPI, TRY, AM, T. b. brucei, T. b. gambiense, T. b. rhodesiense, leishmania, Trypanosomia and toxoplasma.

13. A method comprising administering to a blood sample containing mycoplasma an effective amount of a pharmaceutical formulation comprising a compound, or a physiologically acceptable salt thereof, selected from the group having the formula:

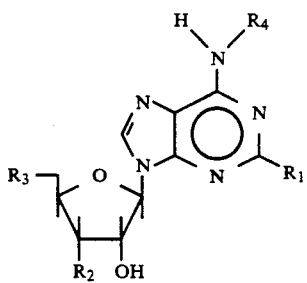

wherein:
$R_1=H$, $R_2=CH_3$, $R_3=CH_3$ and $R_4=H$, or
$R_1=H$ or $Ch_3S$ and

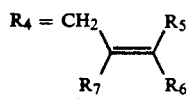

and
$R_5=Ch_3$, Cl, OH or a monophosphate group
$R_6=CH_3$, $CH_2OH$ or Cl
$R_7=H$ or Br
or $R_1=H$ and

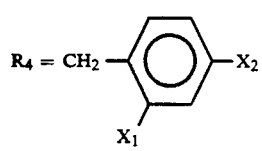

and $X_1$ and $X_2$ are independently selected from H, methyl, ethyl, hydroxyl, the halogens and carboxyl or $R_4 = CH_2-$ 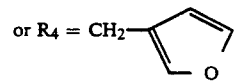

or $R_4 = C$ 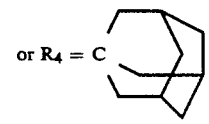

or $R_4 = \overset{O}{\underset{\|}{C}}NH-R_8$ 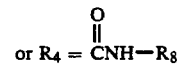

and $R_8 = C$ 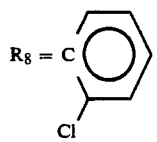

or $R_8=(CH_2)_7CH_3$;

and $R_2=OH$ and $R_3=OH$, monophosphate, diphosphate or triphosphate group or $R_2$ and $R_3$ are linked t form a 3', 5'-cyclic monophosphate derivative, or a metabolite of said compound, said metabolite being a member of the group consisting of:
$N^6$-($\Delta^2$-isopentenyl) adenine;
6-N-(3-methyl-3-hydroxybutylamino) purine;
Adenine;
Hypoxanthine;
Uric Acid; and
Methylated xanthines.

14. A method of treating a human or animal who has been exposed to the risk of haemoflagellate parasitic infection comprising administering to a human or animal who has been exposed to the risk of haemoflagellate parasitic infection an effective amount of a pharmaceutical formulation comprising a compound, or a physiologically acceptable salt thereof, selected from the group having the formula:

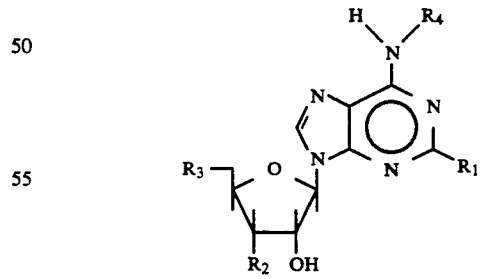

wherein:
$R_1=H$, $R_2=CH_3$, $R_3=CH_3$ and $R_4=H$, or
$R_1=H$ or $Ch_3S$ and

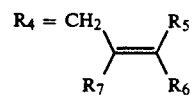

and
$R_5 = CH_3$, Cl, OH or a monophosphate group
$R_5 = CH_3$, $CH_2OH$ or Cl
$R_7 = H$ or Br
or $R_1 = H$ and

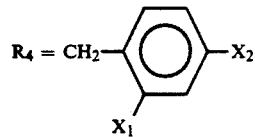

and $X_1$ and $X_2$ are independently selected from H, methyl, ethyl, hydroxyl, the halogens and carboxyl

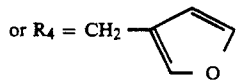

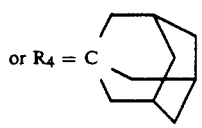

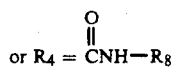

and

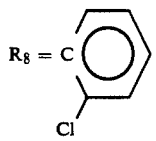

or $R_8 = (CH_2)_7CH_3$;
and $R_2 = OH$ and $R_3 = OH$, monophosphate, diphosphate or triphosphate group
or $R_2$ and $R_3$ are linked to form a 3', 5'-(cyclic monophosphate derivative,
or a metabolite of said compound, said metabolite being a member of the group consisting of:
$N^6$-($\Delta^2$-isopentenyl) adenine;
6-N-(3-methyl-3-hydroxybutylamino) purine;
Adenine;
Hypoxanthine;
Uric Acid; and
methylated xanthines.

15. A method of treating a human or animal who has been exposed to the risk of a Mycoplasma infection comprising administering to a human or animal who has been exposed to the risk of Mycoplasma infection an effective amount of a pharmaceutical formulation comprising a compound, or a physiologically acceptable salt thereof, selected from the group having the formula:

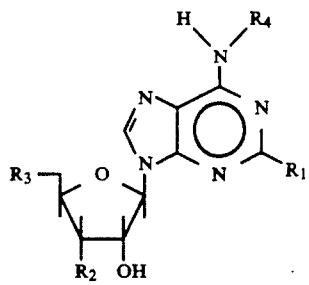

wherein:
$R_1 = H$, $R_2$ $CH_3$, $R_3 = CH_3$ and $R_4 = H$, or
$R_1 = H$ or $CH_3S$ and

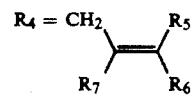

and
$R_5 = CH_3$, Cl, OH or a monophosphate group
$R_6 = CH_3$, $Ch_2OH$ or Cl
$R_7 = H$ or Br
or $R_1 = H$ and

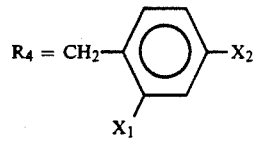

and $X_1$ and $X_2$ are independently selected from H, methyl, ethyl, hydroxyl, the halogens and carboxyl

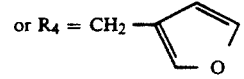

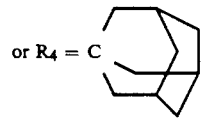

and

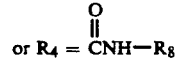

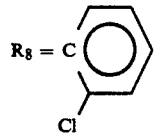

or $R_8 = (CH_2)_7CH_3$;
and $R_2 = OH$ and $R_3 = OH$, monophosphate, diphosphate or triphosphate group
or $R_2$ and $R_3$ are linked to form a 3', 5'-cyclic monophosphate derivative,
or a metabolite of said compound, said metabolite being a member of the group consisting of:
$N^6$-($\Delta^2$-isopentenyl) adenine;

6-N-(3-methyl-3-hydroxybutylamino) purine;
Adenine;
Hypoxanthine;
Uric Acid; and
Methylated xanthines.

16. The method recited in claim 1, 7, 11, 13, 14 or 15 wherein said compound has a combination of chemical groups $R_1$ to $R_4$ selected from the following combinations Ia to Iu:

Ia: $R_1 = H$, $R_2 = OH$, $R_3 = OH$ and

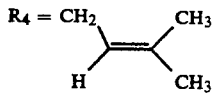

Ib: $R_1 = H$, $R_2 = OH$, $R_3 =$ monophosphate, and

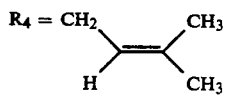

Ic: $R_1 = H$, $R_2$ and $R_3$ are linked to form a

3′, 5′-cyclic monophosphate derivative

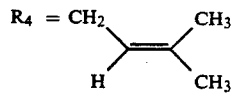

Id: $R_1 = H$, $R_2 = OH$, $R_3 = OH$, and $R_4 = CH_2C_6H_6$

Ie: $R_1 = H$, $R_2 = OH$ $R_3 =$ monophosphate, and $R_4 = CH_2C_6H_6$

If: $R_1 = H$, $R_2$ and $R_3$ are linked to form a

3′, 5′-cyclic monophosphate derivative and $R_4 = CH_2C_6H_6$

Ig: $R_1 = H$, $R_2 = OH$, $R_3 = OH$, $R_4 = $ 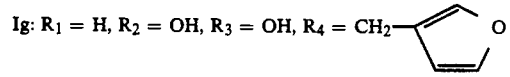

Ih: $R_1 = H$, $R_2 = OH$, $R_3 =$ monophosphate and

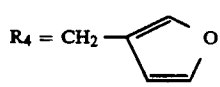

Ii: $R_1 = H$, $R_2$ and $R_3$ are linked to form a

3′, 5′-cyclic monophosphate derivative and

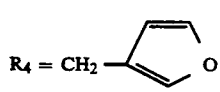

Ij: $R_1 = H$, $R_2 = OH$ and

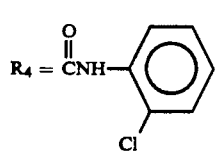

Ik: $R_1 = H$, $R_2 = OH$, $R_3 =$ monophosphate and

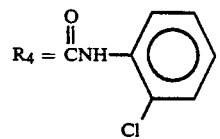

Il: $R_1 = H$, $R_2 = OH$, $R_3 = OH$ and

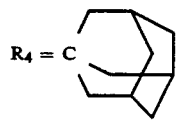

Im: $R_1 = H$, $R_2 = OH$, $R_3 =$ monophosphate and

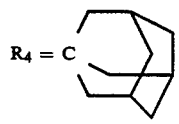

In: $R_1 = H$, $R_2 = OH$, $R_3 = OH$ and

Io: $R_1 = H$, $R_2 = OH$, $R_3 =$ monophosphate and

Ip: $R_1 = H$, $R_2$ and $R_3$ are linked to form a

3′, 5′-cyclic monophosphate derivative, and

Iq: $R_1 = CH_3S$, $R_2 = OH$, $R_3 = OH$ and

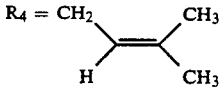

Ir: $R_1 = H$, $R_2 = OH$, $R_3 = OH$ and

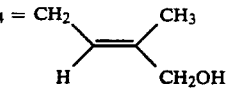

Is: $R_1 = H$, $R_2 = OH$, $R_3 = OH$ and

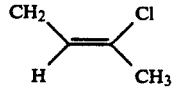

It: $R_1 = H$, $R_2 = OH$, $R_3 = OH$ and

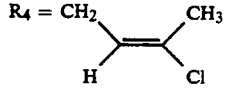

Iu: $R_1 = H$, $R_2 = CH_3$, $R_3 = CH_3$ and $R_4 = H$.

17. The method recited in claim 1, 7, 9, 11, 13, 14 or 15 wherein said compound has a combination of chemical groups R1 to R4 as follows:

Ia: $R_1 = H$, $R_2 = OH$, $R_3 = OH$ and

-continued

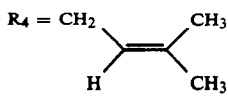

18. The method recited in claim 1, 7, 9, 11, 13, 14 or 15 wherein said compound has a combination of chemical groups $R_1$ to $R_4$ as follows:

Ib: $R_1$ = H, $R_2$ = OH, $R_3$ monophosphate, and

-continued

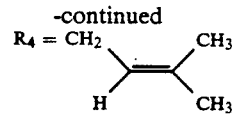

19. The method recited in claim 1, 7, 9, 11, 13, 14 or 15 wherein said compound is contained in a macrophage specific liposome micell.

20. The method recited in claim 1, 7, 9, 11, 13, 14 or 15 wherein said pharmaceutical formation is in the form of a gelatine capsule, tablet, dragee, syrup, suspension, topical cream, suppository, injectable solution, or a kit for the preparation of a syrup, suspension, topical cream, suppository or injectable solution, or is contained in a silicone disc, polymer beads or a transdermal patch.

21. The method recited in claim 1, 7, 9, 11, 13, 14 or 15 further comprising administering to said being an effective amount of an adenosine deaminase inhibitor.

* * * * *